(12) United States Patent
Funahashi et al.

(10) Patent No.: US 8,987,044 B2
(45) Date of Patent: Mar. 24, 2015

(54) PERYLENE TETRACARBOXYLIC ACID BISIMIDE DERIVATIVE, N-TYPE SEMICONDUCTOR, A METHOD FOR PRODUCING N-TYPE SEMICONDUCTOR, AND ELECTRONIC DEVICE

(75) Inventors: Masahiro Funahashi, Takamatsu (JP); Nozomi Takeuchi, Takamatsu (JP)

(73) Assignee: National University Corporation Kagawa University, Kagawa (JP)

( * ) Notice: Subject to any disclaimer, the term of this patent is extended or adjusted under 35 U.S.C. 154(b) by 0 days.

(21) Appl. No.: 14/009,709

(22) PCT Filed: Apr. 4, 2012

(86) PCT No.: PCT/JP2012/059270
§ 371 (c)(1),
(2), (4) Date: Oct. 3, 2013

(87) PCT Pub. No.: WO2012/137853
PCT Pub. Date: Oct. 11, 2012

(65) Prior Publication Data
US 2014/0024171 A1 Jan. 23, 2014

(30) Foreign Application Priority Data
Apr. 4, 2011 (JP) ................. 2011-083220

(51) Int. Cl.
| H01L 51/00 | (2006.01) |
| C07F 7/02 | (2006.01) |
| C07D 471/04 | (2006.01) |
| C07F 7/08 | (2006.01) |
| H01L 51/50 | (2006.01) |

(52) U.S. Cl.
CPC ........ *H01L 51/0003* (2013.01); *H01L 51/0053* (2013.01); *C07D 471/04* (2013.01); *C07F 7/0854* (2013.01); *H01L 51/0094* (2013.01); *H01L 51/5072* (2013.01); *Y02E 10/549* (2013.01)
USPC ............................. 438/99; 546/14

(58) Field of Classification Search
USPC ............................. 438/99; 546/14
See application file for complete search history.

(56) References Cited

U.S. PATENT DOCUMENTS

| 5,451,655 A | 9/1995 | Linde et al. |
| 2010/0237327 A1 | 9/2010 | Funahashi et al. |
| 2011/0042651 A1 | 2/2011 | Koenemann et al. |

FOREIGN PATENT DOCUMENTS

| JP | 8-051102 | 2/1996 |
| JP | 2008-013539 | 1/2008 |
| JP | 2009/000756 | 12/2008 |
| JP | 2009-137848 | 6/2009 |
| JP | 2009-532436 | 9/2009 |
| JP | 2009-231407 | 10/2009 |
| JP | 2010-500430 | 1/2010 |
| JP | 2010-196019 | 9/2010 |
| JP | 2010-531056 | 9/2010 |
| WO | 2008/017593 | 2/2008 |

OTHER PUBLICATIONS

Tokito, "Foundation of Organic EL Element", Expected Materials for the Future, 2009, vol. 9, No. 6, pp. 2-8.
Kitamura et al., Journal of Physics: Condensed Matter, "Pentacene-based organic field-effect transistors", 2008, vol. 20, p. 184011.
Brabec et al., "Plastic Solar Cells", Advanced Functional Materials, 2001, vol. 11, No. 1, pp. 15-26.
Dodabalapur, "Organic and polymer transistors for electronics", Materials today, 2006, vol. 9, No. 4, pp. 24-30.
Sariiftci et al., "Photoinduced Electron Transfer from a Conducting Polymer to Buckminsterfullerene", Science, 1992, vol. 258, pp. 1474-1476.
Funahashi, "Thin-Film Transistor by Solution Process Using Liquid-Crystalline Semiconductor", Ekisho, 2008, vol. 12, No. 4, pp. 259-268.
Funahashi et al., "High Ambipolar Mobility in a Highly Ordered Smectic Phase of a Dialkylphenylterthiophene Derivative That Can Be Applied to Solution-Processed Organic Field-Effect Transistors", Advanced Materials, 2007, vol. 19, pp. 353-358.

(Continued)

*Primary Examiner* — Porfirio Nazario Gonzalez
(74) *Attorney, Agent, or Firm* — Hamre, Schumann, Mueller & Larson, P.C.

(57) ABSTRACT

The present invention provides a perylene tetracarboxylic acid bisimide derivative which enables the formation of an n-type semiconductor having high carrier mobility and has superior solubility. The perylene tetracarboxylic acid bisimide derivative is a perylene tetracarboxylic acid bisimide derivative represented by the following chemical formula (I), a tautomer or stereoisomer of the perylene tetracarboxylic acid bisimide derivative, or a salt of the perylene tetracarboxylic acid bisimide derivative or the tautomer or stereoisomer,

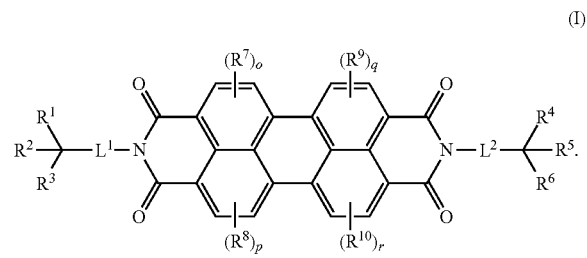

In the chemical formula (I), $R^1$ to $R^6$ each represents a hydrogen atom, organooligosiloxane, or any substituent, at least one of $R^1$ to $R^6$ represents a monovalent substituent derived from organooligosiloxane, $L^1$ and $L^2$ each represents a single bond or a linking group, $R^7$ to $R^{10}$ each represents a lower alkyl group or a halogen, and o, p, q, and r each represents an integer from 0 to 2.

19 Claims, 22 Drawing Sheets

(56) References Cited

OTHER PUBLICATIONS

Funahashi, "Development of Liquid-Crystalline Semiconductors with High Carrier Mobilities and Their Application to Thin-film Transistors", Polymer Journal, 2009, vol. 41, No. 6, pp. 459-469.

Zhang et al., "Flexible field-effect transistors from a liquid crystalline semiconductor by solution processes", Organic Electronics, 2010, vol. 11, pp. 363-368.

Adam et al., "Transient Photoconductivity in a Discotic Liquid Crystal", Physical Review Letters, 1993, vol. 70, No. 4, pp. 457-460.

Schouten et al., "The Effect of Structural Modifications on Charge Migration in Mesomorphic Phthalocyanines", J. Am. Chem. Soc., 1994, vol. 116, pp. 6880-6894.

Pisula et al., "A Zone-Casting Technique for Device Fabrication of Field-Effect Transistors Based on Discotic Hexa-peri-hexabenzocoronene", Advanced Materials, 2005, vol. 17, No. 6, pp. 684-689.

Funahashi et al., "High Carrier Mobility up to 0.1 cm2V-1s-1 at Ambient Temperatures in Thiophene-Based Smectic Liquid Crystals", Advanced Materials, 2005, vol. 17, No. 5, pp. 594-598.

Nakanishi et al., "Electron Transport and Electrochemistry of Mesomorphic Fullerenes with Long-Range Ordered Lamellae", J. Am. Chem. Soc., 2008, vol. 130, pp. 9236-9237.

Tang, "Two-layer organic photovoltaic cell", Applied Physics Letters, 1986, vol. 48, No. 2, pp. 183-185.

Malenfant et al., "N-type organic thin-film transistor with high field-effect mobility based on a N,N' -dialkyl-3,4,9,10-perylene tetracarboxylic diimide derivative", Applied Physics Letters, 2002, vol. 80, No. 14, pp. 2517-2519.

Chen et al., "Effect of Core Twisting on Self-Assembly and Optical Properties of Perylene Bisimide Dyes in Solution and Columnar Liquid Crystalline Phases", Chemistry A European Journal, 2007, vol. 13, pp. 450-465.

An et al., "High Electron Mobility in Room-Temperature Discotic Liquid-Crystalline Perylene Diimides", Advanced Materials, 2005, vol. 17, pp. 2580-2583.

Duzhko et al., "Long-range electron transport in a self-organizing n-type organic material", Applied Physics Letters, 2008, vol. 92, p. 113312.

Wicklein et al., "Room temperature liquid crystalline perylene diester benzimidazoles with extended absorption", Journal of Materials Chemistry, 2010, vol. 20, pp. 8646-8652.

Würthner, "Perylene bisimide dyes as versatile building blocks for functional supramolecular architectures", Chem. Commun., 2004, pp. 1564-1579.

Newton et al., "Synthesis and Properties of Low-molar-mass Liquid-crystalline Siloxane Derivatives", J. Mater. Chem., 1994, vol. 4, No. 6, pp. 869-874.

Zelcer et al., "Mesomorphism of Hybrid Siloxane-Triphenylene Star-Shaped Oligomers", Chem. Mater., 2007, vol. 19, pp. 1992-2006.

Roland et al., "Ultrafast broadband laser spectroscopy reveals energy and charge transfer in novel donor-acceptor triads for photovoltaic applications", Journal of Physics: Conference Series, 2011, vol. 276, p. 012006.

Cazacu et al., "New imides based on perylene and siloxane derivatives", Dyes and Pigments, 2011, vol. 90, No. 20, pp. 106-113.

Yao et al., "Pigment-Mediated Nanoweb Morphology of Poly (dimethylsiloxane)-Substituted Perylene Bisimides", Macromolecules, 2006, vol. 39, No. 23, pp. 7786-7788.

Yao, "Poly(dimethyl siloxane) perylene bisimides", Studies on the Structure and Morphology Perylene Containing Polymers, 2005, PhD thesis, Aug. 2005.

van der Boom et al., "Self-assembly of Photofunctional Siloxane-Based Calix[4]arenes on Oxide Surfaces", Chemistry of Materials, 2003, vol. 15, No. 21, pp. 4068-4074.

FIG. 9C  With one polarizer, 136.1° C

ITO/ITO cell, d = 9 mm, rubbing on the ITO surface without an alignment layer  X100

{(Me3SiOSiMe2)2C}2PTCBI, columnar phase, 40°C, ITO/ITO, d = 25µm, $\lambda$ = 356 nm {(Me3SiOSiMe2)2C}2PTCBI, columnar phase, 40°C, ITO/ITO, d = 25µm, $\lambda$ = 356 nm

PERYLENE TETRACARBOXYLIC ACID BISIMIDE DERIVATIVE, N-TYPE SEMICONDUCTOR, A METHOD FOR PRODUCING N-TYPE SEMICONDUCTOR, AND ELECTRONIC DEVICE

TECHNICAL FIELD

The present invention relates to a perylene tetracarboxylic acid bisimide derivative, an n-type semiconductor, a method for producing an n-type semiconductor, and an electronic device.

BACKGROUND ART

Organic semiconductors are applied to not only electrophotographic photoreceptors but also electronic devices including an electroluminescence element (Non-Patent Document 1), thin-film transistor (Non-Patent Document 2), a solar battery (Non-Patent Document 3), and the like. Moreover, it has been considered that organic semiconductors can be applied to electronic paper, utilizing its flexibility (Non-Patent Document 4).

From the point of view of producing practical devices, it is desired that thin films can be produced by solution processing, which can be conducted at low cost. However, currently-available organic semiconductors used in electroluminescence elements and field-effect transistors are required to be produced by vacuum processing in many cases.

Vacuum-deposited films have been used in organic thin-film solar batteries for a long time. In order to solve this concern, a fullerene derivative including a conjugate polymer or a substituent introduced thereinto, capable of being formed into a thin film by solution processing, has been used since the development of a bulk hetero junction-type organic thin-film solar battery by N. S. Sariciftci in 1993 (Non-Patent Document 5). However, an aggregation structure of a polymer or a conjugate polymer is an amorphous structure, so that carrier mobility is low.

On the other hand, a liquid crystalline semiconductor has received attention in recent years as a novel organic semiconductor material which can be formed into a thin film by solution processing and has high electron mobility (carrier mobility) (Non-Patent Document 6). In a higher-order liquid crystal phase of a liquid crystal material having an aromatic ring in a core region thereof, a molecular aggregation structure similar to a molecular crystal is formed, so that high-speed electron conduction as in the molecular crystal can be achieved. Moreover, the liquid crystal material generally has a long chain of an alkyl group, so that solubility in an organic solvent is high. Thus, the liquid crystal material can be formed into a film by solution processing. In addition, in the liquid crystal phase, flexibility and flowability based on the degree of freedom of molecular motion are exerted, so that the liquid crystal material is characterized in that formation of grain boundary, which is a problem in polycrystal, thin film is suppressed, and a high quality semiconductor thin film having high carrier mobility can be produced easily. The inventors of the present invention have succeeded in producing a field-effect transistor by solution processing using a liquid crystalline semiconductor (Non-Patent Documents 7 to 8 and Patent Documents 1 to 3). The inventors of the present invention further found that even if a 3% strain is applied to a field-effect transistor produced on a polymer substrate by solution processing using a liquid crystalline semiconductor, the properties of the field-effect transistor are not at all changed (Non-Patent Document 9, Patent Document 3).

As a liquid crystalline semiconductor having p-type (also referred to as "p type") conductivity, many liquid crystalline semiconductors such as a triphenylene derivative (Non-Patent Document 10), a phthalocyanine derivative (Non-Patent Document 11), a hexabenzocoronene derivative (Non-Patent Document 12), and an oligothiophene derivative (Non-Patent Document 13) are known.

As an n-type (also referred to as "n type") liquid crystalline semiconductor, liquid crystalline fullerene having an alkyl group introduced thereinto has been reported, for example, and electron transport has been found therein (Non-Patent Document 14).

A perylene tetracarboxylic acid derivative long has been known as an n-type semiconductor. That is, first, a vacuum-deposited film of perylene tetracarboxylic acid bisimide has been studied for a solar battery (Non-Patent Document 15) or a field-effect transistor (Non-Patent Document 16). Further, it has been found that a perylene tetracarboxylic acid bisimide derivative having a plurality of alkyl chains introduced thereinto exhibits a liquid crystal phase (Non-Patent Document 17). Furthermore it has been reported that a perylene tetracarboxylic acid imide derivative having a gallic acid ether portion has high electron mobility by space charge limited current measurement (Non-Patent Document 18). Another perylene tetracarboxylic acid imide derivative exhibits a liquid crystal phase at around room temperature, and electron mobility at room temperature has been measured by a Time-of-Flight (TOF) method (Non-Patent Document 19). In addition, an n-type perylene tetracarboxylic acid derivative which exhibits a liquid crystal phase at room temperature has been synthesized (Non-Patent Document 20). Moreover, it has been studied that a substituent is introduced into an aromatic ring portion in order to improve solubility of a perylene tetracarboxylic acid derivative in an organic solvent (Non-Patent Document 21).

PRIOR ART DOCUMENTS

Patent Document

Patent Document 1: JP 2008-013539 A
Patent Document 2: JP 2009-137848 A
Patent Document 3: JP 2009-231407 A

Non-Patent Documents

Non-Patent Document 1: S. Tokito, MIRAI ZAIRYO (Future Material), June 2009, p. 2
Non-Patent Document 2: M. Kitamura, Y. Arakawa, J. Phys.: Condens. Matter, 20, 184011 (2008)
Non-Patent Document 3: C. J. Brabec, N. S. Sariciftci, J. C. Hummelen, Adv. Funct. Mater., 11, 15 (2001)
Non-Patent Document 4: A. Dodabalapur, Materials Today, 9, 24 (2006)
Non-Patent Document 5: N. S. Sariciftci, L. Smilowitz, A. J. Heeger, F. Wudl, Science, 258, 1474 (1992)
Non-Patent Document 6: M. Funahashi, EKISHO (Liquid Crystal), October 2006, pp. 359-368
Non-Patent Document 7: M. Funahashi, F. Zhang, N. Tamaoki, Adv. Mater. 19, 353 (2007)
Non-Patent Document 8: M. Funahashi, Polymer Journal, 41, 459 (2009)
Non-Patent Document 9: M. Funahashi, F. Zhang, N. Tamaoki, Org. Electr., 11, 363 (2010)
Non-Patent Document 10: D. Adam, F. Closs, T. Frey, D. Funhoff, D. Haarer, H. Ringsdorf, P. Schuhmacher, K. Siemensmeyer, Phys. Rew. Lett, 70, 457 (1993)

Non-Patent Document 11: P. G. Schouten, J. M. Warman, M. P. de Haas, C. F. van Nostrum, G. H. Gelinck, R. J. M. Nolte, M. J. Copyn, J. W. Zwikker, M. K. Engel, M. Hanack, Y. H. Chang, W. T. Fords, J. Am. Chem. Soc., 116, 6880 (1994)

Non-Patent Document 12: W. Pisula, A. Menon, M. Stepputat, I. Lieberwirth, U. Kolb, A. Tracz, H. Sirringhaus, T. Pakula, and K. Muellen, Adv. Mater., 17, 684 (2005)

Non-Patent Document 13: M. Funahashi and J. Hanna, Adv. Mater., 17, 594-598 (2005)

Non-Patent Document 14: T. Nakanishi, Y. Shen, J. Wang, S. Yagai, M. Funahashi, T. Kato, P. Fernandes, H. Moehwald, and D. G. Kurth, J. Am. Chem. Soc., 130, 9236 (2008)

Non-Patent Document 15: C. W. Tang, Appl. Phys. Lett., 48, 183 (1986).

Non-Patent Document 16: P. R. Malenfant, C. D. Dimitrakopoulos, J. D. Gelorme, L. L. Kosbar, T. O. Graham, Appl. Phys. Lett., 80, 2517 (2002)

Non-Patent Document 17: Z. Chen, U. Baumeister, C. Tschierske, F. Wuerthner, Chem. Eur. J., 13, 450 (2007)

Non-Patent Document 18: Z. An, J. Yu, S. C. Jones, S. Barlow, S. Yoo, B. Domercq, P. Prins, L. D. A. Siebbeles, B. Kippelen, S. R. Marder, Adv. Mater., 17, 2580 (2005)

Non-Patent Document 19: V. Duzhko, E. Aqad, M. R. Imam, M. Peterca, V. Percec, K. D. Singer, Appl. Phys. Lett., 92, 113312 (2008)

Non-Patent Document 20: A. Wicklein, M-A. Muth, M. Thelakkat, J. Mater. Chem., 20, 8646 (2010)

Non-Patent Document 21: F. Wuerthner, Chem. Commun., 1564 (2004)

SUMMARY OF INVENTION

Problem to be Solved by the Invention

As in an inorganic semiconductor device, it is required to use a p-type semiconductor and an n-type semiconductor in combination in an organic semiconductor device in many cases. However, many of organic semiconductors which have been researched are p-type semiconductors (e.g., Non-Patent Documents 6 to 13 and Patent Documents 1 to 3). A research on n-type organic semiconductor has been barely promoted compared with a research on p-type organic semiconductor. Therefore, unlike a p-type organic semiconductor, an n-type organic semiconductor having both of high solubility and high electron mobility (carrier mobility) in bulk state has not been known. For example, an electron mobility of liquid crystalline fullerene evaluated by a Time-of-Flight method is $10^{-3}$ cm$^2$/Vs, which is low, in Non-Patent Document 14. The perylene tetracarboxylic acid derivative described in Non-Patent Documents 15 and 16 has really low solubility in an organic solvent and is thus impossible to be formed into a film by solution processing. In a perylene tetracarboxylic acid bisimide derivative having a plurality of alkyl chains introduced thereinto, described in Non-Patent Document 17 and the like, there are only a limited number of compounds whose electronic physical properties such as carrier mobility and photoconductivity have been clearly evaluated. Electron transport properties of a perylene tetracarboxylic acid imide derivative described in Non-Patent Document 18 depend on a sample preparation method and are thus inferior in reproducibility. An electron mobility of a perylene tetracarboxylic acid imide derivative described in Non-Patent Document 19 at room temperature is $10^{-5}$ cm$^2$/Vs orders of magnitude, which is low, and is equal to that of a general amorphous semiconductor. In Non-Patent Document 20, electronic physical properties of an n-type perylene tetracarboxylic acid derivative described in Non-Patent Document 20 have not been studied. It has not been studied that a liquid crystalline perylene tetracarboxylic acid derivative described in Non-Patent Documents 17 to 20 is formed into a film by solution processing such as spin coating. In Non-Patent Document 21, as mentioned above, it has been studied that a substituent is introduced into an aromatic ring portion in order to improve solubility of a perylene tetracarboxylic acid derivative in an organic solvent. However, this method causes an overlap between in orbits of molecules to be small and is thus insufficient as a molecular design of an organic semiconductor having high carrier mobility.

Hence, the present invention is intended to provide a perylene tetracarboxylic acid bisimide derivative which enables an n-type semiconductor having high carrier mobility to be produced and is superior in solubility. The present invention further provides an n-type semiconductor using the perylene tetracarboxylic acid bisimide derivative, a method for producing the n-type semiconductor, and an electronic device.

Means for Solving Problem

In order to achieve the aforementioned object, the perylene tetracarboxylic acid bisimide derivative according to the present invention is a perylene tetracarboxylic acid bisimide derivative represented by the following chemical formula (I); a tautomer or stereoisomer of the perylene tetracarboxylic acid bisimide derivative; or a salt of the perylene tetracarboxylic acid bisimide derivative or the tautomer or stereoisomer, (I)

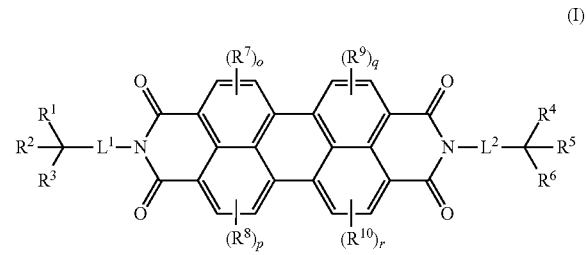

where in the chemical formula (I),

R$^1$ to R$^6$ each represents a hydrogen atom, a monovalent substituent derived from organooligosiloxane, or any substituent and may be identical to or different from one another, where at least one of R$^1$ to R$^6$ represents a monovalent substituent derived from organooligosiloxane, and the organooligosiloxane may or may not further have a substituent, R$^7$ to R$^{10}$ each represents a lower alkyl group, a lower alkoxy group, or a halogen and may be identical to or different from one another, L$^1$ and L$^2$ each represents a single bond or a linking group and may be identical to or different from each other, and o, p, q, and r each represents the number of substituents, which is an integer from 0 to 2 and may be identical to or different from one another, where when o is 2, two R$^7$s may be identical to or different from each other, when p is 2, two R$^8$s may be identical to or different from each other, and when q is 2, two R$^9$s may be identical to or different from each other, and when r is 2, two R$^{10}$s may be identical to or different from each other.

The n-type semiconductor according to the present invention is an n-type semiconductor including the perylene tetracarboxylic acid bisimide derivative according to the present invention, a tautomer or stereoisomer of the perylene tetracarboxylic acid bisimide derivative, or a salt of the perylene tetracarboxylic acid bisimide derivative or the tautomer or stereoisomer.

The method for producing the n-type semiconductor according to the present invention includes: a solution preparation step of dissolving the perylene tetracarboxylic acid bisimide derivative according to the present invention, a tautomer or stereoisomer of the perylene tetracarboxylic acid bisimide derivative, or a salt of the perylene tetracarboxylic acid bisimide derivative or the tautomer or stereoisomer in a solvent to prepare a solution; a coating step of coating a base with the solution to form a coating film; and a drying step of drying the coating film.

The electronic device according to the present invention includes the n-type semiconductor according to the present invention.

Effects of the Invention

According to the present invention, a perylene tetracarboxylic acid bisimide derivative which enables an n-type semiconductor having high carrier mobility to be formed and is superior in solubility can be provided. According to the present invention, an n-type semiconductor using the perylene tetracarboxylic acid bisimide derivative, a method for producing the n-type semiconductor, and an electronic device can further be provided.

BRIEF DESCRIPTION OF DRAWINGS

FIG. 9A is a polarization microscope photograph taken at 136° C. FIG. 9B is a polarization microscope photograph taken at 30° C. FIG. 9C is a polarization microscope photograph taken at 136.1° C. with one polarizer.

DESCRIPTION OF EMBODIMENTS

Figure 1A:
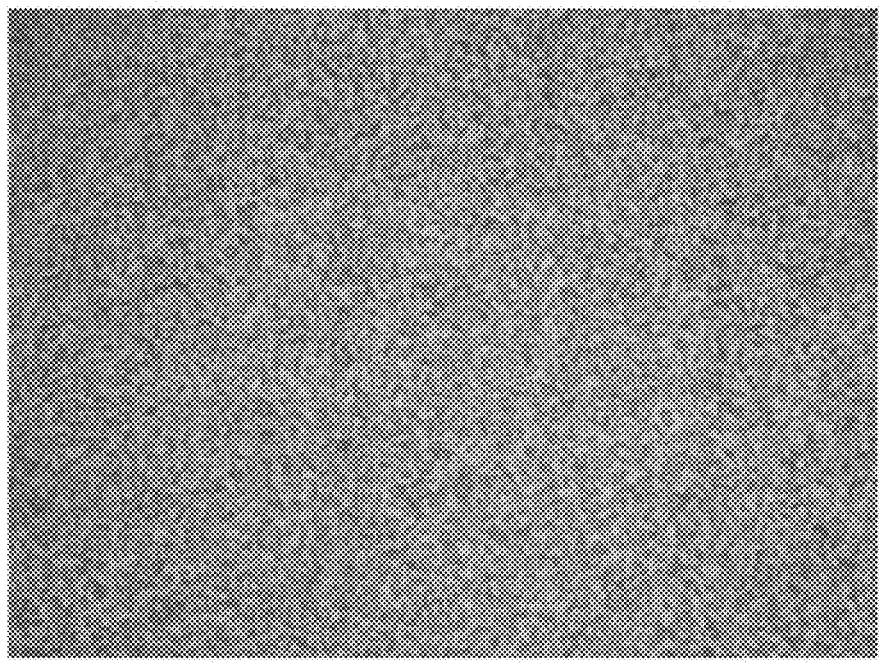
FIG. 1A is a polarization microscope photograph of a liquid crystal sample produced in Example 3 at 30° C. (Sm phase) in the case where the liquid crystal sample is rapidly cooled from 220° C.

The present invention is described below with reference to examples. The present invention, however, is not limited by the following description. When the present invention is defined by a numerical limitation, the numerical value may be exactly the numerical value or about the numerical value. For example, when the number of carbon atoms is "from 0 to 20", the number may be exactly from 0 to 20 or from about 0 to about 20. Moreover, for example, when a temperature is "from 20° C. to 40° C., the temperature may be exactly from 20° C. to 40° C. or from about 20° C. to about 40° C.

[Perylene Tetracarboxylic Acid Bisimide Derivative]

The perylene tetracarboxylic acid bisimide derivative according to the present invention (hereinafter also merely referred to as "the compound according to the present invention") has a monovalent substituent derived from organooligosiloxane (hereinafter also merely referred to as "an organooligosiloxane group") as represented by the chemical formula (I). The compound according to the present invention, represented by the chemical formula (I) enables an n-type semiconductor having high carrier mobility to be produced and is superior in solubility.

A liquid crystal material in which an organooligosiloxane site has been introduced into an end of an alkyl side chain has been synthesized. Specifically, it is known that formation of a layer structure, i.e., exhibition of a smectic phase, progresses by separation of a nano phase from an alkyl chain or an aromatic ring core region with a liquid organooligosiloxane site (J. Newton, H. Coles, P. Hodge, J. Hannington, J. Mater. Chem., 4, 869 (1994)). The same studies have been conducted with respect to a triphenylene derivative, and it has been reported that exhibition of a columnar phase progresses by separation of a nano phase with a triphenylene derivative (A. Zelcer, B. Donnio, C. Bourgogne, F. D. Cukiernik, D. Guillon, Chem. Mater., 19, 1992 (2007)).

However, there have been no previous cases in which an organooligosiloxane group is introduced into an organic semiconductor molecule, and studies on improvement in solubility and film-forming properties have not been conducted. Moreover, studies on electronic physical properties of a semiconductor of a liquid crystal material in which an oligoorganosiloxane group has been introduced have not at all been conducted.

Inventors of the present invention found a challenge of having both of high solubility and high carrier mobility in an n-type organic semiconductor and conducted earnest studies in order to overcome the challenge. Then, they found a compound according to the present invention in which an organooligosiloxane group has been introduced into a perylene tetracarboxylic acid bisimide derivative and reached the present invention. The compound according to the present invention has a high electron affinity, so that it is suitable to be used in an n-type semiconductor. Moreover, the compound according to the present invention has high carrier mobility (electron mobility), so that favorable electron transport properties can be exerted.

A electron-conjugated system, which governs electrical conductivity of an organic semiconductor, is generally electron rich, so that it is prone to exert p-type electrical conductivity. Therefore, it is difficult to design and synthesize an electron-poor in electron-conjugated system, which is prone to exert n-type electrical conductivity. Thus, there are small variations of a skeleton of an n-type organic semiconductor compared with a p-type organic semiconductor, and only a few structures such as a perylene tetracarboxylic acid derivative and fullerene are known. Therefore, as mentioned above, an n-type organic semiconductor having both of high solubility and high carrier mobility has not been known.

As mentioned above, according to the prior art documents on a perylene tetracarboxylic acid derivative and the like (e.g., Non-Patent Documents 14 to 21), both of high solubility and high carrier mobility cannot be achieved, or studies on achieving both of them are not conducted. In contrast, the perylene tetracarboxylic acid bisimide derivative according to the present invention can have both of high solubility and high carrier mobility. The reason for this is not clear, but however can be described as follows, for example.

That is, first, when the skeletons of π electron-conjugated systems are identical to each other, an improvement in solubility and an improvement in carrier mobility are prone to be in a trade-off relationship. That is, in order to increase solubility, it is effective to weaken an interaction between the π electron-conjugated systems. However, when the interaction between the π electron-conjugated systems is weakened, an overlap between π orbits becomes small, resulting in reduction in carrier mobility. For example, as mentioned above, in Non-Patent Document 21, in order to improve solubility of a perylene tetracarboxylic acid derivative in an organic solvent, a substituent is introduced into an aromatic ring. However, an overlap between π orbits of molecules becomes small, resulting in reduction in carrier mobility. In contrast, in the present invention, it is considered that an introduction of an organooligosiloxane group enables a molecular aggregation state of a perylene tetracarboxylic acid bisimide derivative to be controlled appropriately, and thus, solubility can be improved without impairing an overlap (stacking) between π orbits. This description, however, is merely an example, and the present invention is not limited thereby.

Moreover, although the reason why an electron affinity of a perylene tetracarboxylic acid imide derivative is high is not clear, it is considered that an imide group (carbonyl group) attracts electrons from a perylene ring, so that the perylene ring becomes electron poor, resulting in an increase in electron affinity, for example. This description also, however, is merely an example of a possible mechanism, and the present invention is not limited thereby.

In the chemical formula (I) of the perylene tetracarboxylic acid bisimide derivative according to the present invention, at least one of $R^1$ to $R^6$ is a monovalent substituent derived from organooligosiloxane as mentioned above. The monovalent substituent derived from organooligosiloxane is not particularly limited and is preferably a substituent represented by the following chemical formula (II) or (II-2).

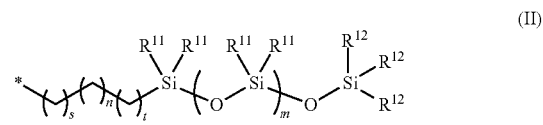

(II)

-continued

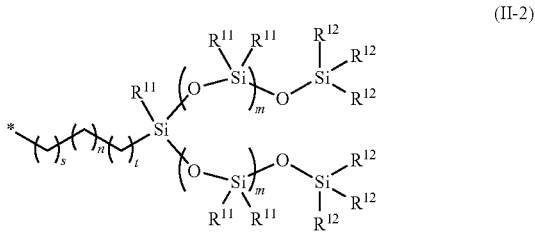

(II-2)

In the chemical formulae (II) and (II-2), $R^{11}$s and $R^{12}$s each represents a hydrogen atom, a lower alkyl group, or a fluorine atom and may be identical to or different from one another, $R^1$s may be identical to or different from one another, and $R^{12}$s may be identical to or different from one another, m represents 0 or a positive integer, and when a plurality of ms is present in the chemical formula (I), ms may be identical to or different from one another, n represents 0 or a positive integer, and when a plurality of ns is present in the chemical formula (I), ns may be identical to or different from one another, s represents 0 or 1, t represents 1 or 2, and * represents an atomic bonding to a carbon atom in the chemical formula (I).

From the viewpoint of the ease of exerting liquid crystal properties in the compound according to the present invention, each m in the chemical formula (II) is preferably an appropriate numerical value. A specific numerical value of m in the chemical formula (II) is preferably an integer from 0 to 20, more preferably an integer from 0 to 6 although it depends on the number of organooligosiloxane groups in the chemical formula (I). The m may be, for example, 0 or an integer of 1 or more. Specifically, m=0 is preferable because really high carrier mobility can be obtained in some cases as in the compounds (2-44) and (2-46) shown in the examples described below. The n is preferably an integer from 0 to 30, more preferably an integer from 0 to 18. In $R^{11}$ and $R^{12}$, the lower alkyl group is preferably a straight-chain or branched alkyl group with a carbon number from 1 to 5, particularly preferably a methyl group.

At least one of $R^1$ to $R^6$ in the chemical formula (I) is an organooligosiloxane group, and each of the others may be an organooligosiloxane group, a hydrogen atom, or any substituent. Examples of the any substituent include an alkyl group, an alkenyl group, an alkynyl group, a haloalkyl group, a hydroxyalkyl group, an aminoalkyl group, an alkanoyl group, an alkoxy group, an alkylamino group, a perfluoroalkyl group, an alkenyl group, an alkoxyalkyl group, an acyl group, an alkanoyl group, an acyloxy group, and an alkanoyl oxy group.

In the chemical formula (I), in $L^1$ and $L^2$, the linking group is an alkylene group, a saturated hydrocarbon group having a circular structure, an unsaturated hydrocarbon group, an oxy group (—O—), a thio group (—S—), a seleno group (—Se—), an amide bond (—NH—CO— or —CO—NH—), an ester bond (—CO—O— or —O—CO—), an imino group (—NH—), or a thioester bond (—CO—S— or —S—CO—). Each of the alkylene group, the saturated hydrocarbon group having a circular structure, or the unsaturated hydrocarbon group may or may not further have a substituent. When a methylene group is present in the alkylene group, the saturated hydrocarbon group having a circular structure, or the unsaturated hydrocarbon group, the methylene group may be replaced with an oxy group (—O—), a thio group (—S—), a seleno group (—Se—), an amide bond (—NH—CO— or —CO—NH—), an ester bond (—CO—O— or —O—CO—), an imino group (—NH—), or a thioester bond (—CO—S— or —S—CO—). The alkylene group may be, for example, a straight-chain or branched alkylene group with a carbon number from 1 to 8. The saturated hydrocarbon group having a circular structure may be, for example, a monocyclic or condensed-ring cycloalkylene group with a carbon number from 3 to 10 or a group in which an alkylene group (e.g., a straight-chain or branched alkylene group with a carbon number from 1 to 8) is bound to one or both sides of the monocyclic or condensed-ring cycloalkylene group. The monocyclic or condensed-ring cycloalkylene group with a carbon number from 3 to 10 is not particularly limited and can be, for example, a cycloalkylene group derived from cyclohexane, decalin, or the like. The unsaturated hydrocarbon group may be, for example, the alkylene group or a group in which a single bond or a plurality of single bonds in the saturated hydrocarbon group having a circular structure is replaced with a double bond or a triple bond. When the unsaturated hydrocarbon group has a circular structure, the circular structure may be an aromatic ring or a non-aromatic ring. When the alkylene group, the saturated hydrocarbon group having a circular structure, or the unsaturated hydrocarbon group further has a substituent, the number of substituents may be one or more. The substituent is not particularly limited, and examples thereof include an alkyl group, an alkenyl group, an alkynyl group, a haloalkyl group, a hydroxyalkyl group, an aminoalkyl group, an alkanoyl group, an alkoxy group, an alkylamino group, a perfluoroalkyl group, an alkenyl group, an alkoxyalkyl group, an acyl group, an alkanoyl group, an acyloxy group, and an alkanoyl oxy group. In the $L^1$ and $L^2$, the linking group may be a group represented by the following formula (III).

$$*^C\text{-}L^{11}\text{-}Ar\text{-}L^{12}\text{-}*^N \qquad (III)$$

In the formula (III), Ar represents an arylene group. When a plurality of Ars is present in the chemical formula (I), they may be identical to or different from one another. $L^{11}$ and $L^{12}$ are each a single bond, an alkylene group, a saturated hydrocarbon group having a circular structure, an unsaturated hydrocarbon group, an oxy group (—O—), a thio group (—S—), a seleno group (—Se—), an amide bond (—NH—CO— or —CO—NH—), an ester bond (—CO—O— or —O—CO—), an imino group (—NH—), or a thioester bond (—CO—S— or —S—CO—). Each of the alkylene group, the saturated hydrocarbon group having a circular structure, and the unsaturated hydrocarbon group may or may not further have a substituent. When a methylene group is present in the alkylene group, the saturated hydrocarbon group having a circular structure, or the unsaturated hydrocarbon group, the methylene group may be replaced with an oxy group (—O—), a thio group (—S—), a seleno group (—Se—), an amide bond (—NH—CO— or —CO—NH—), an ester bond (—CO—O— or —O—CO—), an imino group (—NH—), or a thioester bond (—CO—S— or —S—CO—). In $L^{11}$ and $L^{12}$, the saturated hydrocarbon group having a circular structure may be, for example, a monocyclic or condensed-ring cycloalkylene group with a carbon number from 3 to 10 or a group in which an alkylene group (e.g., a straight-chain or branched alkylene group with a carbon number from 1 to 8) is bound to one or both sides of the monocyclic or condensed-ring cycloalkylene group. The monocyclic or condensed-ring cycloalkylene group with a carbon number from 3 to 10 is not particularly limited and can be, for example, a cycloalkylene group derived from cyclohexane, decalin, or the like. The unsaturated hydrocarbon group may be, for example, the alkylene group or a group in which a single bond or a plurality of single bonds in the saturated hydrocarbon group having a circular structure may be replaced with a double bond or a triple bond. When the unsaturated hydrocarbon group has a circular structure, the circular structure may be an aromatic ring or a non-aromatic ring. When the alkylene group, the saturated hydrocarbon group having a circular structure, or the unsaturated hydrocarbon group further has a substituent, the number of substituents may be one or more. The substituent is not particularly limited, and examples thereof include an alkyl group, an alkenyl group, an alkynyl group, a haloalkyl group, a hydroxyalkyl group, an aminoalkyl group, an alkanoyl group, an alkoxy group, an alkylamino group, a perfluoroalkyl group, an alkenyl group, an alkoxyalkyl group, an acyl group, an alkanoyl group, an acyloxy group, and an alkanoyl oxy group. $L^{11}$ and $L^{12}$ may be identical to or different from each other. When a plurality of $L^{11}$s is present in the chemical formula (I), they may be identical to or different from one another. When a plurality of $L^{12}$s is present in the chemical formula (I), they may be identical to or different from one another. *C represents an atomic bonding to a carbon atom in the chemical formula (I). *N represents an atomic bonding to a nitrogen atom in the chemical formula (I).

carbon number of each of the lower alkyl group and the alkoxy group is preferably from 1 to 5, more preferably from 1 to 3, particularly preferably from 1 to 2. Each of the lower alkyl group and the alkoxy group can be a straight-chain or branched group.

The perylene tetracarboxylic acid bisimide derivative according to the present invention is more preferably a perylene tetracarboxylic acid bisimide derivative represented by the following chemical formula (1) or (2), a tautomer or stereoisomer of the perylene tetracarboxylic acid bisimide derivative, or a salt of the perylene tetracarboxylic acid bisimide derivative or the tautomer or stereoisomer.

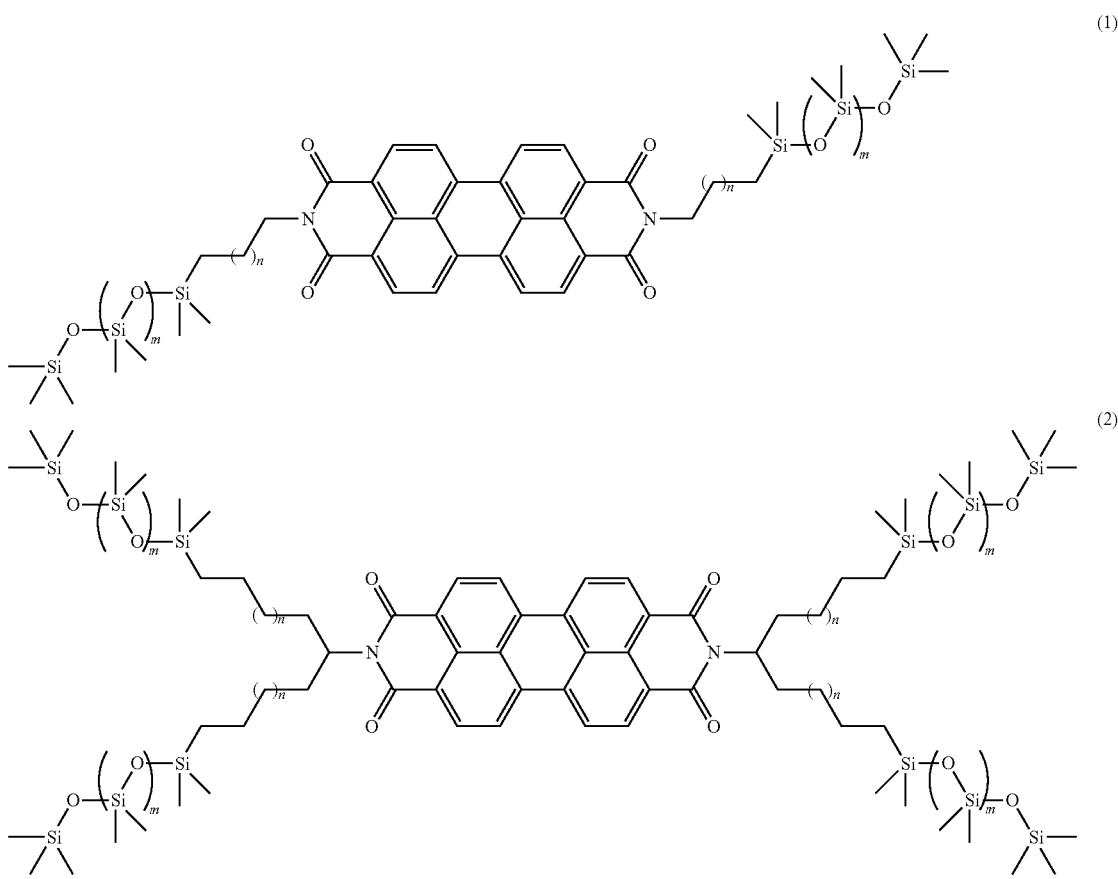

In the formula (III), Ar (arylene group) is not particularly limited and may be, for example, a carbon aromatic ring or a heteroaromatic ring. Ar is preferably an o-phenylene group, a m-phenylene group, a p-phenylene group, a 2,2'-biphenylene group, a 2,3'-biphenylene group, a 2,4'-biphenylene group, a 3,3'-biphenylene group, a 3,4'-biphenylene group, a 4,4'-biphenylene group, or a 2,5-thienylene group. In the chemical formula (III), in $L^1$ and $L^2$, the linking group is preferably a single bond, an alkylene group, an oxy group (—O—), a thio group (—S—), or a seleno group (—Se—).

From the viewpoint of the ease of exhibiting liquid crystal properties in the compound according to the present invention, $R^7$ to $R^{10}$ in the chemical formula (I) are preferably substituents which are not bulky or not present (the number of substituents is 0). For example, in $R^7$ to $R^{10}$, the halogen is preferably bromine (Br) rather than iodine (I), preferably chlorine (Cl) rather than bromine (Br), and preferably fluorine (F) rather than chlorine (Cl). Moreover, in $R^7$ to $R^{10}$, the In the chemical formulae (1) and (2), m and n are the same as those in the chemical formula (II).

From the viewpoint of the ease of exhibiting liquid crystal properties, each m in the perylene tetracarboxylic acid bisimide derivative of the chemical formula (1) is more preferably an integer from 0 to 5. For example, when some or all of ms (specifically all of ms) are 0 in the chemical formula (1), the perylene tetracarboxylic acid bisimide derivative does not exhibit a liquid crystal phase in some cases even through it becomes a crystal. For example, when some or all of ms (specifically all of ms) are 6 or more in the compound of the chemical formula (1), the compound holds the state of an isotropic liquid even when the compound is cooled after being melted by heating, and thus, the compound does not exhibit a liquid crystal phase in some cases. It can be said that the molecule of the chemical formula (1) has a structure in which each nitrogen atom of perylene tetracarboxylic acid bisimide is linked with each straight-chain organooligosiloxane group via a straight-chain alkylene group. Examples of the straight-chain alkylene group include a propylene group (n=1), a butylene group (n=2), a pentylene group (n=3), and a hexylene group (n=4), and the straight-chain alkylene group is particularly preferably a propylene group. Examples of the organo oligosiloxane group at each end include 1,1,1,3,3,-pentamethyl disiloxane (m=0), 1,1,1,3,3,5,5-heptamethyl trisiloxane (m=1), 1,1,1,3,3,5,5,7,7-nonamethyl tetrasiloxane (m=2), and 1,1,1,3,3,5,5,7,7,9,9-undecamethyl pentasiloxane (m=3), and the organo oligosiloxane group is particularly preferably 1,1,1,3,3-pentamethyl disiloxane or 1,1,1,3,3,5,5-heptamethyl trisiloxane.

From the viewpoint of the ease of exhibiting liquid crystal properties, each m in the perylene tetracarboxylic acid bisimide derivative of the chemical formula (2) is more preferably an integer from 0 to 3. For example, when some or all of ms (specifically all of ms) are 0 in the chemical formula (2), the perylene tetracarboxylic acid bisimide derivative does not exhibit a liquid crystal phase in some cases even through it becomes a crystal. However, as in the case of compounds (2-44) and (2-46) of the examples described below, the perylene tetracarboxylic acid bisimide derivative exhibits a liquid crystal phase without any problem in some cases. Moreover, when m=0, really high carrier mobility can be obtained in some cases, as in the case of the compounds (2-44) and (2-46), for example, which is preferable. For example, when some or all of ms (specifically all of ms) are 4 or more in the compound of the chemical formula (2), the compound holds the state of an isotropic liquid even when the compound is cooled after being melted by heating, and thus, the compound does not exhibit a liquid crystal phase in some cases. It can be said that the molecule of the chemical formula (2) has a structure in which each nitrogen atom of perylene tetracarboxylic acid bisimide is linked with a methine group, and the methine group is linked with each straight-chain organooligosiloxane group via a straight-chain alkylene group. Examples of the straight-chain alkylene group include a propylene group (n=0), a butylene group (n=1), a pentylene group (n=2), and a hexylene group (n=3), and the straight-chain alkylene group is particularly preferably a propylene group. Examples of the organo oligosiloxane group at each end include 1,1,1,3,3,-pentamethyl disiloxane (m=0), 1,1,1,3,3,5,5-heptamethyl trisiloxane (m=1), 1,1,1,3,3,5,5,7,7-nonamethyl tetrasiloxane (m=2), and 1,1,1,3,3,5,5,7,7,9,9-undecamethyl pentasiloxane (m=3), and the organo oligosiloxane group is particularly preferably 1,1,1,3,3-pentamethyl disiloxane or 1,1,1,3,3,5,5-heptamethyl trisiloxane.

The perylene tetracarboxylic acid bisimide derivative represented by the chemical formula (1) may be, for example, the perylene tetracarboxylic acid bisimide derivative represented by the following chemical formula (1-1). The perylene tetracarboxylic acid bisimide derivative represented by the chemical formula (2) may be, for example, the perylene tetracarboxylic acid bisimide derivative represented by the following chemical formula (2-1), (2-44), or (2-46). The following chemical formula (1-1) represents the case where all of each m and each n are 1 in the chemical formula (1). The following chemical formula (2-1) represents the case where each m and each n are 1 in the chemical formula (2). The following chemical formula (2-44) represents the case where each m is 0, and each n is 1 in the chemical formula (2). The following chemical formula (2-46) represents the case where each m is 0, and each n is 3 in the chemical formula (2).

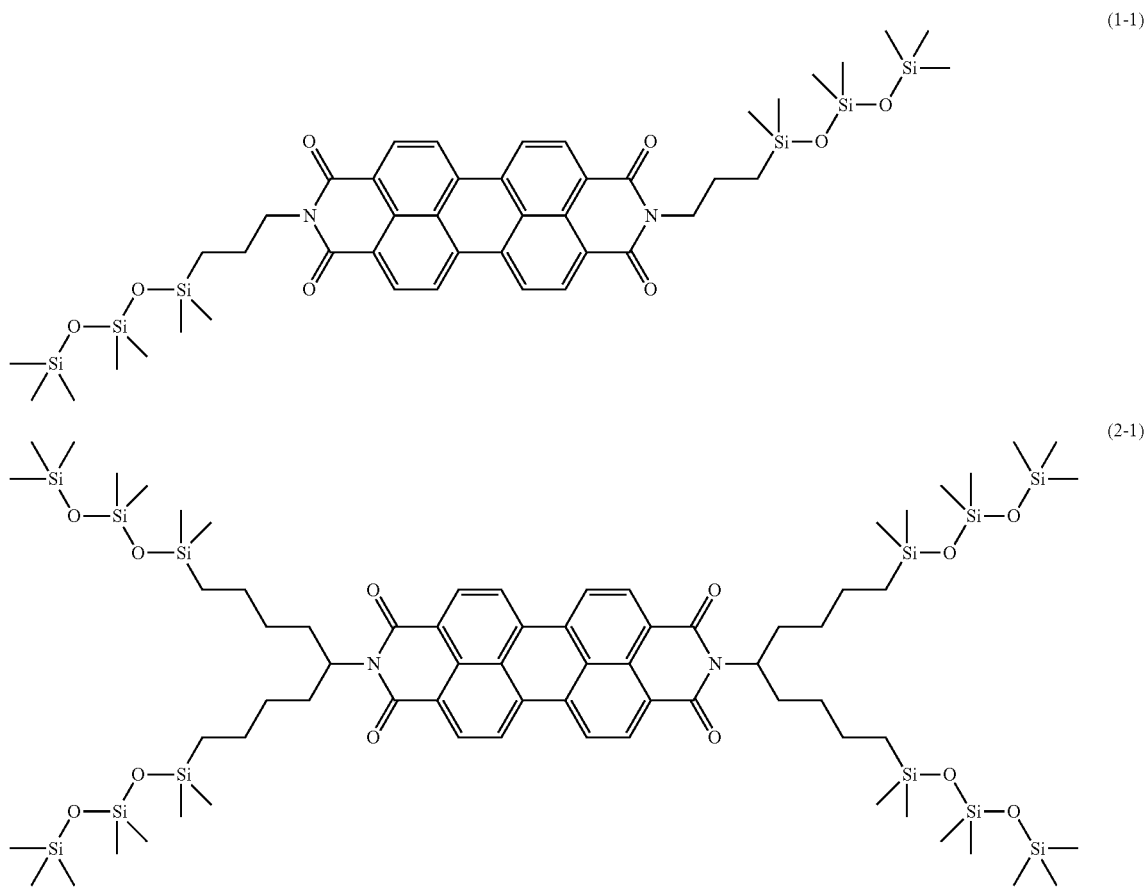

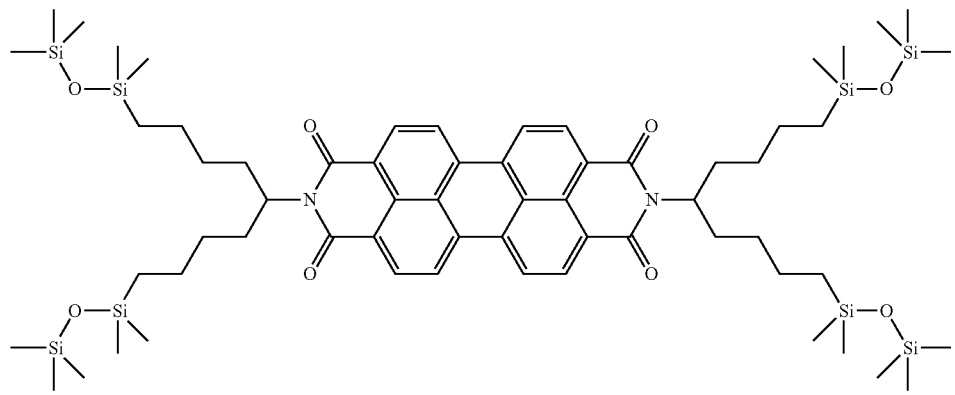

(2-44)

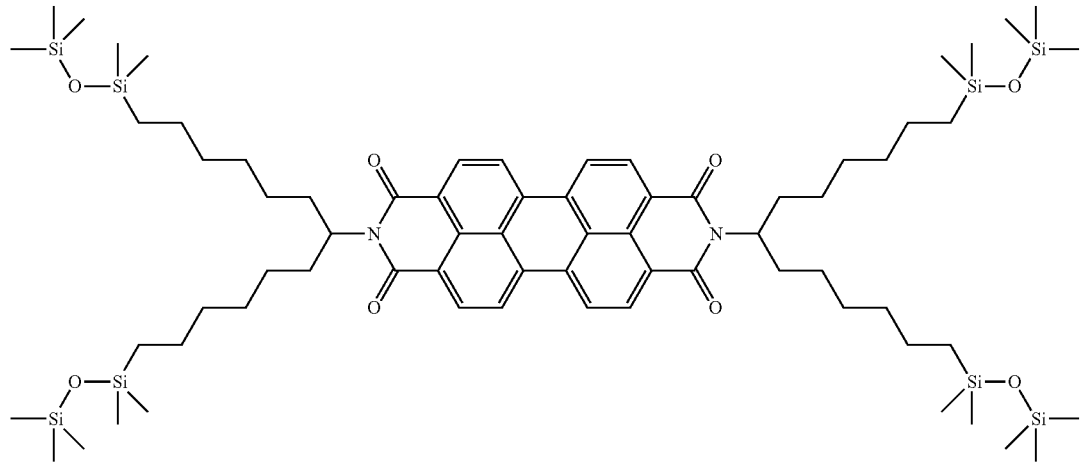

(2-46)

The perylene tetracarboxylic acid bisimide derivative according to the present invention is more preferably a perylene tetracarboxylic acid bisimide derivative represented by the following chemical formula (3), a tautomer or stereoisomer of the perylene tetracarboxylic acid bisimide derivative, or a salt of the perylene tetracarboxylic acid bisimide derivative or the tautomer or stereoisomer.

In the chemical formula (3), m and n are the same as those in the chemical formula (II).

The perylene tetracarboxylic acid bisimide derivative according to the present invention is more preferably a perylene tetracarboxylic acid bisimide derivative represented by the following chemical formula (4) or (5), a tautomer or stereoisomer of the perylene tetracarboxylic acid bisimide

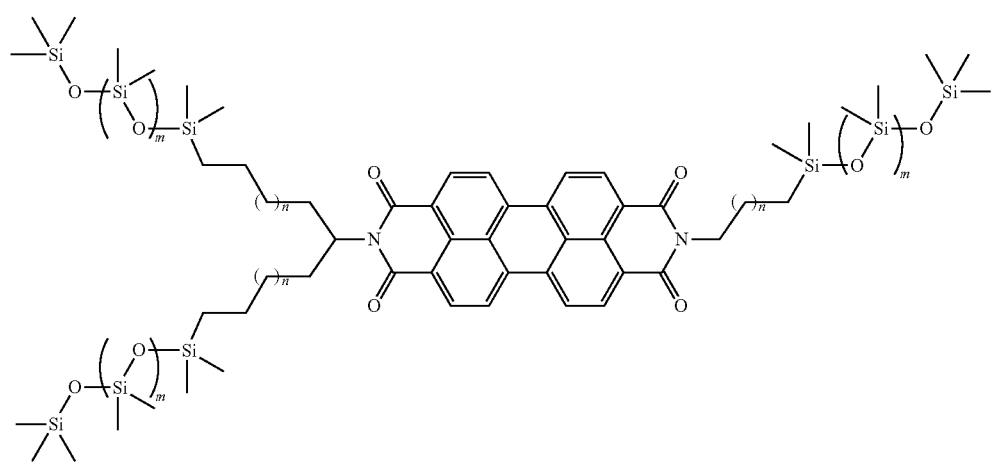

(3)

derivative, or a salt of the perylene tetracarboxylic acid bisimide derivative or the tautomer or stereoisomer.

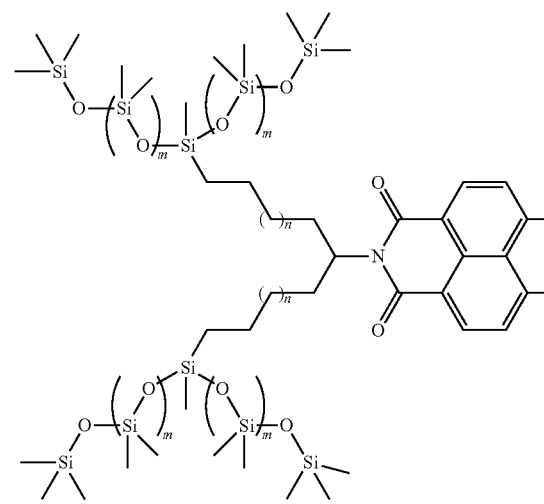

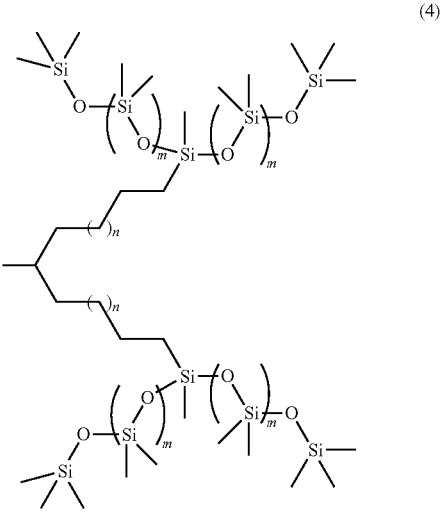

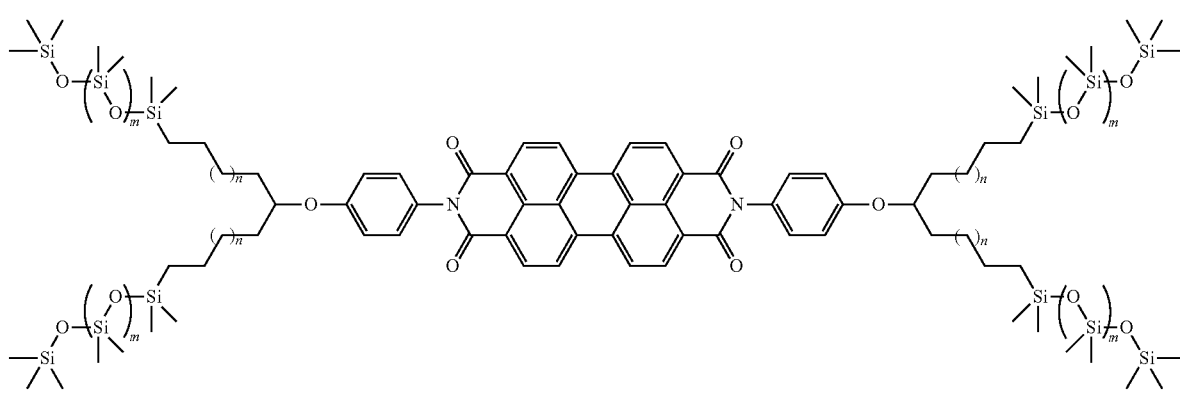

In the chemical formulae (4) and (5), m and n are the same as those in the chemical formula (II).

From the viewpoint of the ease of exhibiting liquid crystal properties, each m in the perylene tetracarboxylic acid bisimide derivative of the chemical formula (4) is more preferably an integer from 0 to 3. It can be said that the molecule of the chemical formula (4) has a structure in which each nitrogen atom of perylene tetracarboxylic acid bisimide is linked with each straight-chain organooligosiloxane group via a straight-chain alkylene group. Examples of the straight-chain alkylene group include a propylene group (n=1), a butylene group (n=2), a pentylene group (n=3), and a hexylene group (n=4), and the straight-chain alkylene group is particularly preferably a propylene group. Examples of the organo oligosiloxane group at each end include 1,1,1,3,5,5,5-heptamethyl trisiloxane (m=0), 1,1,1,3,3,5,7,7,9,9,9-undecamethyl pentasiloxane (m=1), 1,1,1,3,3,5,5,7,7,9,9,11,11,13,13,13-pentadecamethyl heptasiloxane (m=2), and 1,1,1,3,3,5,5,7,7,9,11,11,13,13,15,15,17,17,17-nonadecamethyl nonasiloxane (m=3), and the organooligosiloxane group is particularly preferably 1,1,1,3,5,5,5-heptamethyl trisiloxane (m=0) or 1,1,1,3,3,5,7,7,9,9,9-undecamethyl pentasiloxane (m=1).

From the viewpoint of the ease of exhibiting liquid crystal properties, each m in the perylene tetracarboxylic acid bisimide derivative of the chemical formula (5) is more preferably an integer from 0 to 6. It can be said that the molecule of the chemical formula (5) has a structure in which each nitrogen atom of perylene tetracarboxylic acid bisimide is linked with a methine group, and the methine group is linked with each straight-chain organooligosiloxane group via a straight-chain alkylene group. Examples of the straight-chain alkylene group include a propylene group (n=0), a butylene group (n=1), a pentylene group (n=2), and a hexylene group (n=3), and the straight-chain alkylene group is particularly preferably a propylene group. Examples of the organo oligosiloxane group at each end include 1,1,1,3,3,-pentamethyl disiloxane (m=0), 1,1,1,3,3,5,5-heptamethyl trisiloxane (m=1), 1,1,1,3,3,5,5,7,7-nonamethyl tetrasiloxane (m=2), and 1,1,1,3,3,5,5,7,7,9,9-undecamethyl pentasiloxane (m=3), and the organo oligosiloxane group is particularly preferably 1,1,1,3,3-pentamethyl disiloxane or 1,1,1,3,3,5,5-heptamethyl trisiloxane.

The perylene tetracarboxylic acid bisimide derivative represented by the chemical formula (4) may be, for example, the perylene tetracarboxylic acid bisimide derivative represented by the following chemical formula (4-1). The perylene tetracarboxylic acid bisimide derivative represented by the chemical formula (5) may be, for example, the perylene tetracarboxylic acid bisimide derivative represented by the following chemical formula (5-1). The following chemical formula (4-1) represents the case where each m is 0, and each n is 1 in the chemical formula (1). The following chemical formula (5-1) is the case where each m and each n are 1.

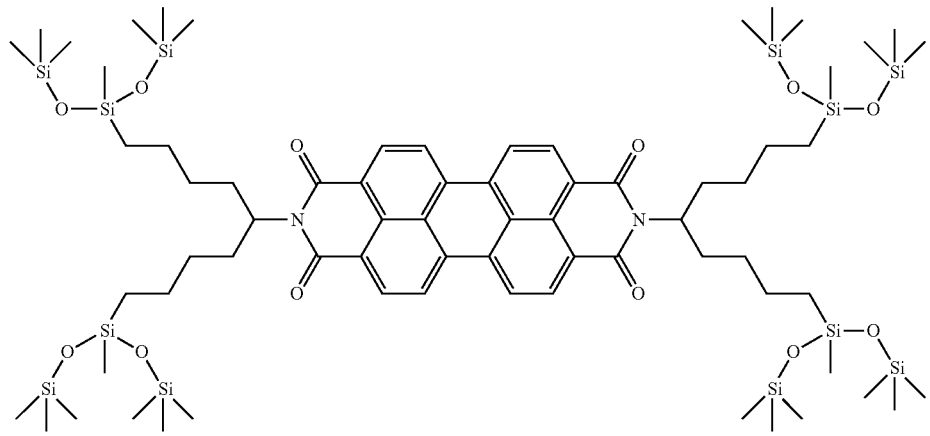

(4-1)

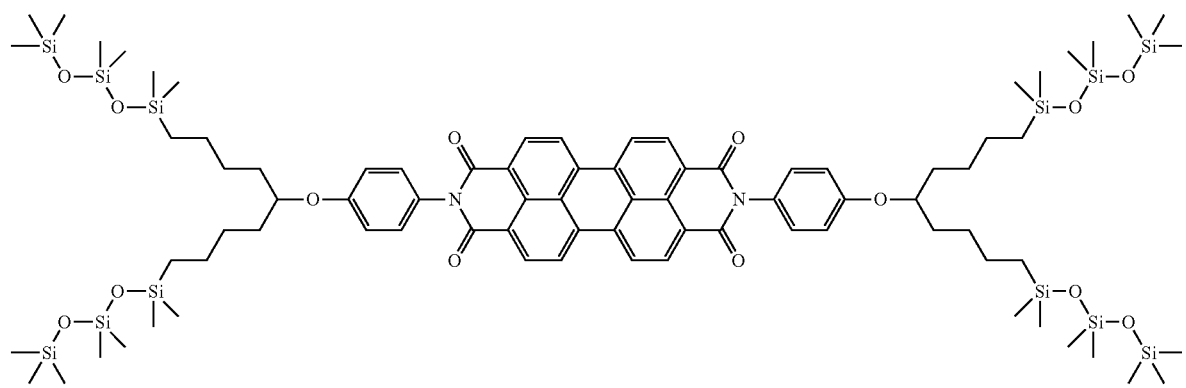

(5-1)

When the structure represented by the chemical formula (I) includes isomers such as a tautomer and a stereoisomer (e.g., a geometric isomer, an optical isomer), the structure of the compound according to the present invention may be the structure of any of these isomers. The compound according to the present invention also may be a perylene tetracarboxylic acid bisimide derivative represented by the chemical formula (I) or a salt of an isomer thereof. The salt may be an acid-added salt or a base-added salt. An acid forming the acid-added salt may be an inorganic acid or an organic acid, and a base forming the base-added salt may be an inorganic base or an organic base. The inorganic acid is not particularly limited, and examples thereof include sulfuric acid, phosphoric acid, hydrofluoric acid, a hydrochloric acid, hydrobromic acid, hydroiodic acid, hypofluorous acid, hypochlorous acid, hypobromous acid, hypoiodous acid, fluorous acid, chlorous acid, bromous acid, iodous acid, fluorine acid, chloric acid, bromic acid, iodine acid, perfluoric acid, perchloric acid, perbromic acid, and periodic acid. The organic acid is not particularly limited, and examples thereof include p-toluenesulfonic acid, methanesulfonic acid, oxalic acid, p-bromobenzenesulfonic acid, carbonic acid, succinic acid, citric acid, benzoic acid, acetic acid, hydroxycarboxylic acid, propionic acid, malonic acid, adipic acid, fumaric acid, and maleic acid. The inorganic base is not particularly limited, examples thereof include ammonium hydroxide, alkali metal hydroxide, alkaline-earth metal hydroxide, carbonate, bicarbonate, and sulfate, and specific examples thereof include sodium hydroxide, potassium hydroxide, potassium carbonate, sodium carbonate, sodium bicarbonate, potassium bicarbonate, calcium hydroxide, calcium carbonate, potassium sulfate, and calcium sulfate. The organic base is not particularly limited, and examples thereof include alcohol amine, trialkylamine, tetraalkylammonium, and tris(hydroxymethyl)aminomethane. The alcohol amine can be, for example, ethanolamine. Examples of trialkylamine include trimethylamine, triethylamine, tripropylamine, tributylamine, and trioctylamine. Examples of tetraalkylammonium include tetramethylammonium, tetraethylammonium, tetrapropylammonium, tetrabutylammonium, and tetraoctylammonium. A method for producing these salts also is not particularly limited, and these salts can be produced by a method in which the above-described acids and bases are added appropriately to the perylene tetracarboxylic acid bisimide derivative by a known method or the like, for example.

In the present invention, a chain group such as an alkyl group or an alkenyl group may be a straight-chain or branched group unless otherwise limited. In the present invention, specific examples of the alkyl group include a methyl group, an ethyl group, a n-propyl group, an isopropyl group, a n-butyl group, an isobutyl group, a sec-butyl group, a tert-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, and an icosyl group. The same applies to groups derived from the alkyl group (i.e., an alkylene group, an alkenyl group, an alkynyl group, a haloalkyl group, a hydroxyalkyl group, an aminoalkyl group, an alkanoyl group, an alkoxy group, an alkylamino group, a perfluoroalkyl group, an alkoxyalkyl group, and the like). In the present invention, an acyl group is not particularly limited, and examples thereof include a formyl group, an acetyl group, a propionyl group, an isobutyryl group, a valeryl group, an isovaleryl group, a pivaloyl group, a hexanoyl group, a cyclohexanoyl group, a benzoyl group, and an ethoxycarbonyl group. The same applies to groups having an acyl group in its structure (an acyloxy group, an alkanoyloxy group, and the like). In the present invention, the carbon number of acyl group includes the carbonyl carbon number, and for example, an alkanoyl group (acyl group) with a carbon number of 1 represents a formyl group. In the present invention, "halogen" is any halogen element, and examples thereof include fluorine, chlorine, bromine, and iodine.

Specific examples of the compound according to the present invention, represented by the chemical formula (1) or (2) other than the compounds represented by the chemical formulae (1-1) and (2-1) includes compounds shown in Table 1 (Tables 1-1 to 1-3) and Table 2 (Tables 2-1 to 2-3) below.

TABLE 1-1

Specific examples of compounds represented by chemical formula (1)

| Compound number | m | n |
|---|---|---|
| (1-2) | each m = 1 | each n = 0 |
| (1-3) | each m = 1 | each n = 2 |
| (1-4) | each m = 1 | each n = 3 |
| (1-5) | each m = 1 | each n = 4 |
| (1-6) | each m = 1 | each n = 5 |
| (1-7) | each m = 1 | each n = 6 |
| (1-8) | each m = 2 | each n = 0 |
| (1-9) | each m = 2 | each n = 1 |
| (1-10) | each m = 2 | each n = 2 |
| (1-11) | each m = 2 | each n = 3 |
| (1-12) | each m = 2 | each n = 4 |
| (1-13) | each m = 2 | each n = 5 |
| (1-14) | each m = 2 | each n = 6 |
| (1-15) | each m = 3 | each n = 0 |
| (1-16) | each m = 3 | each n = 1 |
| (1-17) | each m = 3 | each n = 2 |
| (1-18) | each m = 3 | each n = 3 |
| (1-19) | each m = 3 | each n = 4 |
| (1-20) | each m = 3 | each n = 5 |
| (1-21) | each m = 3 | each n = 6 |

TABLE 1-2

Specific examples of compounds represented by chemical formula (1)

| Compound number | m | n |
|---|---|---|
| (1-22) | each m = 4 | each n = 0 |
| (1-23) | each m = 4 | each n = 1 |
| (1-24) | each m = 4 | each n = 2 |
| (1-25) | each m = 4 | each n = 3 |
| (1-26) | each m = 4 | each n = 4 |
| (1-27) | each m = 4 | each n = 5 |
| (1-28) | each m = 4 | each n = 6 |
| (1-29) | each m = 5 | each n = 0 |
| (1-30) | each m = 5 | each n = 1 |
| (1-31) | each m = 5 | each n = 2 |
| (1-32) | each m = 5 | each n = 3 |
| (1-33) | each m = 5 | each n = 4 |
| (1-34) | each m = 5 | each n = 5 |
| (1-35) | each m = 5 | each n = 6 |
| (1-36) | each m = 6 | each n = 0 |
| (1-37) | each m = 6 | each n = 1 |
| (1-38) | each m = 6 | each n = 2 |

TABLE 1-2-continued

Specific examples of compounds represented by chemical formula (1)

| Compound number | m | n |
|---|---|---|
| (1-39) | each m = 6 | each n = 3 |
| (1-40) | each m = 6 | each n = 4 |
| (1-41) | each m = 6 | each n = 5 |
| (1-42) | each m = 6 | each n = 6 |

TABLE 1-3

Specific examples of compounds represented by chemical formula (1)

| Compound number | m | n |
|---|---|---|
| (1-43) | each m = 0 | each n = 0 |
| (1-44) | each m = 0 | each n = 1 |
| (1-45) | each m = 0 | each n = 2 |
| (1-46) | each m = 0 | each n = 3 |
| (1-47) | each m = 0 | each n = 4 |
| (1-48) | each m = 0 | each n = 5 |
| (1-49) | each m = 0 | each n = 6 |

TABLE 2-1

Specific examples of compounds represented by chemical formula (2)

| Compound number | m | n |
|---|---|---|
| (2-2) | each m = 1 | each n = 0 |
| (2-3) | each m = 1 | each n = 2 |
| (2-4) | each m = 1 | each n = 3 |
| (2-5) | each m = 1 | each n = 4 |
| (2-6) | each m = 1 | each n = 5 |
| (2-7) | each m = 1 | each n = 6 |
| (2-8) | each m = 2 | each n = 0 |
| (2-9) | each m = 2 | each n = 1 |
| (2-10) | each m = 2 | each n = 2 |
| (2-11) | each m = 2 | each n = 3 |
| (2-12) | each m = 2 | each n = 4 |
| (2-13) | each m = 2 | each n = 5 |
| (2-14) | each m = 2 | each n = 6 |
| (2-15) | each m = 3 | each n = 0 |
| (2-16) | each m = 3 | each n = 1 |
| (2-17) | each m = 3 | each n = 2 |
| (2-18) | each m = 3 | each n = 3 |
| (2-19) | each m = 3 | each n = 4 |
| (2-20) | each m = 3 | each n = 5 |
| (2-21) | each m = 3 | each n = 6 |

TABLE 2-2

Specific examples of compounds represented by chemical formula (2)

| Compound number | m | n |
|---|---|---|
| (2-22) | each m = 4 | each n = 0 |
| (2-23) | each m = 4 | each n = 1 |
| (2-24) | each m = 4 | each n = 2 |
| (2-25) | each m = 4 | each n = 3 |
| (2-26) | each m = 4 | each n = 4 |
| (2-27) | each m = 4 | each n = 5 |
| (2-28) | each m = 4 | each n = 6 |
| (2-29) | each m = 5 | each n = 0 |
| (2-30) | each m = 5 | each n = 1 |
| (2-31) | each m = 5 | each n = 2 |
| (2-32) | each m = 5 | each n = 3 |
| (2-33) | each m = 5 | each n = 4 |
| (2-34) | each m = 5 | each n = 5 |

TABLE 2-2-continued

Specific examples of compounds represented by chemical formula (2)

| Compound number | m | n |
|---|---|---|
| (2-35) | each m = 5 | each n = 6 |
| (2-36) | each m = 6 | each n = 0 |
| (2-37) | each m = 6 | each n = 1 |
| (2-38) | each m = 6 | each n = 2 |
| (2-39) | each m = 6 | each n = 3 |
| (2-40) | each m = 6 | each n = 4 |
| (2-41) | each m = 6 | each n = 5 |
| (2-42) | each m = 6 | each n = 6 |

TABLE 2-3

Specific examples of compounds represented by chemical formula (2)

| Compound number | m | n |
|---|---|---|
| (2-43) | each m = 0 | each n = 0 |
| (2-44) | each m = 0 | each n = 1 |
| (2-45) | each m = 0 | each n = 2 |
| (2-46) | each m = 0 | each n = 3 |
| (2-47) | each m = 0 | each n = 4 |
| (2-48) | each m = 0 | each n = 5 |
| (2-49) | each m = 0 | each n = 6 |

Specific examples of the compound according to the present invention, represented by the chemical formula (3) include compounds shown in Table 3 (Tables 3-1 to 3-3)

TABLE 3-1

Specific examples of compounds represented by chemical formula (3)

| Compound number | m | n |
|---|---|---|
| (3-1) | each m = 1 | each n = 0 |
| (3-2) | each m = 1 | each n = 1 |
| (3-3) | each m = 1 | each n = 2 |
| (3-4) | each m = 1 | each n = 3 |
| (3-5) | each m = 1 | each n = 4 |
| (3-6) | each m = 1 | each n = 5 |
| (3-7) | each m = 1 | each n = 6 |
| (3-8) | each m = 2 | each n = 0 |
| (3-9) | each m = 2 | each n = 1 |
| (3-10) | each m = 2 | each n = 2 |
| (3-11) | each m = 2 | each n = 3 |
| (3-12) | each m = 2 | each n = 4 |
| (3-13) | each m = 2 | each n = 5 |
| (3-14) | each m = 2 | each n = 6 |
| (3-15) | each m = 3 | each n = 0 |
| (3-16) | each m = 3 | each n = 1 |
| (3-17) | each m = 3 | each n = 2 |
| (3-18) | each m = 3 | each n = 3 |
| (3-19) | each m = 3 | each n = 4 |
| (3-20) | each m = 3 | each n = 5 |
| (3-21) | each m = 3 | each n = 6 |

TABLE 3-2

Specific examples of compounds represented by chemical formula (3)

| Compound number | m | n |
|---|---|---|
| (3-22) | each m = 4 | each n = 0 |
| (3-23) | each m = 4 | each n = 1 |
| (3-24) | each m = 4 | each n = 2 |
| (3-25) | each m = 4 | each n = 3 |

TABLE 3-2-continued

Specific examples of compounds represented by chemical formula (3)

| Compound number | m | n |
|---|---|---|
| (3-26) | each m = 4 | each n = 4 |
| (3-27) | each m = 4 | each n = 5 |
| (3-28) | each m = 4 | each n = 6 |
| (3-29) | each m = 5 | each n = 0 |
| (3-30) | each m = 5 | each n = 1 |
| (3-31) | each m = 5 | each n = 2 |
| (3-32) | each m = 5 | each n = 3 |
| (3-33) | each m = 5 | each n = 4 |
| (3-34) | each m = 5 | each n = 5 |
| (3-35) | each m = 5 | each n = 6 |
| (3-36) | each m = 6 | each n = 0 |
| (3-37) | each m = 6 | each n = 1 |
| (3-38) | each m = 6 | each n = 2 |
| (3-39) | each m = 6 | each n = 3 |
| (3-40) | each m = 6 | each n = 4 |
| (3-41) | each m = 6 | each n = 5 |
| (3-42) | each m = 6 | each n = 6 |

TABLE 3-3

Specific examples of compounds represented by chemical formula (3)

| Compound number | m | n |
|---|---|---|
| (3-43) | each m = 0 | each n = 0 |
| (3-44) | each m = 0 | each n = 1 |
| (3-45) | each m = 0 | each n = 2 |
| (3-46) | each m = 0 | each n = 3 |
| (3-47) | each m = 0 | each n = 4 |
| (3-48) | each m = 0 | each n = 5 |
| (3-49) | each m = 0 | each n = 6 |

Specific examples of the compound according to the present invention, represented by the chemical formula (4) include compounds shown in Table 4 (Tables 4-1 to 4-2) below.

TABLE 4-1

Specific examples of compounds represented by chemical formula (4)

| Compound number | m | n |
|---|---|---|
| (4-2) | each m = 0 | each n = 0 |
| (4-3) | each m = 0 | each n = 2 |
| (4-4) | each m = 0 | each n = 3 |
| (4-5) | each m = 0 | each n = 4 |
| (4-6) | each m = 0 | each n = 5 |
| (4-7) | each m = 0 | each n = 6 |
| (4-8) | each m = 1 | each n = 0 |
| (4-9) | each m = 1 | each n = 1 |
| (4-10) | each m = 1 | each n = 2 |
| (4-11) | each m = 1 | each n = 3 |
| (4-12) | each m = 1 | each n = 4 |
| (4-13) | each m = 1 | each n = 5 |
| (4-14) | each m = 1 | each n = 6 |
| (4-15) | each m = 2 | each n = 0 |
| (4-16) | each m = 2 | each n = 1 |
| (4-17) | each m = 2 | each n = 2 |
| (4-18) | each m = 2 | each n = 3 |
| (4-19) | each m = 2 | each n = 4 |
| (4-20) | each m = 2 | each n = 5 |
| (4-21) | each m = 2 | each n = 6 |
| (4-22) | each m = 3 | each n = 0 |
| (4-23) | each m = 3 | each n = 1 |
| (4-24) | each m = 3 | each n = 2 |
| (4-25) | each m = 3 | each n = 3 |

TABLE 4-2

Specific examples of compounds represented by chemical formula (4)

| Compound number | m | n |
|---|---|---|
| (4-26) | each m = 3 | each n = 4 |
| (4-27) | each m = 3 | each n = 5 |
| (4-28) | each m = 3 | each n = 6 |
| (4-29) | each m = 4 | each n = 0 |
| (4-30) | each m = 4 | each n = 1 |
| (4-31) | each m = 4 | each n = 2 |
| (4-32) | each m = 4 | each n = 3 |
| (4-33) | each m = 4 | each n = 4 |
| (4-34) | each m = 4 | each n = 5 |
| (4-35) | each m = 4 | each n = 6 |
| (4-36) | each m = 5 | each n = 0 |
| (4-37) | each m = 5 | each n = 1 |
| (4-38) | each m = 5 | each n = 2 |
| (4-39) | each m = 5 | each n = 3 |
| (4-40) | each m = 5 | each n = 4 |
| (4-41) | each m = 5 | each n = 5 |
| (4-42) | each m = 5 | each n = 6 |
| (4-43) | each m = 6 | each n = 0 |
| (4-44) | each m = 6 | each n = 1 |
| (4-45) | each m = 6 | each n = 2 |
| (4-46) | each m = 6 | each n = 3 |
| (4-47) | each m = 6 | each n = 4 |
| (4-48) | each m = 6 | each n = 5 |
| (4-49) | each m = 6 | each n = 6 |

Specific examples of the compound according to the present invention, represented by the chemical formula (5) include compounds shown in Table 5 (Tables 5-1 to 5-2).

TABLE 5-1

Specific examples of compounds represented by chemical formula (5)

| Compound number | m | n |
|---|---|---|
| (5-2) | each m = 0 | each n = 0 |
| (5-3) | each m = 0 | each n = 1 |
| (5-4) | each m = 0 | each n = 2 |
| (5-5) | each m = 0 | each n = 3 |
| (5-6) | each m = 0 | each n = 4 |
| (5-7) | each m = 0 | each n = 5 |
| (5-8) | each m = 0 | each n = 6 |
| (5-9) | each m = 1 | each n = 0 |
| (5-10) | each m = 1 | each n = 2 |
| (5-11) | each m = 1 | each n = 3 |
| (5-12) | each m = 1 | each n = 4 |
| (5-13) | each m = 1 | each n = 5 |
| (5-14) | each m = 1 | each n = 6 |

TABLE 5-1-continued

Specific examples of compounds represented by chemical formula (5)

| Compound number | m | n |
|---|---|---|
| (5-15) | each m = 2 | each n = 0 |
| (5-16) | each m = 2 | each n = 1 |
| (5-17) | each m = 2 | each n = 2 |
| (5-18) | each m = 2 | each n = 3 |
| (5-19) | each m = 2 | each n = 4 |
| (5-20) | each m = 2 | each n = 5 |
| (5-21) | each m = 2 | each n = 6 |
| (5-22) | each m = 3 | each n = 0 |
| (5-23) | each m = 3 | each n = 1 |
| (5-24) | each m = 3 | each n = 2 |
| (5-25) | each m = 3 | each n = 3 |

TABLE 5-2

Specific examples of compounds represented by chemical formula (5)

| Compound number | m | n |
|---|---|---|
| (5-26) | each m = 3 | each n = 4 |
| (5-27) | each m = 3 | each n = 5 |
| (5-28) | each m = 3 | each n = 6 |
| (5-29) | each m = 4 | each n = 0 |
| (5-30) | each m = 4 | each n = 1 |
| (5-31) | each m = 4 | each n = 2 |
| (5-32) | each m = 4 | each n = 3 |
| (5-33) | each m = 4 | each n = 4 |
| (5-34) | each m = 4 | each n = 5 |
| (5-35) | each m = 4 | each n = 6 |
| (5-36) | each m = 5 | each n = 0 |
| (5-37) | each m = 5 | each n = 1 |
| (5-38) | each m = 5 | each n = 2 |
| (5-39) | each m = 5 | each n = 3 |
| (5-40) | each m = 5 | each n = 4 |
| (5-41) | each m = 5 | each n = 5 |
| (5-42) | each m = 5 | each n = 6 |
| (5-43) | each m = 6 | each n = 0 |
| (5-44) | each m = 6 | each n = 1 |
| (5-45) | each m = 6 | each n = 2 |
| (5-46) | each m = 6 | each n = 3 |
| (5-47) | each m = 6 | each n = 4 |
| (5-48) | each m = 6 | each n = 5 |
| (5-49) | each m = 6 | each n = 6 |

Specific examples of the compound according to the present invention other than the compounds represented by the chemical formulae (1) to (5) include compounds shown in Table 6 below.

TABLE 6

Specific examples of compounds represented by chemical formula (I) other than compounds represented by chemical formulae (1) to (5) (In $R^7$ to $R^{10}$, "o" represents an ortho position of a carbonyl group (imide group), and "m" represents a meta position of a carbonyl group (imide group).)

| Compound number | $R^1$ $R^2$ $R^3$ $R^4$ $R^5$ $R^6$ | $R^7$ (o) | $R^7$ (m) | $R^8$ (o) | $R^8$ (m) | $R^8$ (o) | $R^8$ (m) | $R^{10}$ (o) | $R^{10}$ (m) |
|---|---|---|---|---|---|---|---|---|---|
| 101 | the same as those in compound (1-1) | methyl | none | methyl | none | methyl | none | methyl | none |
| 102 | the same as those in compound (2-1) | methyl | none | methyl | none | methyl | none | methyl | none |
| 103 | the same as those in compound (1-1) | fluorine | fluorine | fluorine | fluorine | fluorine | fluorine | fluorine | fluorine |
| 104 | the same those in compound (2-1) | fluorine | fluorine | fluorine | fluorine | fluorine | fluorine | fluorine | fluorine |

From the viewpoint of the ease of using the compound according to the present invention as an n-type semiconductor, the compound according to the present invention is preferably a liquid crystalline compound. In the present invention, "the liquid crystalline compound" is a compound having properties of being capable of exhibiting a liquid crystal phase (being in a form of a liquid crystal phase). Hereinafter, the compound according to the present invention being a liquid crystalline compound is also referred to as a "liquid crystalline compound according to the present invention". Although the temperature at which the liquid crystalline compound according to the present invention exhibits a liquid crystal phase is not particularly limited, it is preferred that the liquid crystalline compound exhibits a liquid crystal phase at room temperature or around room temperature from the viewpoint of the ease of using the liquid crystalline compound according to the present invention as an n-type semiconductor. In the present invention, "room temperature" is not particularly limited and is, for example, from −10° C. to 60° C., preferably from 0° C. to 50° C., more preferably from 10° C. to 45° C., yet more preferably from 15° C. to 40° C., particularly preferably from 20° C. to 40° C.

Perylene tetracarboxylic acid bisimide derivatives, each of which has a plurality of alkyl chains introduced thereinto and exhibits a liquid crystal phase, are known. However, many of them exhibit a liquid crystal phase at high temperature and are crystallized at room temperature. Moreover, there is a limited number of compounds whose electronic physical properties such as carrier mobility and photoconductivity have been evaluated clearly (Non-Patent Document 17). It is preferred that the liquid crystalline compound according to the present invention exhibits a liquid crystal phase in a temperature region which is lower than the temperature region in which known perylene tetracarboxylic acid derivatives and perylene tetracarboxylic acid imide derivatives exhibit a liquid crystal phase, for example. The liquid crystalline compound according to the present invention can exhibit a liquid crystal phase at room temperature, for example. Such effect in the liquid crystalline compound according to the present invention can be obtained by having a side chain that has an organooligosiloxane group and appropriately setting the length of the side chain (e.g., m and n in the chemical formula (II)), for example. There are only a few or a limited number of materials that can exhibit a liquid crystal phase at room temperature among not only n-type organic semiconductors but also general electron transport materials. The liquid crystalline compound according to the present invention exhibits a liquid crystal phase at room temperature, so that the liquid crystalline compound possesses really favorable electron transport properties at room temperature or around room temperature, for example. This means that the ease of using the liquid crystalline compound as an electron transport material is highly superior, which is an advantageous effect difficult to be expected from known art. Moreover, for example, it is possible to change the temperature at which a liquid crystal phase is exhibited to not only room temperature but also an appropriate temperature by changing the length of the side chain having an organooligosiloxane group. Note here that this description, however, is a mere example and does not limit the compound according to the present invention.

A method for producing the compound according to the present invention is not particularly limited and can be any method. The compound represented by the chemical formula (1) or (2) can be synthesized (produced) easily by refluxing appropriate perylene tetracarboxylic acid bis(ω-alkenylimide) or perylene tetracarboxylic acid bis(ω,ω-alkadienyl imide) and appropriate oligosiloxane in toluene in the presence of a Karstedt catalyst, for example. The Karstedt catalyst is, for example, a catalyst obtained by coordinating platinum with vinylsiloxane. The Karstedt catalyst can be prepared from $H_2PtCl_6$ and vinylsiloxane, for example. More specifically, the compound represented by the chemical formula (1) can be synthesized according to the following scheme 1, for example, and the compound represented by the chemical formula (2) can be synthesized by the following scheme 2, for example. In the following scheme 1, for example, perylene tetracarboxylic acid bis(allylimide) (compound (6), m=1, n=1) and 1,1,1,3,3,5,5-heptamethyl trisiloxane are heated in toluene preferably in the presence of a Karstedt catalyst. Thereafter the solvent is distilled off, and then, the crude product thus obtained is purified by a silica gel column chromatography (eluent: dichloromethane) and re-precipitation with methanol. Thus, the intended perylene tetracarboxylic acid bis(1,1,1,3,3,5,5-heptamethyltrisiloxanyl propylimide) (compound (1), m=1, n=1) can be obtained. In the following scheme 2, for example, perylene tetracarboxylic acid bis(1,8-nonadiene-5-ylimide) (compound (10), m=1, n=1) and 1,1,1,3,3,5,5-heptamethyl trisiloxane are heated in toluene in the presence of a Karstedt catalyst, and thereafter, a purification is performed in the same manner as in the scheme 1. Thus, perylene tetracarboxylic acid bis{di-(1,1,1,3,3,5,5-heptamethyl trisiloxanyl butyl)-methylimide}(compound (2), m=1, n=1) can be obtained. Perylene tetracarboxylic acid bis(allylimide) (compound (6), m=1, n=1) as a starting material can be obtained by heating perylene tetracarboxylic acid anhydride (PTCDA) and allylamine in quinolone in the presence of zinc acetate (the following scheme 1). Perylene tetracarboxylic acid bis(1,8-nonadiene-5-ylimide) (compound (10), m=1, n=1) as a starting material can be obtained in the same manner as for the compound (6) except that 1,8-nonadiene-5-ylamine (compound (9), m=1, n=1) is used as substitute for allylamine (the following scheme 2). In the scheme 2, "DEAD" represents diethyl azodicarboxylate. The same applies hereinafter. The case where m=1 and n=1 is described above, and also in the case where m and n are numeral values other than 1, a synthesis can be performed according to the above-described method. The reaction conditions such as a reaction temperature and a reaction time are not particularly limited. The above-described reaction conditions can be set or changed as appropriate with reference to the examples described below, a known similar reaction, and the like, for example. The reaction solvent also is not limited by the description and can be changed as appropriate.

Scheme 1

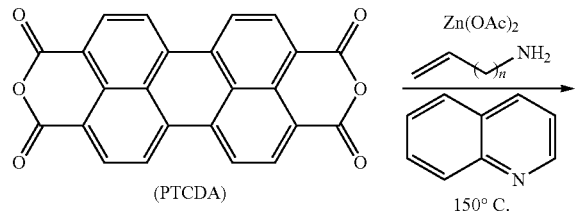

(PTCDA)

-continued
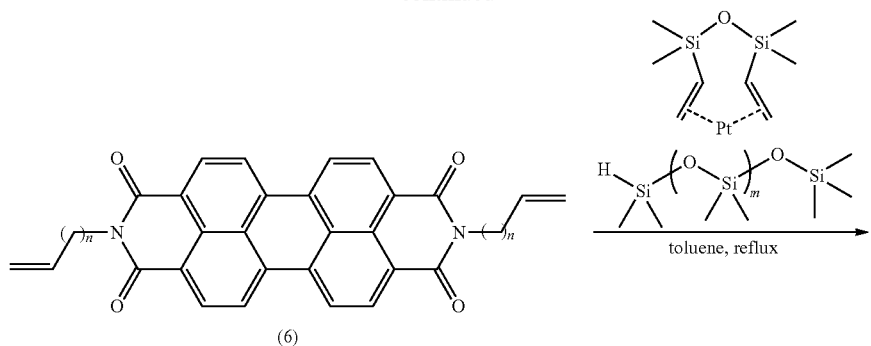
(6)
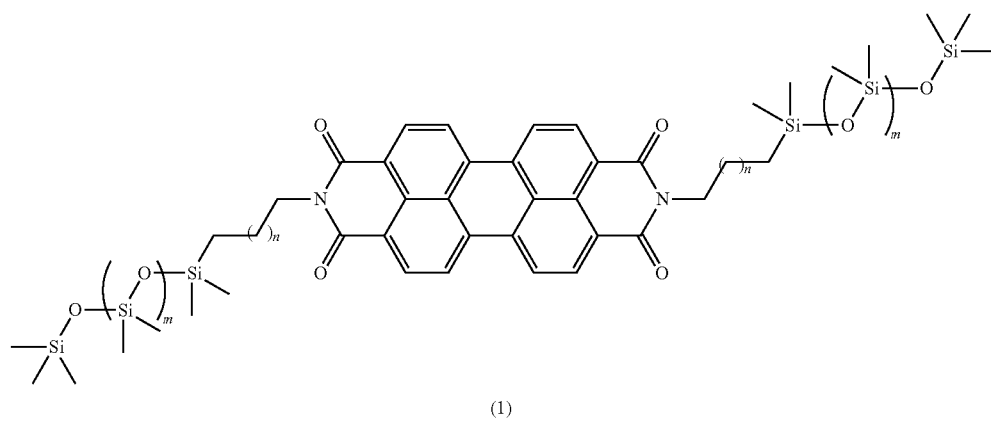
(1)
Scheme 2
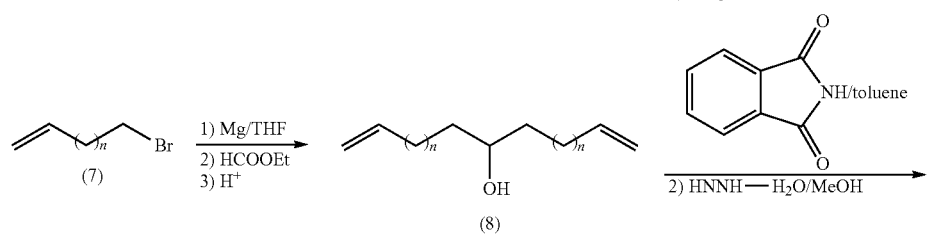
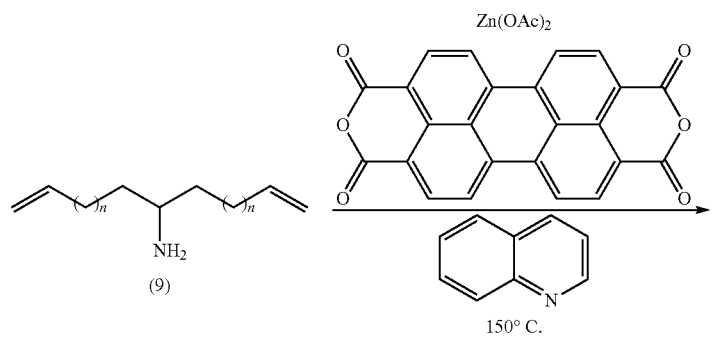

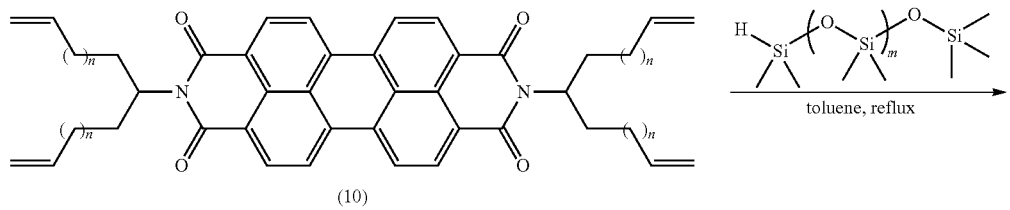

(10)

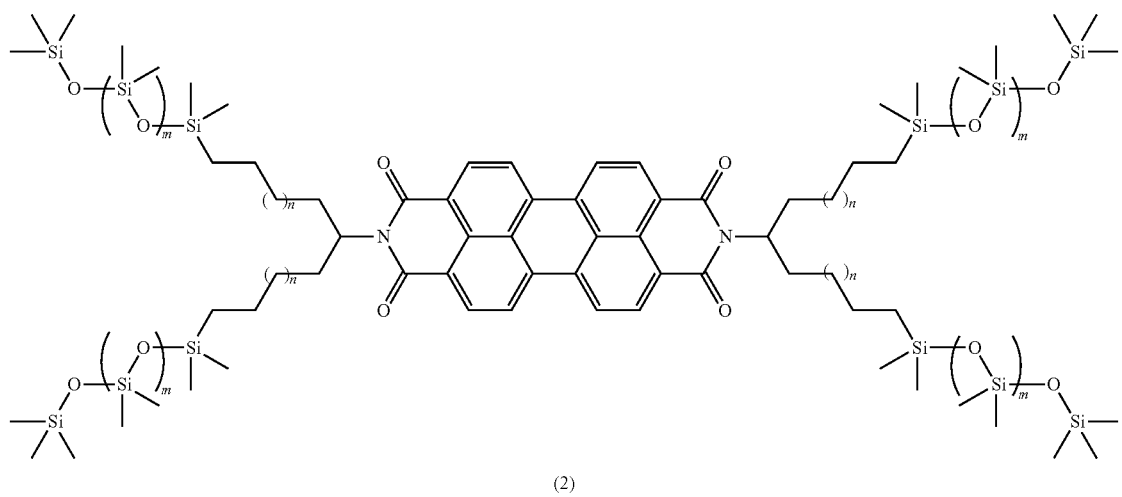

(2)

As mentioned above, it is difficult to synthesize a skeleton of an n-type organic semiconductor. For example, in the case of a fullerene derivative, it is difficult to selectively introduce a side chain into only an intended position, and the number of production steps is increased in many cases. In contrast, the compound according to the present invention can be synthesized by only two steps in the scheme 1 and four steps in the scheme 2. Moreover, each step in the schemes 1 and 2 can be performed without using a costly reagent, a dangerous reagent, an intense reaction condition, and the like. For example, perylene tetracarboxylic acid anhydride (PTCDA) as a starting material in the schemes 1 and 2 is really inexpensive compared with fullerene. The yields in the reactions according to the schemes 1 and 2 are high as shown in the examples described below, for example. Thus, according to the scheme 1 and 2, syntheses can be performed easily at low cost. In the compound according to the present invention, the compound represented by the chemical formula (1) or (2) is particularly superior from the viewpoint of physical properties further suitable for an n-type organic semiconductor and the ease of synthesizing (producing) the compound. Among them, the compound represented by the chemical formula (2) is particularly superior from the viewpoint of suitability (e.g., conductivity, liquid crystal properties, and the like) as an n-type organic semiconductor, and the compound represented by the chemical formula (1) is particularly superior in the point of being capable of synthesizing the compound easily at low cost.

A method for synthesizing (producing) the compound according to the present invention, represented by the chemical formula (1) or (2), is not limited to the schemes 1 and 2 and can be any method. The compound according to the present invention, represented by the chemical formula (3) may be synthesized by a combination of the schemes 1 and 2 or any method, for example.

A method for synthesizing (producing) the compound according to the present invention, represented by the chemical formula (4) is not particularly limited, and the compound can be synthesized by a method of the following scheme 3, for example. In the scheme 3, a method for synthesizing a compound (10) is not shown, and the compound (10) may be synthesized by the same synthesis method as in the scheme 2, for example. A coupling reaction of the compound (10) and siloxane in the presence of a Karstedt catalyst may be performed in the same manner as in the scheme 2 except that siloxane is changed to siloxane appropriate for a compound (4). That is, the compound (4) according to the present invention can be synthesized easily at low cost as in the synthesis of the compound (2).

Scheme 3

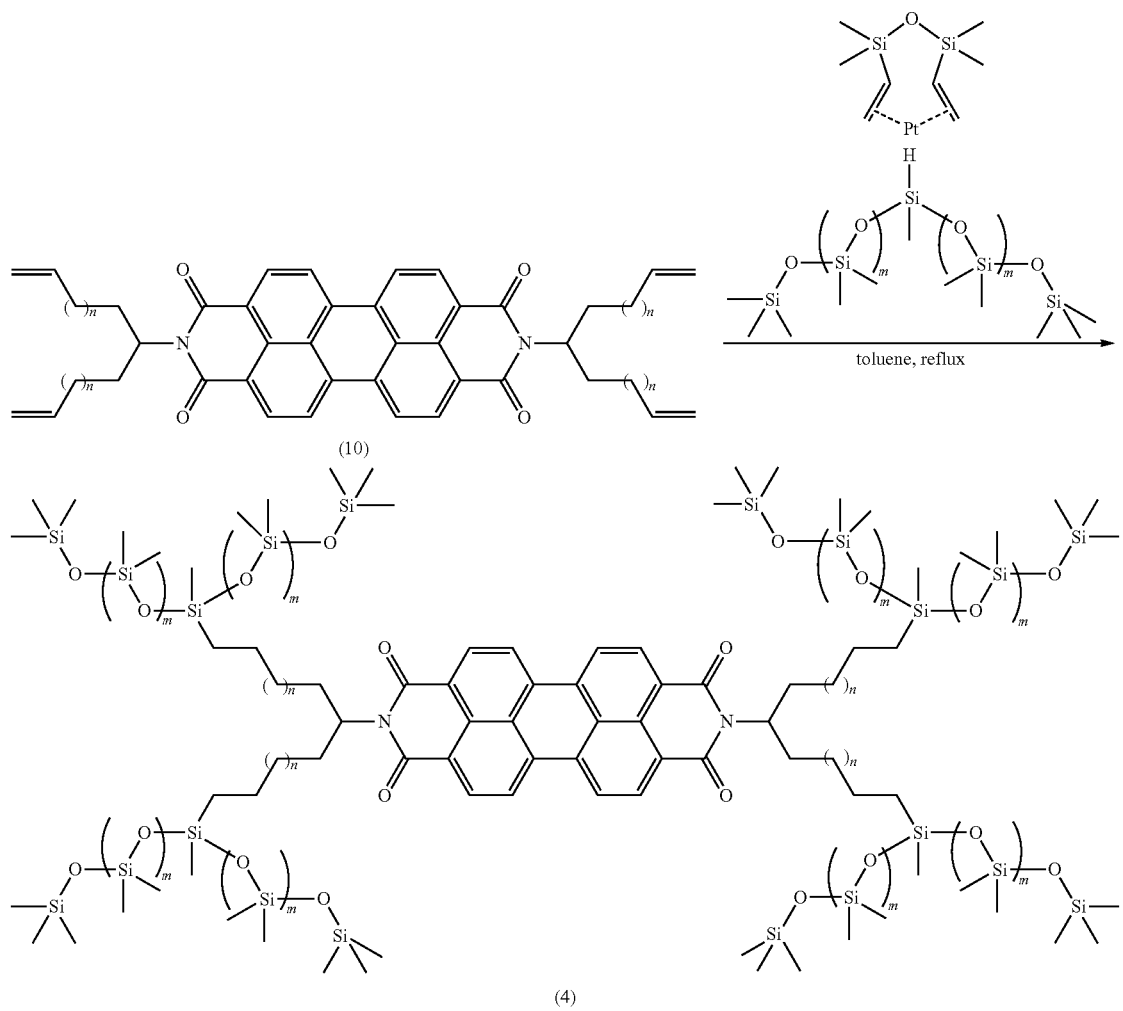

A method for synthesizing (producing) the compound according to the present invention, represented by the chemical formula (5) also is not particularly limited, and the compound can be produced by a method of the following scheme 4, for example. As shown in the scheme 4, a compound (5) can be synthesized in the same manner as in the scheme 2 except that the following compound (12) is used as an intermediate material instead of the compound (9). A method for synthesizing the compound (12) also is not particularly limited, and the compound (12) may be synthesized by synthesizing a compound (8) in the same manner as in the scheme 2, subjecting the compound (8) and p-nitrophenol to a coupling reaction in the presence of triphenylphosphine and DEAD to produce a compound (11), and further reducing a nitro group of the compound (11) with an iron powder, as shown in the scheme 4 below, for example. That is, the compound (5) according to the present invention can be synthesized easily at low cost in almost the same number of steps as in the scheme 2, which is a synthesis scheme of the compound (2), without a costly reagent, a dangerous reagent, intense reaction conditions and the like.

Scheme 4

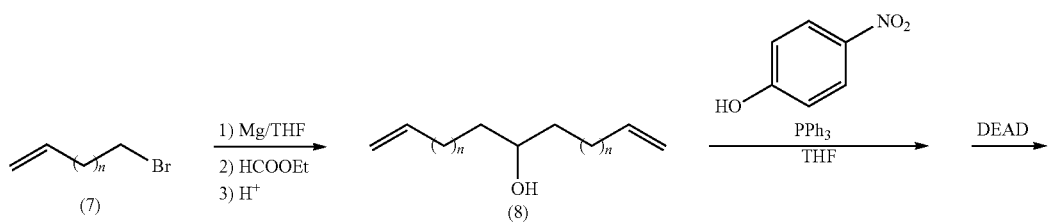

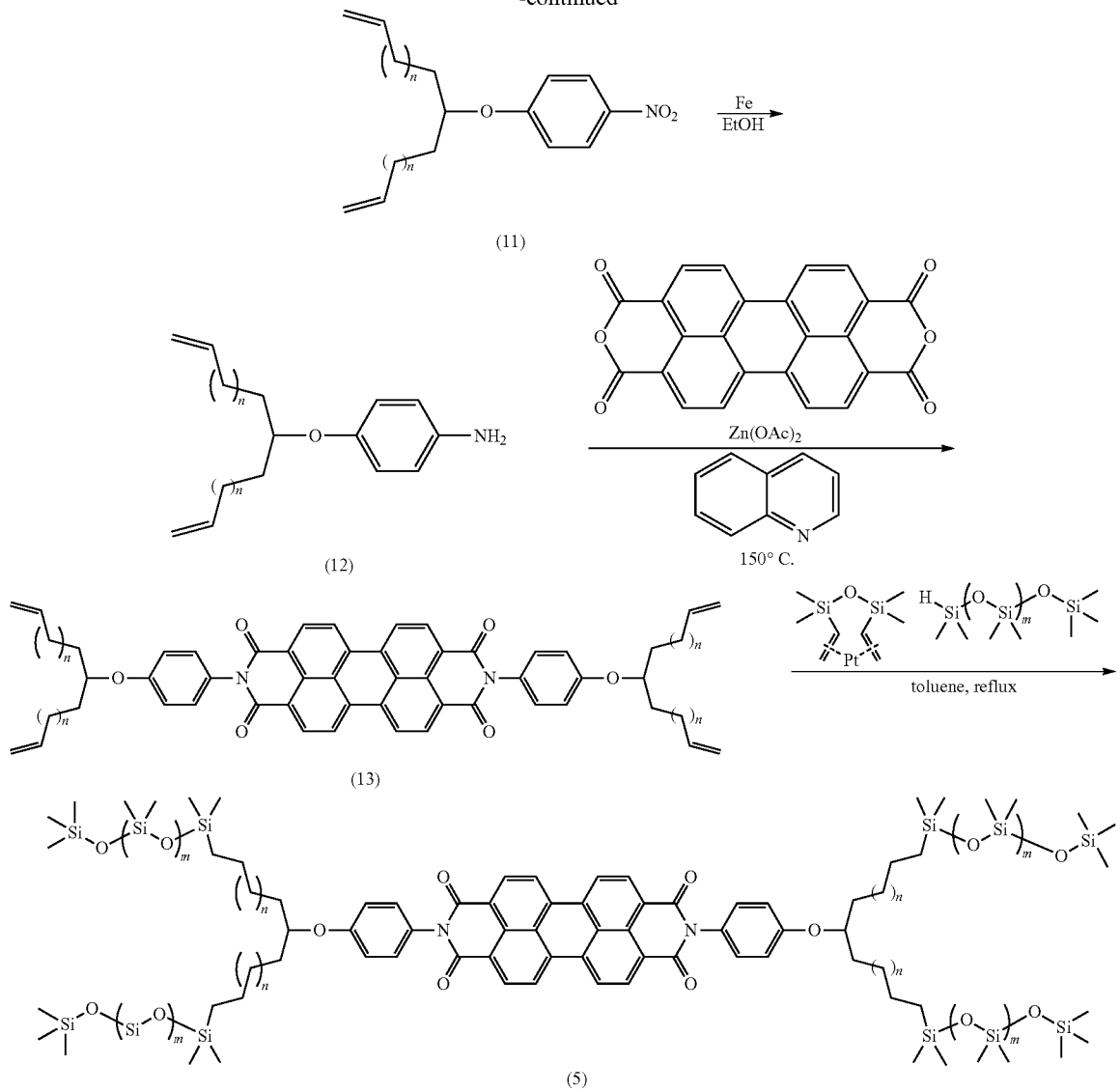

The method for synthesizing (producing) the compound according to the present invention, represented by the chemical formula (4) or (5) is not limited to the scheme 3 and 4 and can be any method.

A method for synthesizing the compound according to the present invention, represented by a chemical formula other than the chemical formulae (1) to (5) also is not particularly limited as described above. For example, in the case of a compound where structures of linking groups $L^1$ and $L^2$ in the chemical formula (I) are different from those of the compound (5), the compound may be synthesized in the same manner as in the scheme 4 except that p-nitrophenol or the compound (11) in the scheme 4 is changed to a compound appropriate for the structures of the linking groups $L^1$ and $L^2$ or by any method.

[n-Type Semiconductor and Method for Producing the Same]

Next, an n-type semiconductor according to the present invention and a method for producing the same are described.

The n-type semiconductor according to the present invention includes, as mentioned above, the perylene tetracarboxylic acid bisimide derivative according to the present invention, a tautomer or stereoisomer of the perylene tetracarboxylic acid bisimide derivative, or a salt of the perylene tetracarboxylic acid bisimide derivative or the tautomer or stereoisomer. As mentioned above, the compound according to the present invention has high electron mobility (carrier mobility), so that the compound is favorably used in an n-type semiconductor. Other configurations of the n-type semiconductor according to the present invention are not particularly limited, and the n-type semiconductor may or may not include other components as appropriate besides the compound according to the present invention. The other components are not particularly limited, and examples thereof include dialkyl perylene tetracarboxylic acid diimide and perylene tetracarboxylic acid ester.

A method for producing the n-type semiconductor according to the present invention is not particularly limited, and it is preferred that the n-type semiconductor is produced by the production method according to the present invention, i.e., so-called coating method. The coating method is advantageous in that large-size facilities such as an ultra-high vacuum device and the like are not required for single crystallization, thinning of a film, and the like, resulting in low cost, and it is possible to produce a large-area thin film (n-type semiconductor) compared with a vacuum process.

As mentioned above, the production method according to the present invention is a method for producing an n-type semiconductor according to the present invention, including a solution preparation step of dissolving the perylene tetracarboxylic acid bisimide derivative according to the present invention, a tautomer or stereoisomer of the perylene tetracarboxylic acid bisimide derivative, or a salt of the perylene tetracarboxylic acid bisimide derivative or the tautomer or stereoisomer in a solvent to prepare a solution, a coating step of coating a base with the solution to form a coating film, and a drying step of drying the coating film. Other conditions in the production method according to the present invention are not particularly limited and can be selected as appropriate with reference to the conditions in production of known semiconductors by a coating method and the like, for example.

In the solution preparation step, a solvent is not particularly limited, and a solvent that can dissolve the compound according to the present invention can be selected as appropriate. Examples of the solvent include water, an organic solvent, and a mixed solvent of water and an organic solvent. Examples of the organic solvent include an aromatic solvent (e.g., toluene, chlorobenzene), ether (e.g., diethylether, tetrahydrofuran), a halogenated solvent (e.g., chloroform, dichloromethane), ester (e.g., ethylacetate), ketone (e.g., acetone), and hydrocarbon (e.g., cyclohexane, pentane, hexane), and they can be used alone or in a combination of two or more of them. In the coating step, a coating method is not particularly limited, and examples thereof include a spin coating method, a casting method, a blade coating method, a Czochralski method, and a zone casting method. Conditions in the coating step are not particularly limited and can be selected as appropriate with reference to the production conditions in the examples described below, the conditions in production of known semiconductors by a coating method, and the like, for example. The temperature, the drying time, and the like in the drying step also are not particularly limited and can be selected as appropriate with reference to the production conditions in the examples described below, the conditions in production of known semiconductors by a coating method, and the like, for example.

The use of the n-type semiconductor according to the present invention is not particularly limited, and examples thereof include a laser pigment and a photoconductor. For example, the compound according to the present invention has an absorption band in a visible light region, so that the n-type semiconductor according to the present invention is favorable as a pigment, for example. Moreover, the compound according to the present invention is superior in photoconductivity, so that the n-type semiconductor according to the present invention is favorable as a photoconductor, for example. The photoconductor can be used in a solar battery, for example. An optical spectrum and physical properties such as electric properties of the compound or n-type semiconductor according to the present invention are shown in the examples described below, for example, and are, however, not limited thereto.

[Electronic Device]

As mentioned above, the electronic device according to the present invention includes the n-type semiconductor according to the present invention. Other configurations of the electronic device according to the present invention are not particularly limited. In the present invention, "electronic device" means a general device which is activated or operated by electricity. Specifically, for example, the electronic device according to the present invention includes an electronic element and electronic equipment including the electronic element. Examples of the electronic device according to the present invention include a battery, a solar battery, a laser, an organic EL device, an electroluminescence element, a transistor, and a memory element. The electronic device according to the present invention may be, for example, an organic thin-film solar battery, an organic electroluminescence element, an organic thin-film transistor (TFT), or the like. The form of use of the n-type semiconductor according to the present invention in the electronic device according to the present invention is not particularly limited and may be the same as that of the conventional n-type semiconductor, for example. Further, for example, the n-type semiconductor according to the present invention can be used in an appropriate electronic device according to the properties thereof. Specifically, for example, the n-type semiconductor according to the present invention is superior in photoconductivity and is thus suitable in a solar battery. Furthermore, for example, the n-type semiconductor according to the present invention has an absorption band in a visible light region and is thus suitable to be used in a visible light laser. Research on n-type organic semiconductors has been barely promoted compared with research on p-type organic semiconductors. However, according to the present invention, an n-type organic semiconductor having favorable properties such as high carrier mobility and the like can be provided. Thus, by using the n-type semiconductor (n-type organic semiconductor) according to the present invention in combination with a p-type semiconductor such as a p-type organic semiconductor, for example, an electronic device having superior performance can be provided.

EXAMPLES

Next, the present invention is described in further detail with reference to the examples. The present invention, however, is not limited by the following examples.

[Measurement Conditions and the Like]

All chemical substances were reagent-grade chemical substances and were purchased from Tokyo Chemical Industry Co., Ltd. or Wako Pure Chemical Industries, Ltd. As reagents and solvents used in synthesis, commercially available products were used without purifying them. As dried reagents described as reaction solvents, commercially available dehydrated solvents were used. The progress of each reaction was checked by thin-layer chromatography (TLC). In TLC, 0.25 mm-E Merck silica gel plates (silica Gel F254) were used, and a UV lamp (254 nm, 365 nm) and iodine were used in combination in spot detection according to the compound. In purification by silica gel column chromatography, Kanto Chemical silica gel 60 (Silica Gel 60, spherical, 40 to 50 μm) was used. $^1$H-NMR measurement was performed by a device manufactured by Varian, Inc., a nuclear magnetic resonance spectrometer (trade name: Varian UNITY LNOVA400NB, 400 MHz in $^1$H-NMR measurement, 100 MHz in $^{13}$C-NMR measurement). Infrared absorption spectrum (1R) measurement was performed by SPECTRUM 100 (FT-IR Spectrometer) manufactured by Perkin Elmer, Inc. Mass spectrometry was performed by a device (trade name: AUFOFLEX-K) manufactured by Bruker Daltonics K. K. In observation of liquid crystal phase and thin film by a microscope (polarization microscope, POM), a device manufactured by OLYMPUS CORPORATION (trade name: Olympus BX53) was used. XRD (X-ray diffraction) measurement was performed by R-AXIS RAPID II manufactured by Rigaku Corporation.

A spin coating method was performed by a device (trade name: 1H-DX2) manufactured by MIKASA SANGYO CO., LTD. Ultraviolet-visible absorption spectrum (UV-Vis. spectrum) measurement was performed by a device (trade name: UV-3150) manufactured by Shimadzu Corporation. Measurement by cyclic voltammetry was performed by a device (trade name: Potentio stat 600B) manufactured by BAS Inc. Measurement of charge transport properties (carrier mobility properties) by a Time-of-Flight method was performed by a combined use of oscilloscope (trade name: TDS 3044B) manufactured by TEXTRONIX INC., Nd: YAGlaser (trade name: minlight I) manufactured by Continuum, Inc., an electrometer (trade name: R8252) manufactured by Advantest Corporation, and a self-made hot stage. Fluorescence spectrum measurements of the compounds (1-1) and (2-2) were performed by a device (trade name: RF5300-PC) manufactured by Shimadzu Corporation. Fluorescence spectrum measurements of the compounds (2-44), (2-46), (4-1), and (5-1) were performed by spectrofluorophotometer (Hitachi F-2500) at an excitation wavelength of 470 nm.

In the following examples, perylene tetracarboxylic acid imide derivatives (1-1) (in the chemical formula (I), m=1, n=1), (2-1) (in the chemical formula (2), m=1, n=1), (2-44) (in the chemical formula (2), m=0, n=1), and (2-46) (in the chemical formula (2), m=0, n=3) were synthesized according to the scheme 1 or 2. Further, a perylene tetracarboxylic acid imide derivative (4-1) (in the chemical formula (4), m=0, n=1) was synthesized according to the scheme 3, and a perylene tetracarboxylic acid imide derivative (5-1) (in the chemical formula (5), m=1, n=1) was synthesized according to the scheme 4. Furthermore, liquid crystal cells and n-type semiconductors were produced using these perylene tetracarboxylic acid imide derivatives, and ultraviolet-visible absorption spectra, reduction potentials, charge transport properties, and fluorescence spectra thereof were measured.

Reference Example 1

Synthesis of perylene tetracarboxylic acid bis(allylimide) (Compound (6), m=1, n=1)

4.12 g (10 mmol) of perylene tetracarboxylic acid anhydride (PTCDA) and 2.01 g (11 mmol) of anhydrous zinc acetate were suspended in 50 ml of quinolone. 1.18 g (21 mmol) of allylamine was added to a resultant suspension, which was then heated at 120° C. for 5 hours. This reaction solution thus obtained was cooled, and diluted hydrochloric acid was added thereto, and a resultant solution was filtered to obtain a reddish brown precipitate. The precipitate thus obtained was washed with diluted hydrochloric acid, water, and methanol in this order and dried. Thus, 4.82 g (10.3 mol) of a red powder was obtained as an intended compound (6). A yield of the compound (6) was 98%. The compound (6) was barely dissolved in an organic solvent and thus was used in a subsequent reaction without purifying. IR spectrum values of the compound (6) are shown below.

Compound (6):
IR (ATR): v=1691, 1653, 1589, 1333, 1242, 1172, 987, 898, 851, 809, 748 cm$^{-1}$;

Reference Example 2

Synthesis of 1,8-nonadiene-5-ylamine (Compound (9), m=1, n=1)

9.21 g (35 mmol) of triphenylphosphine, 4.50 g (32 mmol) of 1,8-nonadiene-5-ol (8), and 6.03 g (41 mmol) of phthalimide were dissolved in 150 ml of tetrahydrofuran. This solution thus obtained was stirred for 30 minutes, and at room temperature, 15 ml (33 mmol) of diethyl azodicarboxylate (2.2 mol/l solution in toluene) was thereafter dropped in the solution, which was then stirred for 12 hours. Subsequently, hexane was added to the solution, and a precipitate was filtered off, and the filtrate thus obtained was dried over sodium sulfate. The solvent was distilled off, and the crude product thus obtained was purified by silica gel column chromatography (eluent: hexane:ethyl acetate of 5:1). The product thus obtained was dissolved in 50 ml of methanol, and 3 ml of hydrazine hydrate was added to the solution thus obtained, which was then refluxed for 1 hour. The reaction solution thus obtained was cooled, and a white precipitate was obtained by filtration and was washed with methanol. The filtrate thus obtained was concentrated, hexane was then added to the filtrate, and a white precipitate thus produced was obtained by re-filtration and was washed with hexane. Then, the solvent was distilled off from this filtrate. Thus, 2.58 g (18 mmol) of a slightly yellow liquid was obtained as an intended compound (9). A yield of the compound (9) was 57%. 1,8-nonadiene-5-ol (8) as a synthetic starting material can be synthesized in the same manner as in Reference Example 8 (synthesis of starting material for Example 13) described below, for example. Values obtained by instrumental analysis of the compound (9) are shown below.

Compound (9):
$^1$H NMR (400 MHz, CDCl$_3$): δ=5.80 (ddt, 1H, J=16.8, 10.4, 6.4 Hz), 5.01 (tdd, 2H, J=16.8, 3.6, 1.6 Hz), 4.93 (ddt, 2H, J=10.4, 3.6, 1.2 Hz), 2.72 (tt, 1H, J=7.6, 4.8 Hz), 2.21-2.01 (m, 4H), 1.55-1.45 (m, 2H), 1.55-1.45 (m, 2H), 1.41-1.20 (4H, m); $^{13}$C NMR (100 MHz CDCl$_3$): δ=30.7, 37.4, 50.7, 114.7, 138.8; IR (ATR): v=3323, 3077, 2915, 2846, 1640, 1481, 1449, 1304, 1046, 993, 906, 638, 556 cm$^{-1}$; Exact Mass: 139.14 for C$_9$H$_{17}$N: m/z: [M+]139.3

Reference Example 3

Synthesis of perylene tetracarboxylic acid bis(1,8-nonadiene-5-ylimide) (Compound (10), m=1, n=1)

2.05 g (5.2 mmol) of perylene tetracarboxylic acid anhydride (PTCDA) and 1.09 g (5.9 mmol) of anhydrous zinc acetate were suspended in 30 ml of quinolone. 1.52 g (10.8 mmol) of 1,8-nonadiene-5-ylamine (9) was added to a resultant suspension, which was then heated at 120° C. for 5 hours. The reaction solution thus obtained was cooled, 20% hydrochloric acid was added thereto, a resultant solution was filtered to obtain the reddish brown precipitate thus obtained, and the precipitate was washed with diluted hydrochloric acid. The precipitate thus obtained was purified by silica gel column chromatography (eluent: dichloromethane). The crude product thus obtained was dissolved in dichloromethane and was then re-precipitated with ethyl acetate. Thus, 2.060 g (3.2 mmol) of a red powder was obtained as an intended compound (10). A yield of the compound (10) was 62%. Values obtained by instrumental analysis of the compound (10) are shown below.

Compound (10):
$^1$H NMR (400 MHz, CDCl$_3$): δ=8.66 (d, 4H, br), 8.62 (dd, 4H, J=8.0 Hz), 5.79 (ddt, 4H, J=16.8, 10.4, 6.4 Hz), 5.23 (tt, 2H, J=6.8, 5.2 Hz), 4.96 (dd, 4H, J=16.8, 3.6 Hz), 4.88 (dd, 4H, J=10.0, 3.6 Hz), 2.36-2.44 (m, 4H), 2.01-2.14 (m, 8H), 1.91-2.01 (m, 4H); $^{13}$C NMR (100 MHz CDCl$_3$): δ=31.3, 31.6, 53.8, 115.1, 123.3, 126.7, 129.8, 134.8, 138.1, 197.9; IR (ATR): v=3077, 2972, 1692, 1650, 1593, 1405, 13851247, 1173, 908, 809, 746, 619, 430, 395 cm$^{-1}$; Exact Mass: 634.28 for $C_{42}H_{38}N_2O_4$: m/z: [M$^+$]634.4

Example 1

Synthesis of perylene tetracarboxylic acid bis(1,1,1,3,3,5,5-heptamethyltrisiloxanyl propylimide) (Compound (1-1) ((1), m=1, n=1))

1.03 g (2.19 mmol) of perylene tetracarboxylic acid bis(allylimide) (compound (6), m=1, n=1) and 1.53 g (6.87 mmol) of 1,1,1,3,3,5,5-heptamethyl trisiloxane were dissolved in 100 ml of toluene, and 20 μl of a Karstedt catalyst (2 mol/l solution in xylene) was thereafter added thereto, which was then refluxed for 5 hours. The reaction solution thus obtained was then cooled and filtered, and the toluene was distilled off from a filtrate. The crude product thus obtained was purified by silica gel column chromatography (eluent: dichloromethane→dichloromethane-ethyl acetate (50:1)). The resultant crude product was dissolved in dichloromethane and re-precipitated with methanol. Thus, 1.51 g (1.65 mmol) of a red powder was obtained as an intended compound (1-1). A yield of the compound (1-1) was 75.3%. Values obtained by instrumental analysis of the compound (1-1) are shown below.

Compound (1-1):
$^1$H NMR (400 MHz, CDCl$_3$): δ=8.47 (d, 4H, J=8.0 Hz), 8.29 (d, 4H, J=8.0 Hz), 4.17 (t, 4H, J=7.6 Hz), 1.74-1.84 (m, 4H), 0.71 (t, 4H, J=4.1 Hz), 0.10 (s, 12H), 0.05 (s, 18H), 0.01 (s, 12H); $^{13}$C NMR (100 MHz CDCl$_3$): δ=0.93, 2.07, 2.59, 16.4, 22.8, 44.2, 123.5, 123.9, 126.7, 129.8, 131.7, 134.8, 163.7; IR (ATR): ν=2958, 1694, 1651, 1593, 1337, 1251, 1044, 836, 791, 743, 395 cm$^{-1}$; Exact Mass: 914.31 for $C_{44}H_{62}N_2O_8Si_6$: m/Z: [M$^+$]914.3

Example 2

Synthesis of perylene tetracarboxylic acid bis{di-(1,1,1,3,3,5,5-heptamethyl trisiloxanyl butyl)-methylimide}(Compound (2-1) ((2), m=1, n=1))

0.87 g (1.35 mmol) of perylene tetracarboxylic acid bis(1,8-nonadiene-5-ylimide) (compound (10), m=1, n=11) and 1.62 g (7.3 mmol) of 1,1,1,3,3,5,5-heptamethyl trisiloxane were dissolved in 100 ml of toluene, and 10 ml of a Karstedt catalyst (2 mol/l solution in xylene) was added to the solution thus obtained, which was then refluxed for 3 hours. The reaction solution thus obtained was cooled, the toluene was distilled off, and the crude product thus obtained was purified by silica gel column chromatography (eluent: hexane-ethyl acetate of 30:1→20:1). Then, the solvent was distilled off. Thus, 1.44 g (0.94 mmol) of a jelly-like purple-red product was obtained as a compound (2-1). A yield of the compound (2-1) was 69.5%. Values obtained by instrumental analysis of the compound (2-1) were shown below.

Compound (2-1):
$^1$H NMR (400 MHz, CDCl$_3$): δ=8.68 (d, br, 4H, J=8.0 Hz), 8.62 (d, 4H, J=8.0 Hz), 5.16 (tt, 2H, J=9.2, 6.0 Hz), 2.18-2.29 (m, 4H), 1.80-1.91 (m, 4H), 1.19-1.42 (m, 16H), 0.47 (dd, 8H, J=8.8, 7.2 Hz), 0.03 ppm (s, 36H), −0.01 ppm (s, 24H), −0.04 ppm (s, 24H); $^{13}$C NMR (100 MHz CDCl$_3$): δ=0.3, 1.4, 2.0, 18.5, 23.4, 31.0, 32.3, 55.0, 123.2, 124.2, 129.8, 131.4, 134.7, 164.0; IR (ATR): ν=2958, 1697, 1651, 1594, 1338, 1254, 1038, 837, 791, 748 cm$^{-1}$; Exact Mass: 1522.65 for $C_{70}H_{126}N_2O_{12}Si_{12}$: m/z: 1522.5.

Example 3

Production of Liquid Crystal Cell of perylene tetracarboxylic acid bis(1,1,1,3,3,5,5-heptamethyltrisiloxanyl propylimide) (Compound (1-1) ((1), m=1, n=1))

Figure 1B:
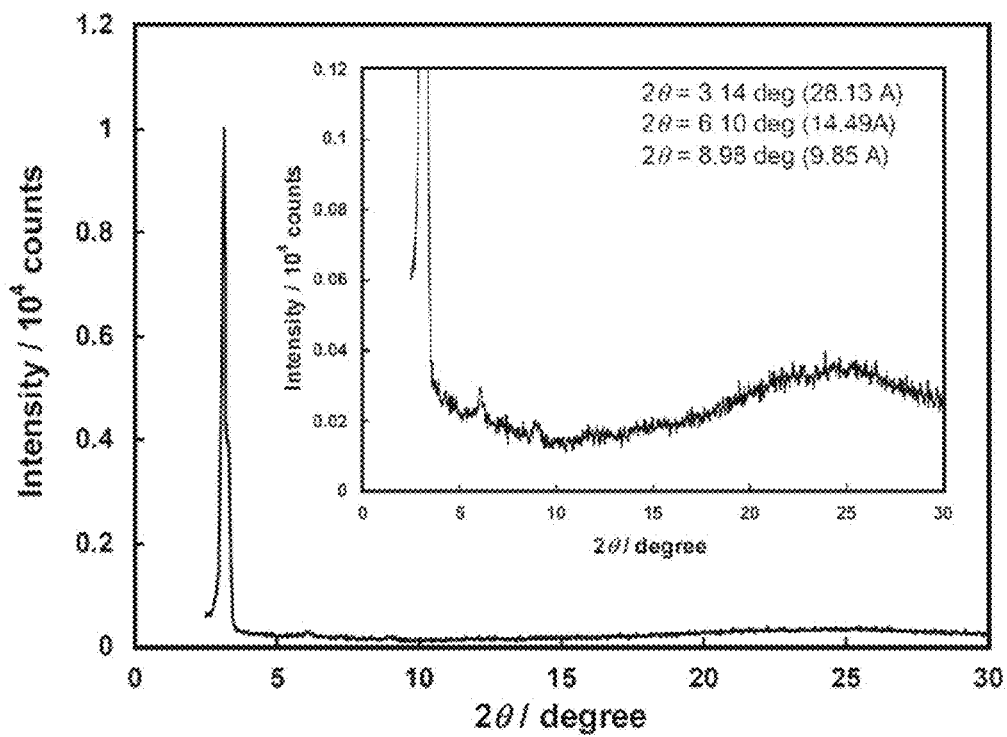
FIG. 1B is a graph showing an X-ray diffraction pattern of the sample in FIG. 1A at room temperature.
Figure 1C:
FIG. 1C is a polarization microscope photograph of a liquid crystal sample produced in Example 3 at 30° C. (crystal phase) in the case where the liquid crystal sample is slowly cooled from 220° C.
Figure 1D:
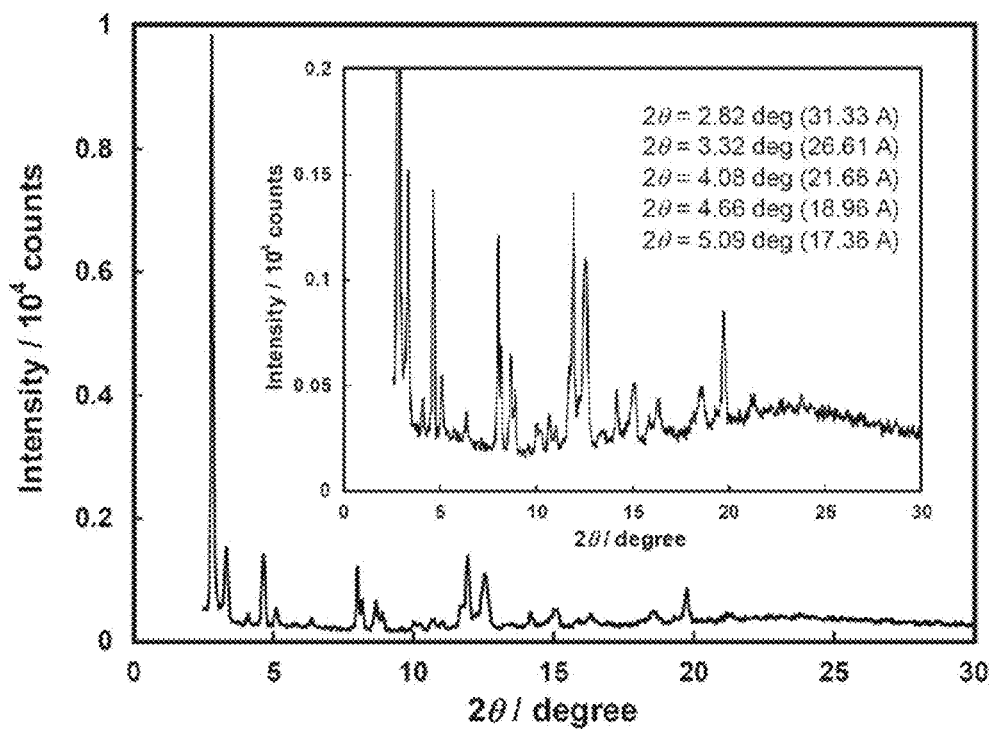
FIG. 1D is a graph showing an X-ray diffraction pattern of the sample in FIG. 1C at room temperature.

A liquid crystal cell was produced using the liquid crystal compound, perylene tetracarboxylic acid bis{di-(1,1,1,3,3,5,5-heptamethyl trisiloxanylbutyl)-methylimide}(compound (1), m=11, n=11 (compound (1-1))) obtained in Example 1, and a liquid crystal phase thereof was identified, as described below. That is, first, the liquid crystal compound (1-1) obtained in Example 1 was heated to 225° C. to melt and was permeated into a liquid crystal cell formed of two ITO electrode glass substrates, each with a thickness of 9 μm, utilizing a capillary phenomenon. An optical texture of the liquid crystal cell was observed with a polarization microscope. As shown in a microscope photograph of FIG. 1A, a smectic phase-specific texture appeared when the sample was cooled from 221° C. to 30° C. A graph of FIG. 1B shows an X-ray diffraction pattern of the sample in FIG. 1A at room temperature (30° C.). In FIG. 1B, the horizontal axis indicates a scattering angle 2θ, and the unit thereof is "° (degree)" in degree measure, and the vertical axis indicates an X-ray intensity (×10$^4$ cps). As shown in FIG. 1B, in the X-ray diffraction, a diffraction peak reflecting a layer structure appeared at 2θ=3.14° (30° C.). An inset figure in FIG. 1B is a partially enlarged view of FIG. 1B. As shown in FIG. 1C, a crystal phase appeared when the sample was slowly cooled from 220° C. A graph of FIG. 1D shows an X-ray diffraction pattern of the sample in FIG. 1C at room temperature (30° C.). In FIG. 1D, the horizontal axis indicates a scattering angle 2θ, and the unit thereof is "° (degree)" in degree measure, and the vertical axis indicates an X-ray intensity (×10$^4$ cps). As shown in FIG. 1D, in the X-ray diffraction, a crystal phase-specific higher-order diffraction peak appeared. A deposit obtained by dissolving this material (compound (1-1)) in heated toluene or cyclohexane and cooling the solution thus obtained exhibited a liquid crystal phase. A thin film obtained by spin coating, described below also exhibited a liquid crystal phase. A peak showing crystallization did not appear in differential scanning calorimetry (DSC) even when the sample in the liquid crystal state was cooled to −50° C. When the sample was heated to 200° C. or more, the phase was transferred from a liquid crystal phase to a crystal phase.

Example 4

Production of Liquid Crystal Cell of perylene tetracarboxylic acid bis{di-(1,1,1,3,3,5,5-heptamethyl trisiloxanylbutyl)-methylimide}(Compound (2-1) ((2), m=1, n=1))

Figure 2A:
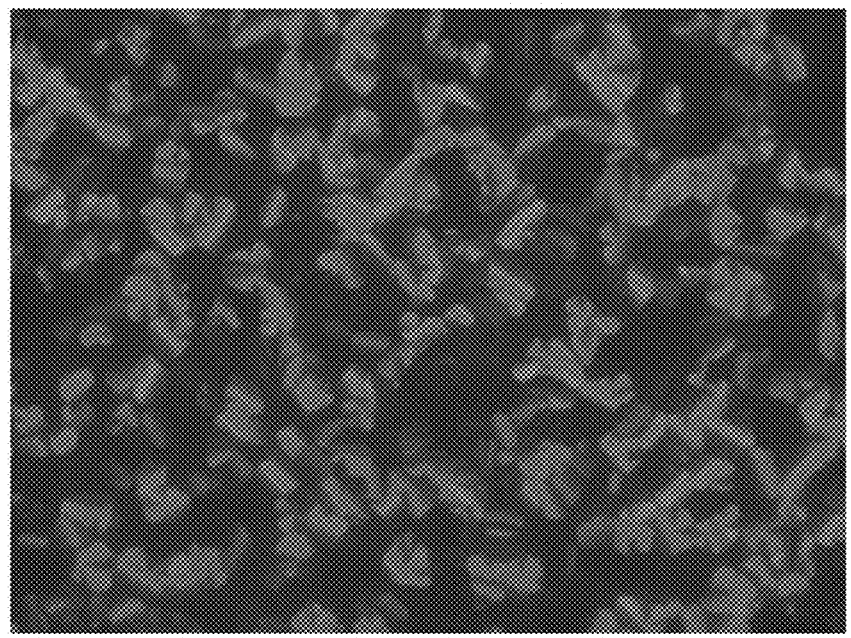
FIG. 2A is a polarization microscope photograph of a liquid crystal sample produced in Example 4 at 30° C. (Col phase).

A liquid crystal cell was produced using the liquid crystal compound, perylene tetracarboxylic acid bis{di-(1,1,1,3,3,5, 5-heptamethyl trisiloxanyl butyl)-methylimide}(compound (2), m=1, n=1 (compound (2-1))), obtained in Example 2, and a liquid crystal phase thereof was identified. That is, first, the liquid crystal compound (2-1) obtained in Example 2 was heated to 80° C. to melt and was permeated into a liquid crystal cell formed of two ITO electrode glass substrates, each with a thickness of 9 μm, utilizing a capillary phenomenon. An optical texture of the liquid crystal cell was observed with a polarization microscope. As shown in a polarization microscope photograph of FIG. 2A, a columnar phase-specific mosaic texture did not appear when the sample was 61°

Figure 2B:
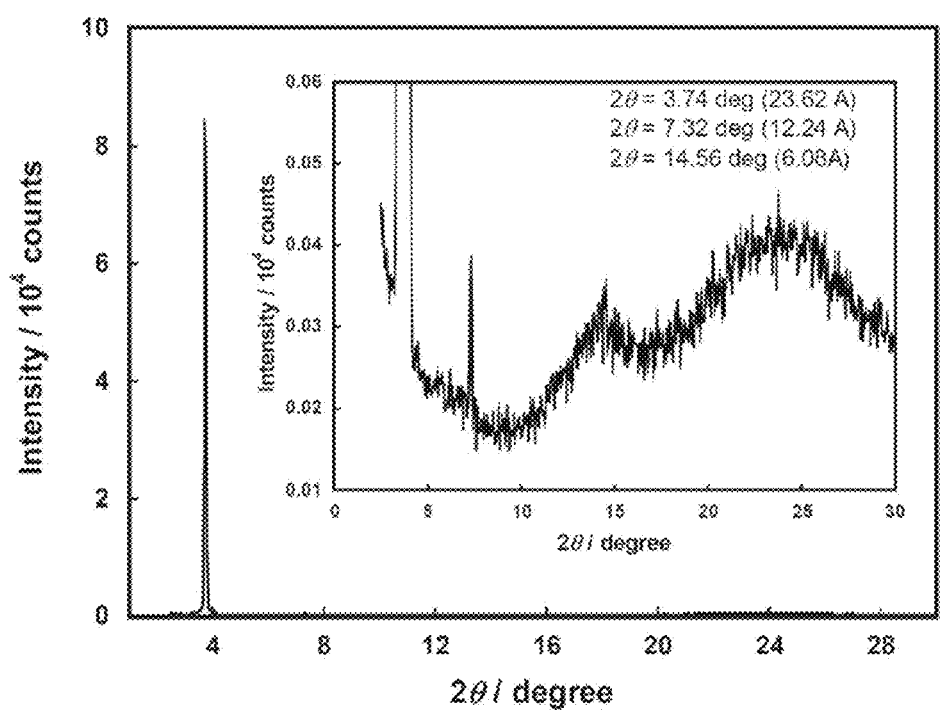
FIG. 2B is a graph showing an X-ray diffraction pattern of a liquid crystal sample produced in Example 4 at 30° C.

C. or less. A peak showing crystallization did not appear in differential scanning calorimetry (DSC) even when the liquid crystal compound was cooled to −50° C. A graph of FIG. 2B shows an X-ray diffraction pattern of the sample in FIG. 2A at room temperature (30° C.). In FIG. 2B, the horizontal axis indicates a scattering angle 2θ, and the unit thereof is "° (degree)" in degree measure, and the vertical axis indicates an X-ray intensity (×10$^4$ cps). As shown in FIG. 2B, in the X-ray diffraction, a diffraction peak reflecting a two-dimensional column order did not appear at 2θ=3.74°, 7.32° (30° C.). Only a broad halo occurred in a high-angle region. Thus, it can be considered that there is no molecular order in a column.

Example 5

Production of Thin Film (n-Type Organic Semiconductor) of perylene tetracarboxylic acid bis(1,1,1,3,3,5,5-heptamethyltrisiloxanyl propylimide) (Compound (1-1) ((1), m=1, n=1)) by Spin Coating Method The liquid crystal compound (1-1) ((1), m=1, n=1) synthesized in Example 1 is soluble in toluene, chlorobenzene, tetrahydrofuran, chloroform, dichloromethane, and the like. Thus, the liquid crystal compound (1-1) can be formed into a film by a spin coating method using a solution in any of these solvents. The film formation was performed as follows in the present example.

Figure 3A:
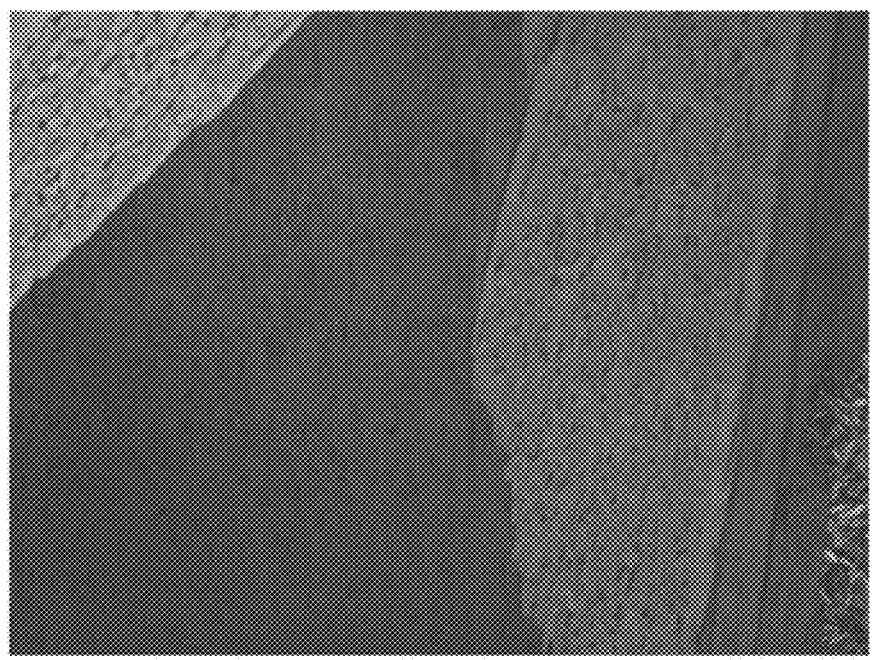
FIG. 3A is a polarization microscope photograph of a crystalline thin film of a liquid crystal compound (1-1) produced in Example 5 at 30° C.
Figure 3B:
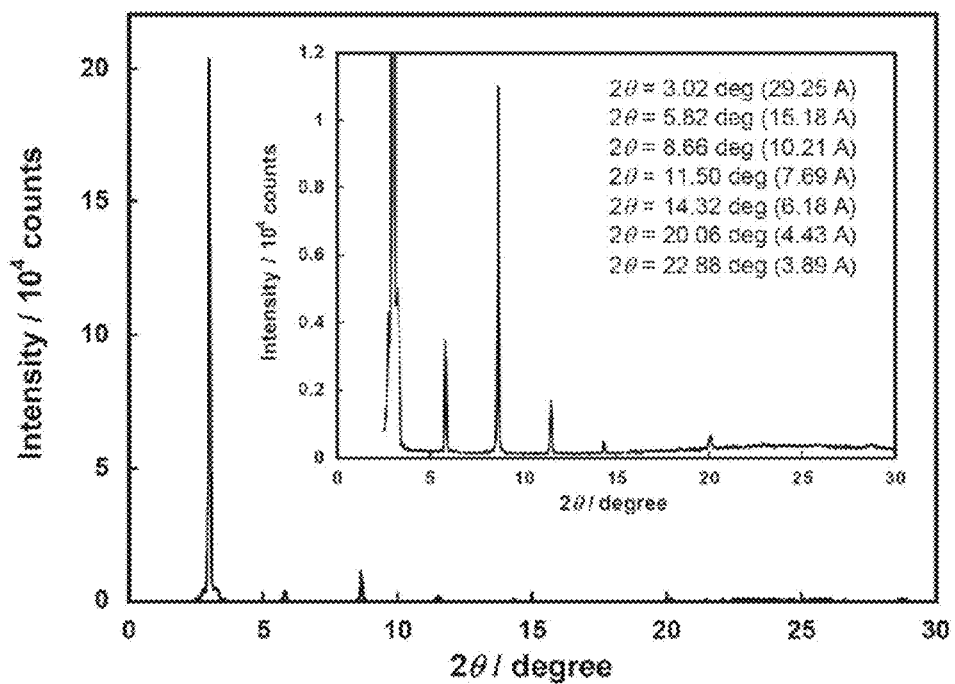
FIG. 3B is a graph showing an X-ray diffraction pattern of the crystalline thin film produced in Example 5 at 30° C.

That is, first, 50 mg of the liquid crystal compound (1-1) ((1), m=1, n=1) was dissolved in 0.5 ml of tetrahydrofuran, and a glass substrate was spin-coated with the solution thus obtained (at 1000 rpm for 40 sec and at 2000 rpm for 30 sec). Thus, a thin film with a thickness of 1 μm was obtained. This thin film was formed of domains each with a size of about 1 μm. This thin film was heat-treated at 220° C. and slowly cooled to 30° C. Thus, the thin film was transferred into a polycrystalline thin film formed of grains, each with a size of several micrometers, as shown in a microscope photograph of FIG. 3A. A graph of FIG. 3B shows an X-ray diffraction pattern of the sample in FIG. 3A at room temperature (30° C.). In FIG. 3B, the horizontal axis indicates a scattering angle 2θ, and the unit thereof is "° (degree)" in degree measure, and the vertical axis indicates an X-ray intensity (×10$^4$ cps). As shown in FIG. 3B, in the X-ray diffraction, an intense primary diffraction peak derived from a layer structure appeared at 2θ=3.02°, subsequently, the secondary to septenary high-order diffraction peaks appeared. Such liquid crystal phase can be used as an n-type organic semiconductor. As shown in Example 3 and FIGS. 1A to 1D, the compound (1-1) can exhibit a liquid crystal phase according to the cooling conditions after heating and the like.

Example 6

Production of Thin Film (n-Type Organic Semiconductor) of perylene tetracarboxylic acid bis{di-(1,1,1,3,3,5,5-heptamethyl trisiloxanylbutyl)-methylimide}(Compound (2-1) (Compound (2), m=1, n=1)) by Spin Coating Method The liquid crystal compound (2-1) ((2), m=1, n=1) synthesized in Example 2 is soluble in ethyl acetate, acetone, cyclohexane, and the like in addition to toluene, chlorobenzene, tetrahydrofuran, chloroform, dichloromethane, and the like. Thus, the liquid crystal compound (2-1) can be formed into a film by a spin coating method using a solution in any of these solvents. The film formation was performed as follows in the present example.

Figure 4A:
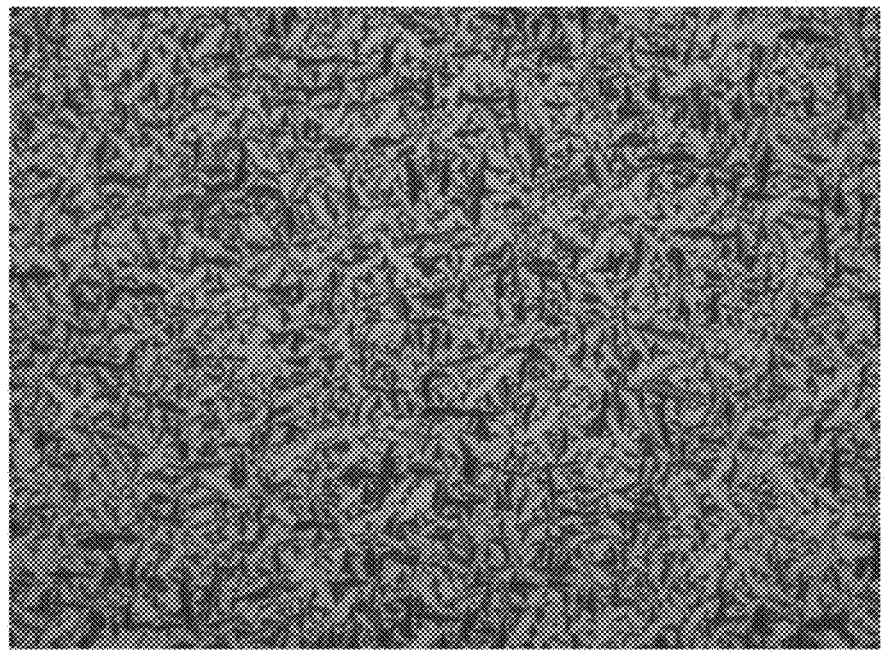
FIG. 4A is a polarization microscope photograph of a liquid crystalline thin film of a liquid crystal compound (2-1) produced in Example 6 at 30° C.
Figure 4B:
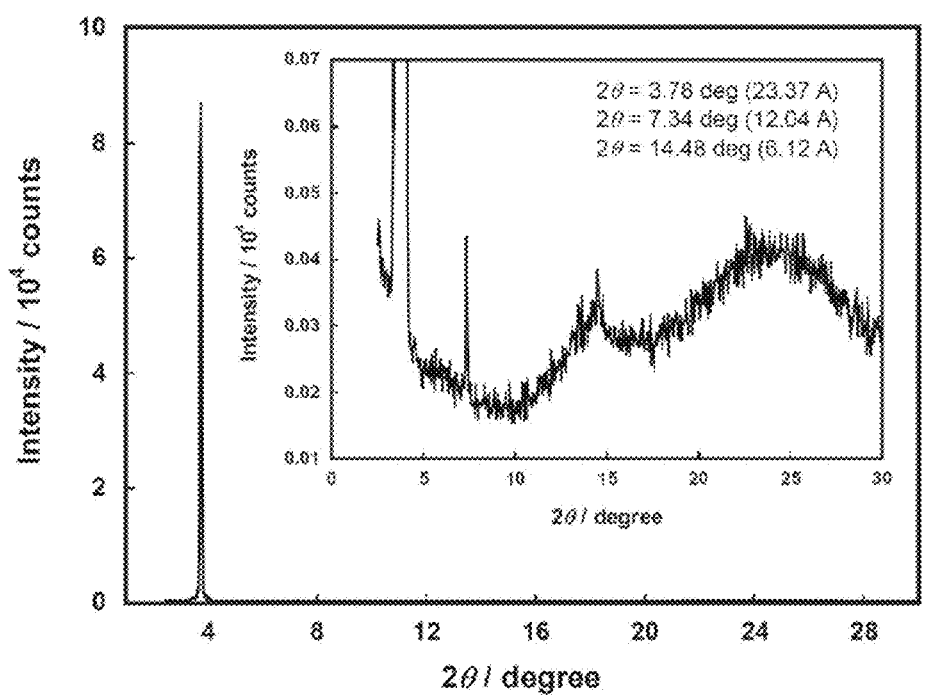
FIG. 4B is a graph showing an X-ray diffraction pattern of the liquid crystalline thin film produced in Example 5 at 30° C.

That is, first, 50 mg of the liquid crystal compound (2-1) ((2), m=1, n=1) was dissolved in cyclohexane, and a glass substrate was spin-coated with the solution thus obtained (at 500 rpm for 10 sec, at 1000 rpm for 30 sec, and at 2000 rpm for 30 sec). Thus, a thin film with a thickness of 1 μm was obtained. This thin film was formed of fine domains each with a size of 1 μm or less. This thin film was heated to 60° C. to cause the thin film to be in an isotropic phase, cooled to 55° C. to cause the thin film to be in a columnar phase, and left for 1 hour. Thus, as shown in a microscope photograph of FIG. 4A, domains each with a size of about several hundred micrometers were formed. A graph of FIG. 4B shows an X-ray diffraction pattern of the sample in FIG. 4A at room temperature (30° C.). In FIG. 4B, the horizontal axis indicates a scattering angle 2θ, and the unit thereof is "° (degree)" in degree measure, and the vertical axis indicates an X-ray intensity (×10$^4$ cps). As shown in FIG. 4B, in the X-ray diffraction, peaks appeared at 2θ=3.74° and 7.32° according to a column orientational order.

Measurement of Ultraviolet-Visible Absorption Spectrum of perylene tetracarboxylic acid bis(1,1,1,3,3,5,5-heptamethyltrisiloxanyl propylimide) (Compound (1-1) ((1), m=1, n=1)), and perylene tetracarboxylic acid bis{di-(1,1,1,3,3,5,5-heptamethyl trisiloxanylbutyl)-methylimide}(Compound (2-1) ((2), m=1, n=1))

Figure 5:
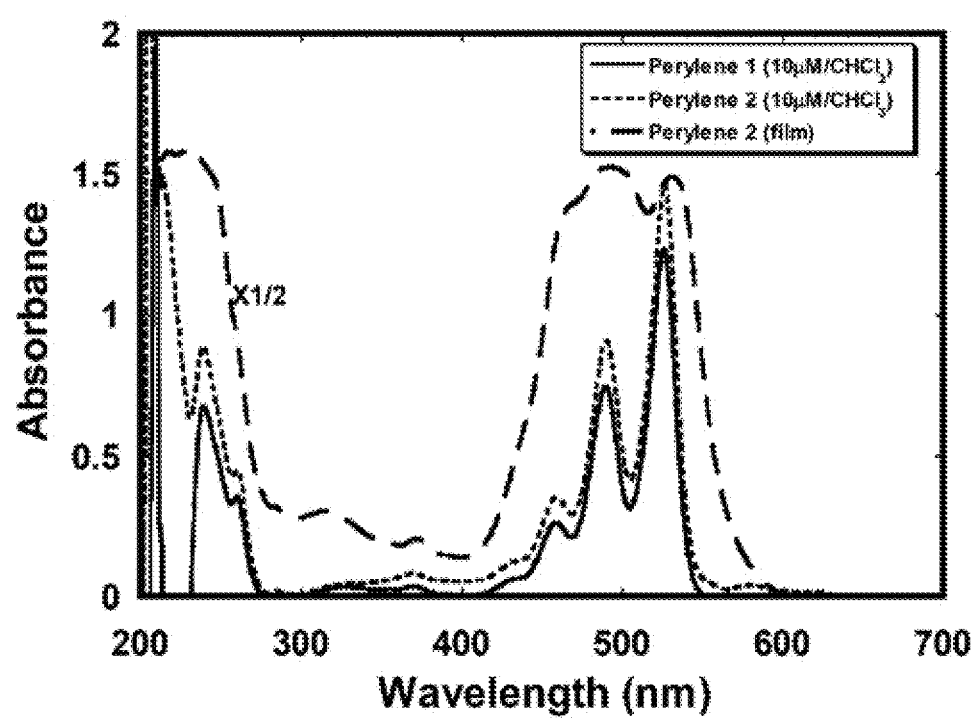
FIG. 5 shows ultraviolet-visible absorption spectra of a liquid crystal compound (1-1) produced in Example 1 and a liquid crystal compound (2-1) produced in Example 2.

Ultraviolet-visible absorption spectra of liquid crystal compounds (1-1) ((1), m=1, n=1) and (2-1) ((2), m=1, n=1) obtained in Examples 1 and 2 were measured. A graph of FIG. 5 shows the spectra. In FIG. 5, the horizontal axis indicates a wavelength (nm), and the vertical axis indicates an absorbance. In FIG. 5, a solid line (Perylene 1 (10 μM/CHCl$_3$)) indicates a spectrum of a 10 μM solution of the compound (1-1) in chloroform, a dotted line (Perylene 2 (10 μM/CHCl$_3$)) indicates a spectrum of a 10 μM solution of the compound (2-1) in chloroform, and a dashed line (Perylene 2 (film)) indicates a spectrum of the compound (2-1) formed into a thin film as in Example 6. As shown in FIG. 5, the liquid crystal compound (1-1) ((1), m=1, n=1) had absorption maximum at 525 nm in the solution in chloroform, and the liquid crystal compound (2-1) ((2), m=1, n=1) had absorption maximum at 525 nm in the solution in chloroform and at 535 nm in the state of a thin film. Since the liquid crystal compounds have absorption maxima in a visible light region as described above, the liquid crystal compounds can be combined with a p-type organic semiconductor to produce a solar battery or a photoelectric conversion element, having spectral sensitivity in the entire visible right region, for example. The p-type organic semiconductor is not particularly limited and can be, for example, a phthalocyanine derivative.

Measurement of Reduction Potential of perylene tetracarboxylic acid bis(1,1,1,3,3,5,5-heptamethyltrisiloxanyl propylimide) (Compound (1-1) ((1), m=1, n=1)) and perylene tetracarboxylic acid bis{di-(1,1,1,3,3,5,5-heptamethyltrisiloxanylbutyl)-methylimide}(Compound (2-1) ((2), m=1, n=1))

Figure 6A:
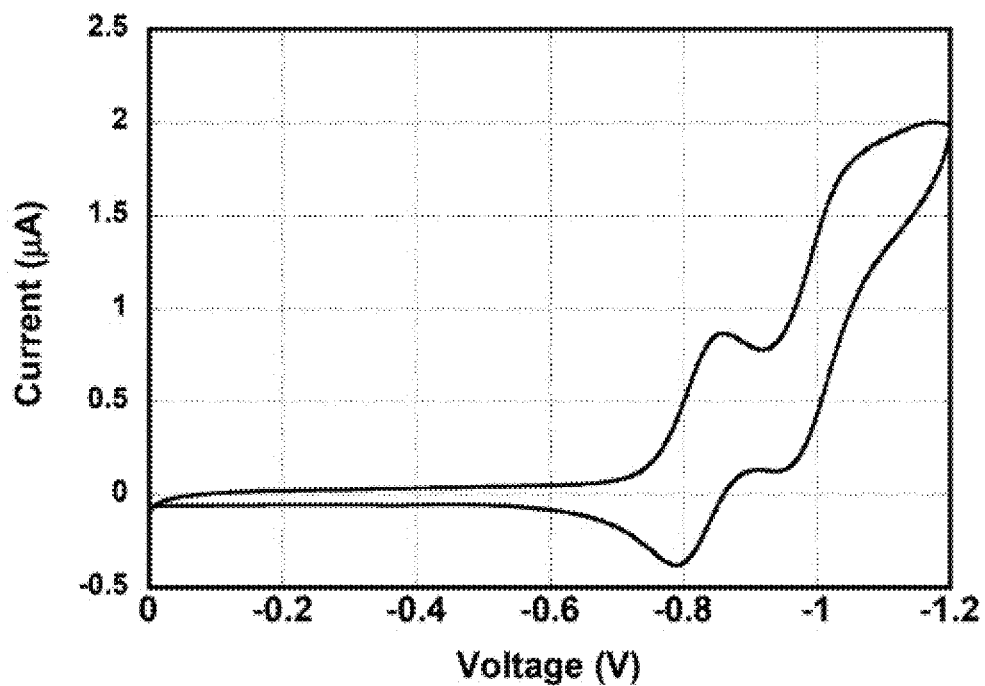
FIG. 6A is a cyclic voltammogram in a solution of a liquid crystal compound (1-1) produced in Example 1 in dichloromethane.
Figure 6B:
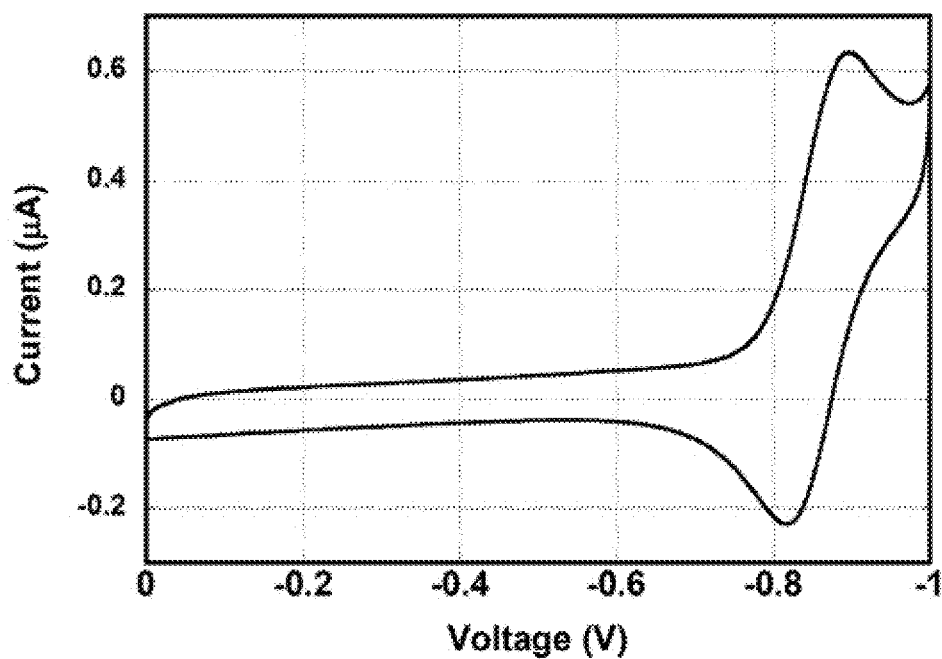
FIG. 6B is a cyclic voltammogram in a solution of a liquid crystal compound (2-1) produced in Example 1 in dichloromethane.

Oxidation-reduction potentials of the liquid crystal compounds (1-1) ((1), m=1, n=1) and (2-1) ((2), m=1, n=1) obtained in Examples 1 and 2 were measured by cyclic voltammetry. That is, the liquid crystal compound (1-1) or (2-1)

was dissolved in a solution (0.1 mol/l) of tetrabutylammoniumperchlorate in dichloromethane to prepare a 0.1 mmol/l solution. A triangle wave was applied to the solution using an Ag⁺/Ag electrode as a reference electrode, a platinum wire as a counter electrode, a glassy carbon electrode as a working electrode. A graph of FIG. 6A shows a cyclic voltammogram of the compound (1-1), and a graph of FIG. 6B shows a cyclic voltammogram of the compound (2-1). In FIGS. 6A and 6B, the horizontal axis indicates an oxidation-reduction potential (V), and the vertical axis indicates a current value (μA). As shown in FIGS. 6A and 6B, both of the liquid crystal compounds exhibited a reversible reduction wave. The liquid crystal compound (1-1) had a reduction potential of 0.83 V (vs Ag⁺/Ag), and the liquid crystal compound (2-1) had a reduction potential of 0.86 V (vs Ag⁺/Ag).

Charge Transport Properties of perylene tetracarboxylic acid bis{di-(1,1,1,3,3,5,5-heptamethyltrisiloxanylbutyl)-methylimide}(Compound (2-1) ((2), m=1, n=1))

Charge transport properties (carrier mobility properties) of the liquid crystal compound (2-1) ((2), m=1, n=1) obtained in Example 2 were measured by a Time-of-Flight (TOF) method. In this method, while a DC voltage was applied to a sandwich-type sample (liquid crystal cell produced in Example 4) having photoconductivity, the sample was irradiated with a pulse laser to cause photocarriers to be generated on one side of the sample, and a change in displacement current (transient photocurrent) induced in an external circuit when the carriers transited in the sample over time was measured. A constant current was generated by the transit of photocarriers, and when the carriers reached the counter electrode, the current was decayed to 0. The time from a start of decay in transient photocurrent to 0 corresponds to the time required for the carriers to transit in the sample (transit time). When the thickness of the sample is represented by d (cm), an applied voltage is represented by V (volt), and the transit time is represented by $t_T$, mobility p (cm²/Vs) is represented by the following mathematical expression. When an electrode on the irradiation side is biased to positive, mobility of positive carriers is determined, and when an electrode on the irradiation side is biased to negative, mobility of negative carriers is determined.

$$\mu = \frac{d^2}{Vt_T}$$

Figure 7:
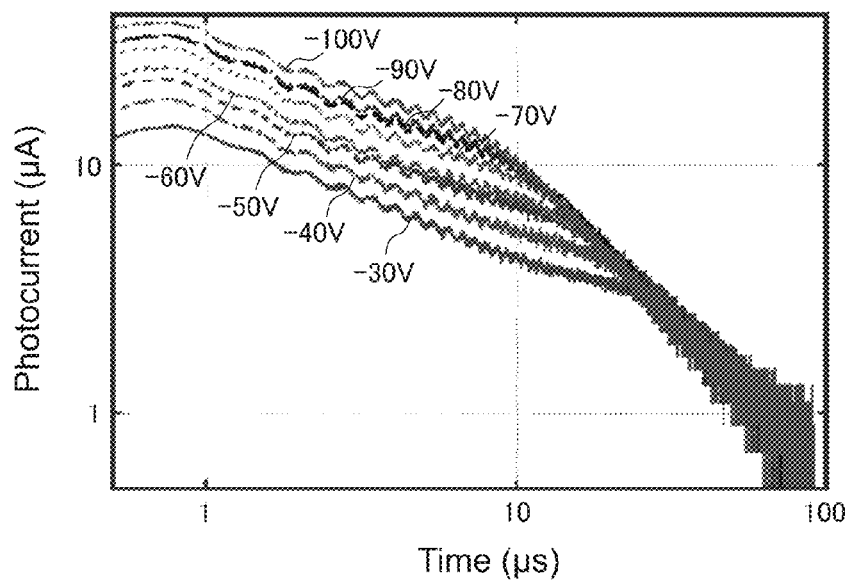
FIG. 7 is a graph showing a transient photocurrent of electrons of a liquid crystal compound (2-1) produced in Example 2 in a columnar phase at 30° C. The thickness of the sample is 9 μm, and an excitation light wavelength is 356 nm.

The measurement by a Time-of-Flight method was performed as follows. That is, while a voltage was applied to the liquid crystal cell produced in Example 4 at room temperature, the liquid crystal cell was irradiated with a pulse laser (Nd: YAG laser, THG: wavelength of 356 nm, pulse width of 1 ns), and a displacement current induced at the time of the irradiation was measured with a digital oscilloscope. FIG. 7 shows a typical result of measurement of transient photocurrent in a liquid crystal phase when an electrode on an irradiated side is biased to negative. In FIG. 7, the horizontal axis indicates time (μs), and the vertical axis indicates a photocurrent (μA). The present sample has favorable photoconductivity, and thus, sufficiently strong current signal could be obtained. As can be seen from FIG. 7, a time (transit time) at which decay of the current starts changes with a change in applied voltage, and the obtained transient photocurrent corresponds to the transit of carriers. More specifically, as shown in FIG. 7, a kink point corresponding to the carrier-transit time appeared, and it showed that electrons (negative carriers) were transited. According to the measurement result, the mobility of negative carriers reached maximum at 1×10⁻³ cm²/Vs at 30° C. This value is higher by an order of magnitude than the mobility of a conjugate polymer-fullerene derivative composite generally used in a bulk hetero junction-type organic thin-film solar battery.

Measurement of Fluorescence Spectrum of perylene tetracarboxylic acid bis(1,1,1,3,3,5,5-heptamethyl-trisiloxanylpropylimide) (Compound (1-1) ((1), m=1, n=1)) and perylene tetracarboxylic acid bis{di-(1,1,1,3,3,5,5-heptamethyl trisiloxanylbutyl)-methylimide}(compound (2-1) ((2), m=1, n=1))

Figure 8:
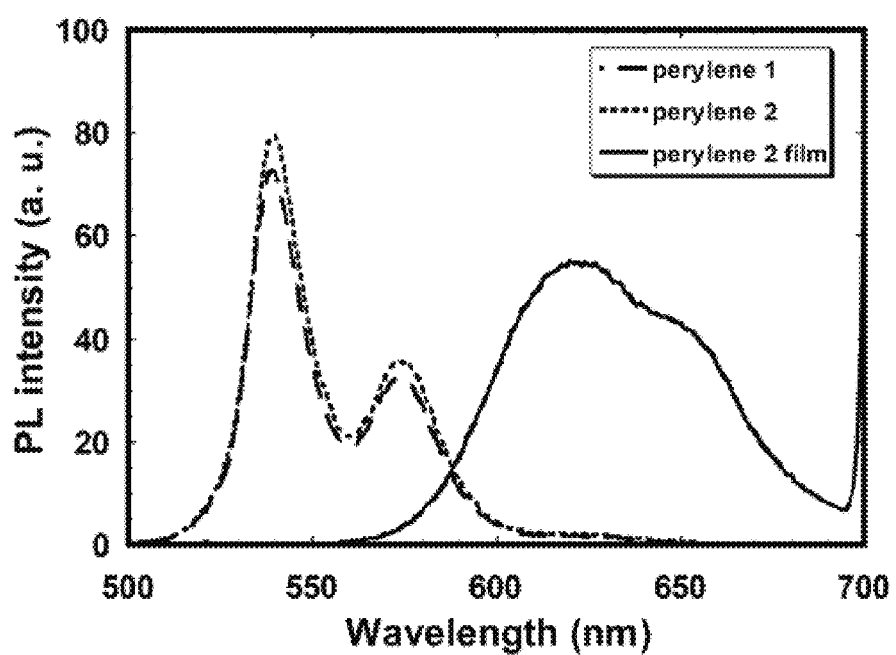
FIG. 8 shows fluorescence spectra of a liquid crystal compound (1-1) produced in Example 1 and a liquid crystal compound (2-1) produced in Example 2 in a solution thereof in chloroform and in a form of a thin film.

Fluorescence spectra of the liquid crystal compounds (1-1) ((1), m=1, n=1) and (2-1) ((2), m=1, n=1) obtained in Examples 1 and 2 were measured. A graph of FIG. 8 shows the spectra. In FIG. 8, the horizontal axis indicates a wavelength (nm), and the vertical axis indicates a fluorescence intensity (relative value). In FIG. 8, a solid line (Perylene 1) indicates a spectrum of a 10 μM solution of the compound (1-1) in chloroform, a dotted line (Perylene 2) indicates a spectrum of a 10 μM solution of the compound (2-1) in chloroform, and a dashed line (Perylene 2 film) indicates a spectrum of the compound (2-1) in a form of a thin film as in Example 6. As shown in FIG. 8, each of the liquid crystal compounds (1-1) ((1), m=1, n=1) and (2-1) ((2), m=1, n=1) had fluorescence peak wavelengths of 538 nm and 574 nm in the solution in chloroform. The liquid crystal compound (2-1) ((2), m=1, n=1) in a form of a film had a fluorescence peak wavelength of 623 nm (FIG. 8). As described above, each of the liquid crystal compounds (1-1) and (2-1) of the present example had an absorption band in a visible light region. Thus, for example, it is possible to use the liquid crystal compounds as laser pigments by dissolving them in an organic solvent.

The phase transition temperatures, the absorption maximum wavelengths, and the reduction potentials of the liquid crystal compounds (1-1) and (2-1) of the present example, measured as described above are summarized in Table 7 below.

TABLE 7

|  | Phase transition temperature (° C.) | Absorption maximum wavelength (nm) | Reduction potential (V) |
|---|---|---|---|
| Compound (1-1) ((1), m = 1, n = 1) | Iso 213 K (slow cooling) Iso 210 Sm (rapid cooling) | 525 nm (10 μM/ CHCl₃) | 0.83 vs Ag⁺/Ag |
| Compound (2-1) ((2), m = 1, n = 1) | Iso 54 Col | 525 nm (10 μM/ CHCl₃) 535 nm (film 5 μm) | 0.86 vs Ag⁺/Ag |

K: liquid crystal phase, Sm = smectic phase, Iso: isotropic phase, Col: columnar phase Example 7

Synthesis of N—N'-bis(1,9-di(1,1,1,3,3, pentamethylcyclohexanyl)nonane-5-yl)perylene-3,4,9,10-tetracarboxylic acid bisimide (Compound (2-44) ((2), m=0, n=11))

The compound (2-44) ((2), m=0, n=1) was synthesized according to the following scheme 2-2. The compound 10 was synthesized in the same manner as in Reference Examples 2 and 3 (synthesis of starting material in Example 2).

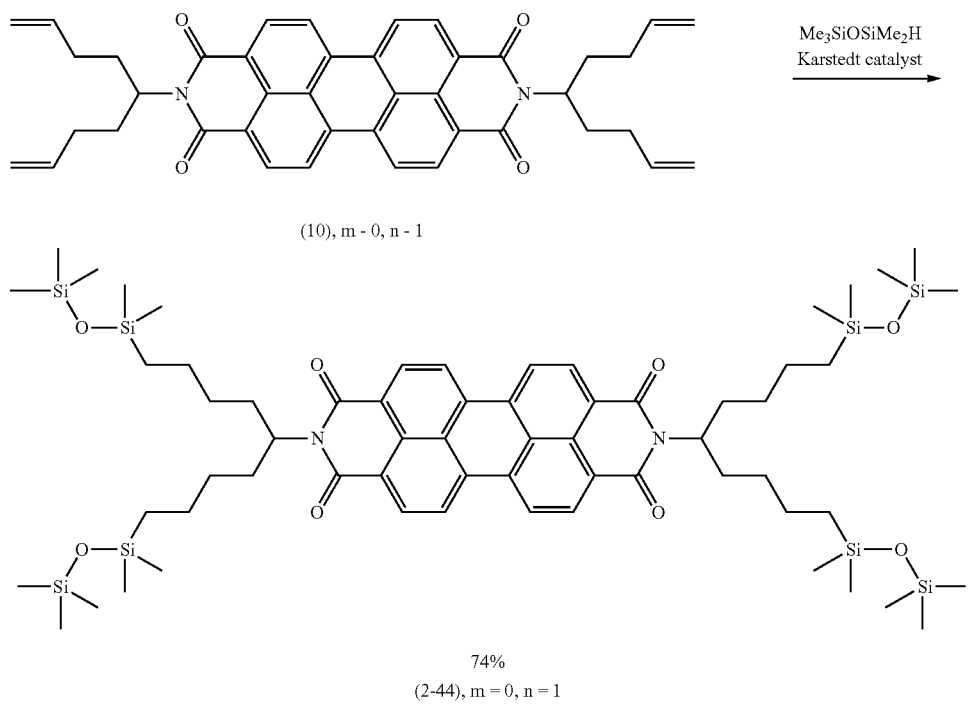

Perylene-3,4,9,10-tetracarboxylic acid bis(1,8-nonadiene-5-ylimide) (compound (10), m=1, n=1) and 1.19 g (8.1 mmol) of 1,1,1,3,3-pentamethyl disiloxane were dissolved in 30 ml of toluene, and 10 μl of a Karsted catalyst (2.1 At %, a solution in xylene) was added to the solution thus obtained, which was then refluxed for 2 hours. The resultant solution was cooled to room temperature, and the solvent was distilled off under reduced pressure. Then, the red residue thus obtained was purified by silica gel column chromatography (eluent: hexane:ethyl acetate=10:1). The crude product thus obtained was dissolved in dichloromethane and re-precipitated with methanol. The precipitate thus obtained was separated by filtration. Thus, 1.29 g (1.05 mol) of a red powder was obtained as an intended compound (2-44). A yield of the compound (2-44) was 74%. Values obtained by instrumental analysis of the compound (2-44) are shown below.

Compound (2-44):

$^1$H NMR (400 MHz, CDCl$_3$): δ=8.68 (d, br, 4H, J=8.0 Hz), 8.62 (d, 4H, J=8.0 Hz), 5.16 (tt, 2H, J=9.2, 6.0 Hz), 2.18-2.29 (m, 4H), 1.80-1.91 (m, 4H), 1.19-1.42 (m, 16H), 0.47 (dd, 8H, J=8.8, 7.2 Hz), −0.01 ppm (s, 36H), −0.04 ppm (s, 24H); IR (ATR): ν=2958, 1697, 1651, 1594, 1338, 1254, 1044, 837, cm$^{-1}$; Exact Mass: 1226.58; Molecular
Weight: 1228.17 m/z[M+]: 1226.87 (82%), 1227.89 (100%), 1228.88 (83%), 1229.88 (43%), 1230.87 (37%)

Example 8

Production of Liquid Crystal Cell of N—N'-bis(1,9-di(1,1,1,3,3, pentamethylcyclohexanyl)nonane-5-yl) perylene-3,4,9,10-tetracarboxylic acid bisimide (compound (2-44) ((2), m=0, n=1))

Figure 9:
FIGS. 9A to 9C are polarization microscope photographs of a liquid crystal sample of a compound (2-44) produced in Example 8.

A liquid crystal cell was produced in the same manner as in Example 4 except that the compound (2-44) was used as substitute for the compound (2-1), and a liquid crystal phase thereof was identified by an observation with a polarization microscope. FIGS. 9A to 9C show results of the observation with a polarization microscope. FIG. 9A is a polarization microscope photograph taken at 136° C. FIG. 9B is a polarization microscope photograph taken at 30° C. FIG. 9C is a polarization microscope photograph taken at 136.1° C. with one polarizer. As shown in FIGS. 9A to 9C, a dendritic texture having six-fold symmetry appeared rather than an isotropic phase at each of the temperatures of 30° C. and 136° C. (136.1° C.), and thus, the liquid crystal phase was identified as a liquid crystal phase having six-fold symmetry.

X-Ray Diffraction of N—N'-bis(1,9-di(1,1,1,3,3, pentamethylcyclohexanyl)nonane-5-yl)perylene-3,4,9,10-tetracarboxylic acid bisimide (compound (2-44) ((2), m=0, n=1))

Figure 10:
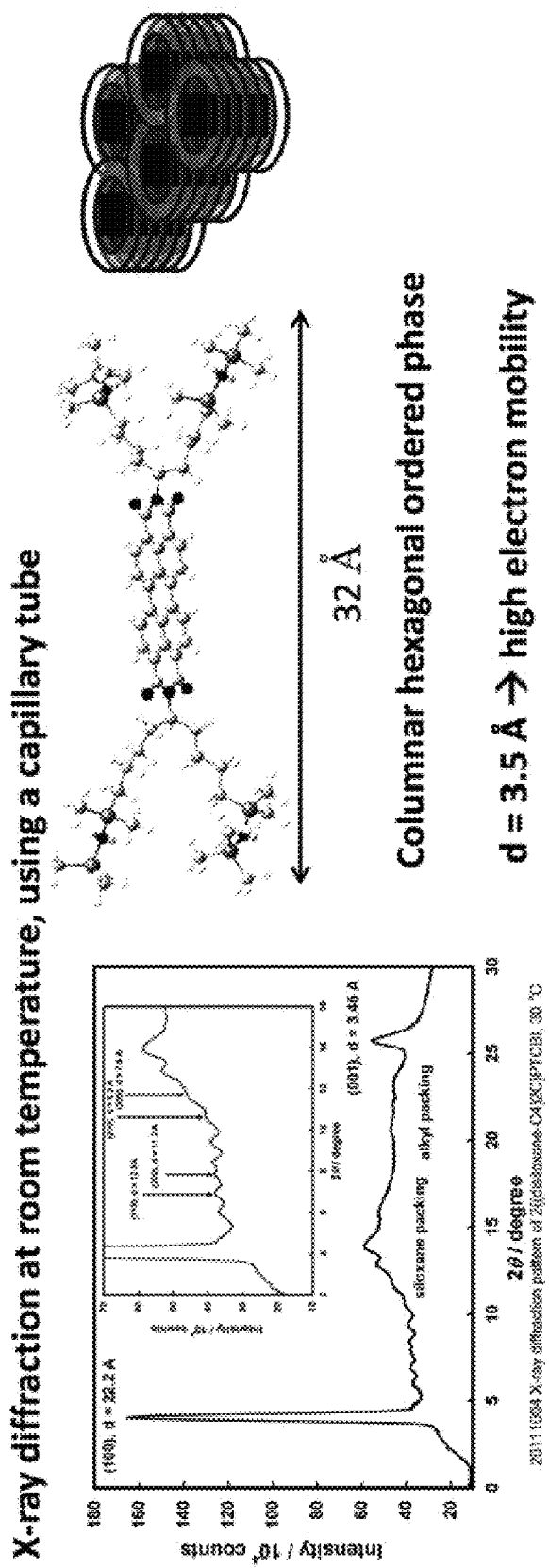
FIG. 10 is a graph showing an X-ray diffraction (XRD) pattern of a compound (2-44) ((2), m=0, n=1)) produced in Example 7 at room temperature (30° C.).

A graph of FIG. 10 shows an X-ray diffraction (XRD) pattern of the compound (2-44) ((2), m=0, n=1)) at room temperature (30° C.). In the graph, the horizontal axis indicates 2θ (°), and the vertical axis indicates a peak intensity (relative value). A figure on the right side of FIG. 10 schematically shows a structure of a liquid crystal phase identified from the graph and the polarization microscope photographs of FIGS. 9A to 9C. That is, it was identified from the X-ray diffraction pattern of FIG. 10 and the polarization microscope photographs of FIGS. 9A to 9C that the liquid crystal phase of the compound (2-44) ((2), m=0, n=1)) at room temperature (30° C.) was a hexagonal ordered columnar phase. There was a long-range molecular orientational order in the column, and the intermolecular distance was 3.46 Å (0.346 nm).

Charge Transport Properties of N—N'-bis(1,9-di(1,1,1,3,3, pentamethylcyclohexanyl)nonane-5-yl) perylene-3,4,9,10-tetracarboxylic acid bisimide (Compound (2-44) ((2), m=0, n=1))

Figure 11A:
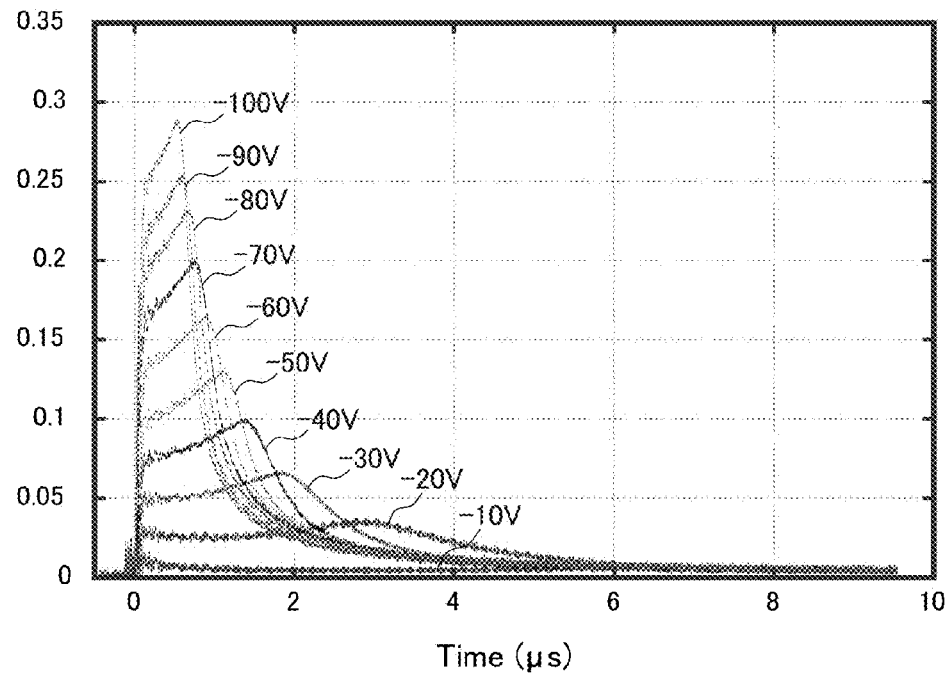
FIG. 11A is a graph showing a result of transient photocurrent measurement of the compound (2-44) by a TOF method.
Figure 11B:
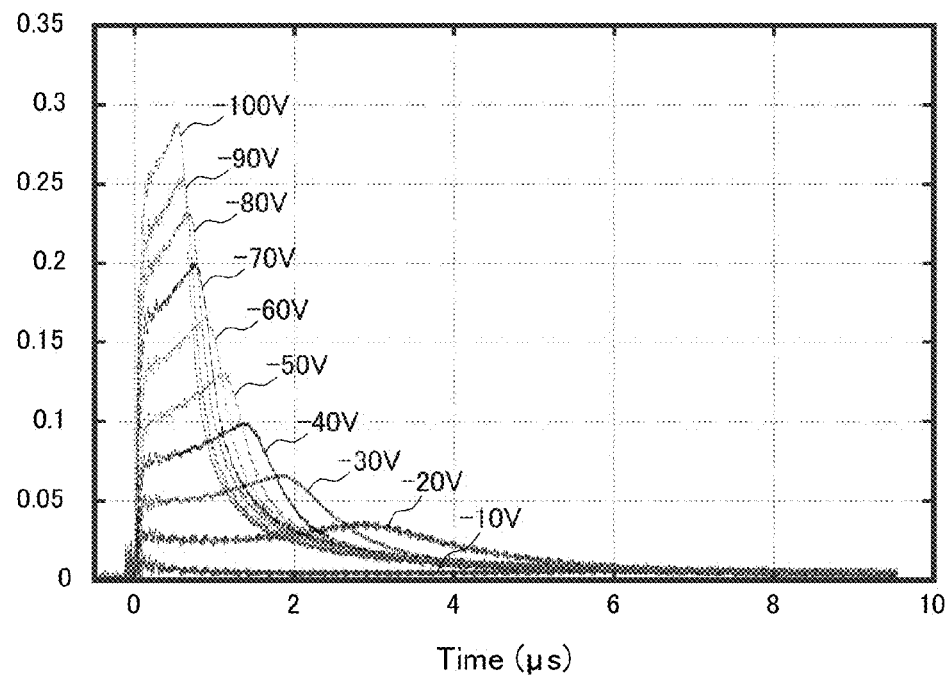
FIG. 11B is another graph showing a result of transient photocurrent measurement of the compound (2-44) by a TOF method.

Charge transport properties (carrier mobility properties) of the liquid crystal compound (2-44) ((2), m=0, n=1)) were measured through transient photocurrent measurement by a Time-of-Flight method using the liquid crystal cell produced in Example 8. The transient photocurrent measurement by a Time-of-Flight method was performed in the same manner as in the measurement of charge transport properties (carrier mobility properties) of the liquid crystal compound (2-1) ((2), m=1, n=1). The thickness of a sample of the liquid crystal compound (2-44) ((2), m=0, n=1)) was 25 μm. The measurement temperature was 40° C., and the measurement was performed while changing an applied voltage from 10 V to 100 V by 10 V increments. The graphs of FIGS. 11A and 11B show the results of the measurement. In FIGS. 11A and 11B, the horizontal axis indicates time (μs), and the vertical axis indicates a photocurrent (μA). As shown in FIGS. 11A and 11B, in the same time of flight, the higher the applied voltage was, the higher the photocurrent flowed. Moreover, as in the liquid crystal compound (2-1) ((2), m=1, n=1), it was found that a time (transit time) at which decay of the current starts changes with a change in applied voltage, and the obtained transient photocurrent corresponds to the transit of carriers. That is, as shown in FIGS. 11A and 11B, a kink point corresponding to the carrier-transit time appeared, and it showed that electrons (negative carriers) were transited.

Figure 12A:
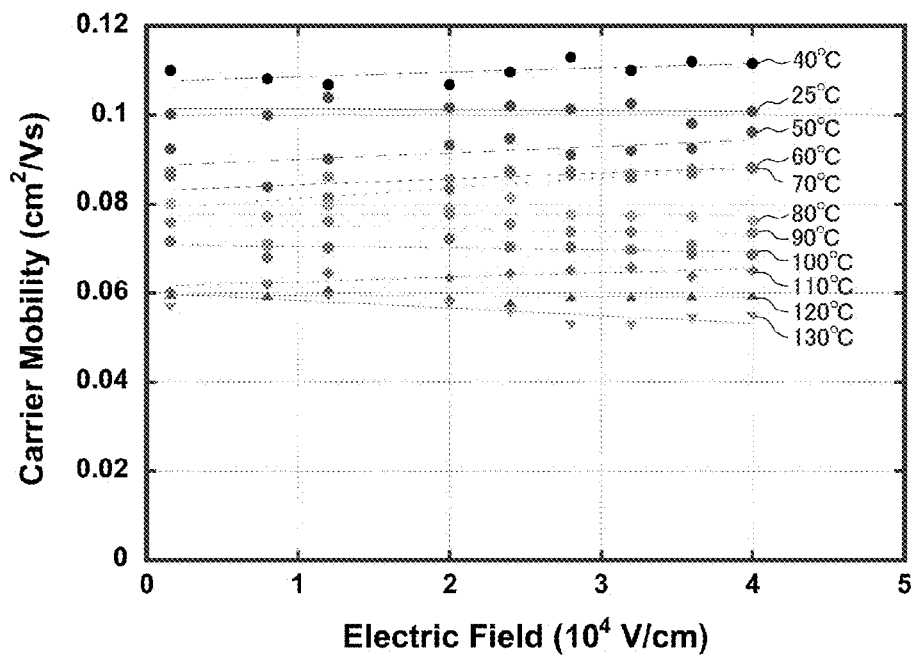
FIG. 12A is a graph showing a result of the same measurement as in FIGS. 11A and 11B with a change in measurement temperature from 25° C. to 130° C.

In addition, the same measurement as in FIGS. 11A and 11B was performed with a change in measurement temperature from 25° C. to 130° C. The result of the measurement is shown in a graph of FIG. 12A. In FIG. 12A, the horizontal axis indicates an electric field strength ($10^4$ V/cm), and the vertical axis indicates carrier mobility ($cm^2$/Vs). As mentioned above, in this measurement, it was found that electrons (negative carriers) were transferred. Thus, the vertical axis (carrier mobility) is equal to electron mobility. As shown in FIG. 12A, electron mobility was maximum at a measurement temperature of 40° C. when an electric field strength was constant. When the measurement temperature was constant, and an electric field strength changed, electron mobility was not significantly changed.

Figure 12B:
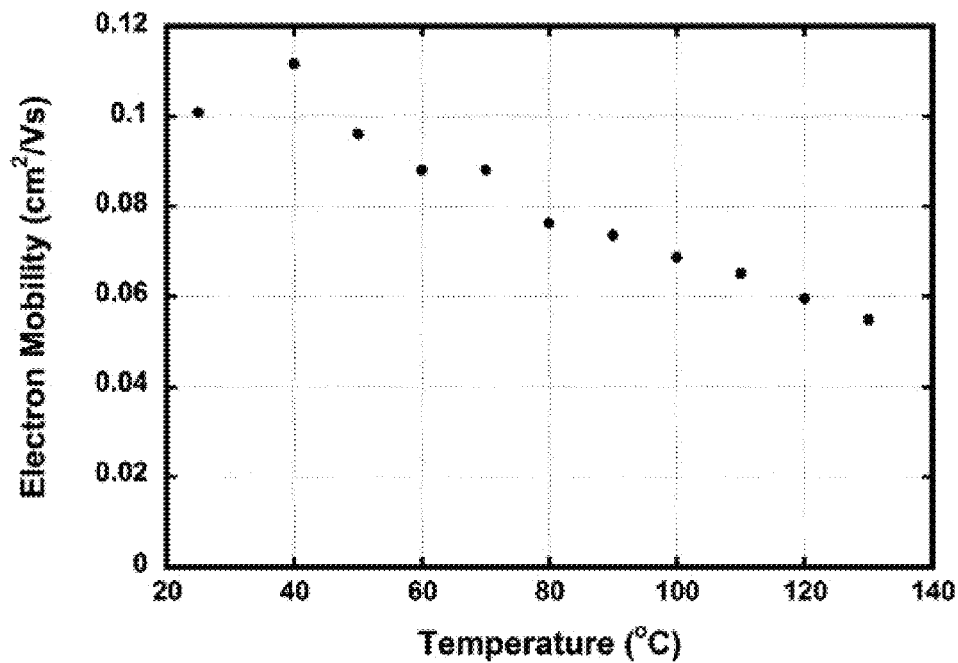
FIG. 12B is a graph showing a result of the measurement at an electric field strength of $4.0 \times 10^4$ V/cm in FIG. 12A as a function of time and electron mobility.

A result of the measurement at an electric field strength of $4.0\times10^4$ V/cm in FIG. 12A is shown in a graph of FIG. 12B as a function of time and electron mobility. In FIG. 12B, the horizontal axis indicates a temperature (° C.), and the vertical axis indicates electron mobility ($cm^2$/Vs). As can be seen from FIGS. 12A and 12B, the maximum electron mobility of a liquid crystal compound (2-44) ((2), m=0, n=1)) was $1.2\times10^{-1}$ $cm^2$/Vs at 40° C. As mentioned above, the electron mobility of the liquid crystal compound (2-1) ((2), m=1, n=1) reached a maximum at $1\times10^{-3}$ $cm^2$/Vs, and this value is higher by an order of magnitude than the electron mobility of a conjugate polymer-fullerene derivative composite generally used in a bulk heterojunction-type organic thin-film solar battery. However, the electric mobility of the liquid crystal compound (2-44) ((2), m=0, n=1)) was 100 times higher than the maximum electron mobility of the liquid crystal compound (2-1), which was really high. As described above, such high electron mobility is really advantageous to be used in high-performance electronic devices such as an organic thin-film solar battery, an organic light-emitting transistor, and CMOS, for example. Further, as shown in FIGS. 12A and 12B, the maximum electron mobility at room temperature or a temperature close to room temperature also is practically advantageous. Furthermore, as shown in FIGS. 12A and 12B, even when the temperature of the liquid crystal compound (2-44) ((2), m=0, n=1)) was increased to 130° C., the electron mobility was reduced to only about a half of the electron mobility at 40° C., and thus, the really high electron mobility was maintained. Therefore, the device can be operated stably at high temperature, so that the liquid crystal compound is further more practically advantageous.

N—N'-bis(4-(1,9-di(1,1,1,3,3,5,5-heptamethyltrisiloxanyl)nonane-5-yloxy)phenyl)perylene-3,4,9,10-tetracarboxylic acid bisimide (Compound (2-46) ((2), m=0, n=3))

A compound (2-46) ((2), m=0, n=3) was synthesized according to the following scheme 2-3 (Example 9).

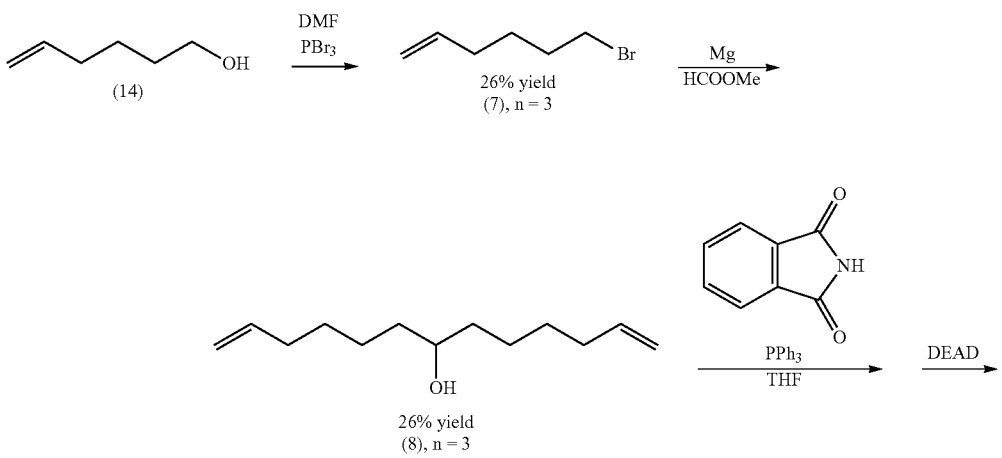

-continued
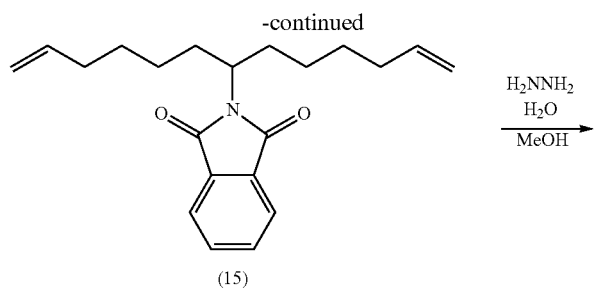
(15)
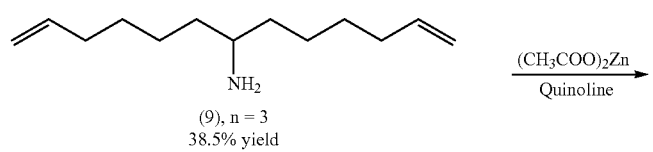
(9), n = 3
38.5% yield
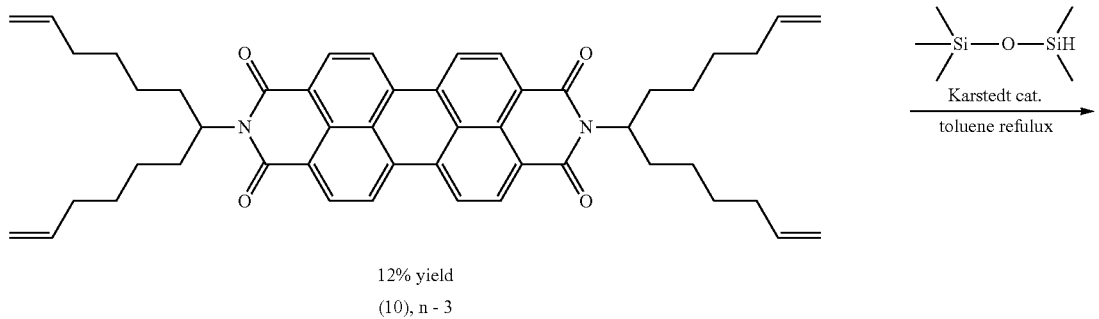
12% yield
(10), n - 3
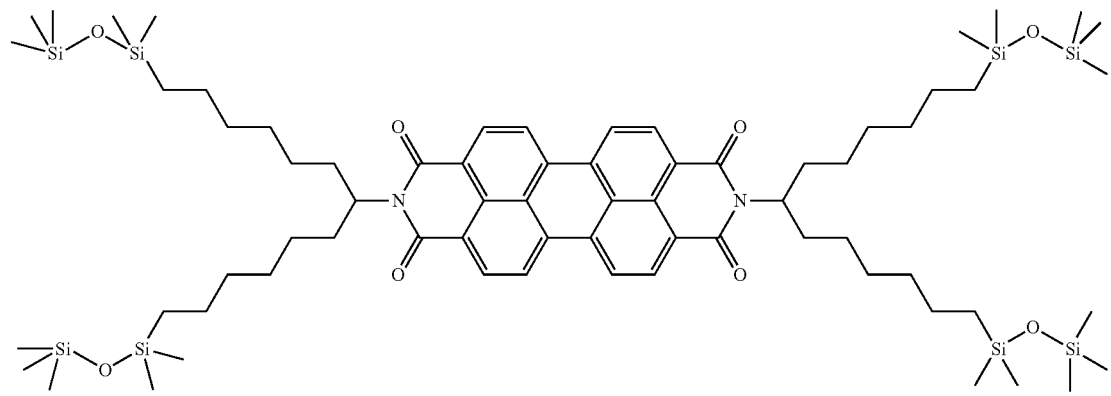
(2-46), m = 0, n = 3

Reference Example 4

Synthesis of 1-bromo-5-hexene (7)

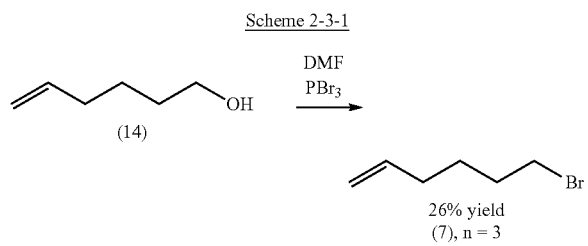

DMF (400 ml) was added to a 500 ml-capacity three neck flask containing a stirring bar and then was stirred while the flask was placed in an ice bath. Then, PBr$^3$ (19.3 ml, 20 mmol) was dropped into the flask. When a milky-white precipitate was generated, the mixture was further manually stirred for 1 hour. Thereafter, 1-hexene-6-ol (14) (20 g, 20 mmol) was added to the mixture, which was then stirred for 5 hours. When generation of bromide was recognized by thin-layer chromatography, an aqueous sodium hydroxide solution was added to the mixture to stop the reaction. An organic layer was extracted with hexane, dried over Na$_2$SO$_4$, and filtered, and the solvent was distilled off under reduced pressure. Then, the organic layer was purified by flash chromatography on silica gel (hexane). Thus, 1-bromo-5-hexene (7) (8.48 g, 5 mmol, yield: 26%) was obtained. $^1$HNMR values of the 1-bromo-5-hexene (7) are shown below.

$^1$H NMR values of 1-bromo-5-hexene (7):

$^1$H NMR (400 MHz, CDCl$_3$) δ=5.78 (ddt, 1H J$_1$=8.8 Hz, J$_2$=18.8 Hz, J$_3$=25.6 Hz), 4.97 (m, 2H), 3.38 (t, 2H, J=6.8 Hz), 2.08 (m, 2H), 1.86 (m, 2H), 1.52 (m, 2H)

Reference Example 5

Synthesis of 1,12-tridecadiene-7-ol (8)

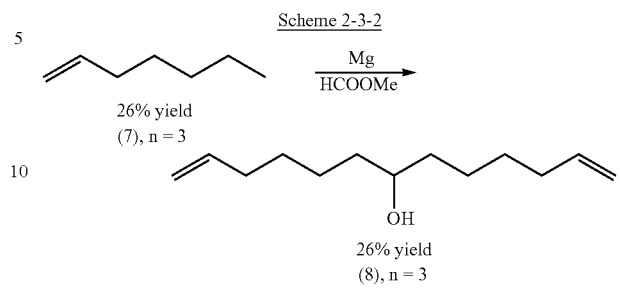

A stirring bar and Mg (1.2 g) were placed in a 500 ml-capacity three neck flask, and the flask was connected to a condenser and sufficiently dried. Then, a nitrogen atmosphere was established in the flask, and THF (20 ml) and I$_2$ were added thereto. 1-bromo-5-hexene (7) (8 g, 5 mmol) and THF (10 ml) were added to the brown suspension thus obtained to start a reaction, and heat developed when a color of I$_2$ disappeared. Immediately after the start of the heat development, the flask was placed in an ice bath. Then, after generation of a Grignard reagent, HCOOMe (1.5 ml, 5 mmol) was slowly dropped into the flask, and the mixture thus obtained was stirred for 30 minutes. When generation of alcohol was recognized by thin-layer chromatography, diluted hydrochloric acid was added to the mixture to stop the reaction. An organic layer was extracted with AcOEt and dried over Na$_2$SO$_4$, and the solvent was distilled off under reduced pressure. Thereafter, the organic layer was purified by flash chromatography on silica gel (hexane:ethyl acetate=10:1), (hexane:ethyl acetate=4:1). Thus, intended 1,12-tridecadiene-7-ol (8) (2.55 g, 1.3 mmol, yield: 26%) was obtained. $^1$HNMR values of 1,12-tridecadiene-7-ol (8) are shown below.

$^1$HNMR values of 1,12-tridecadiene-7-ol (8): δ=5.78 (ddt, 1H, J$_1$=6.8 Hz, J$_2$=16.8 Hz, J$_3$=21.6 Hz), 4.95 (m, 2H), 2.04 (m, 2H), 1.4 (m, 7H)

Reference Example 6

Synthesis of 7-amino-1,12-tridecadiene (9)

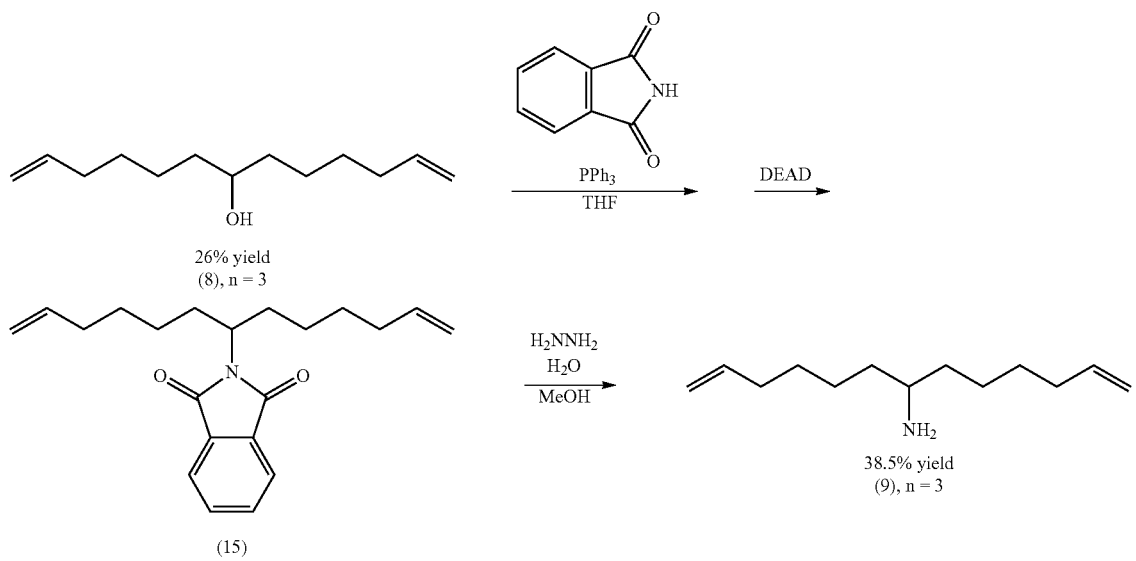

A 300 ml-capacity three neck flask containing a stirring bar and connected to a condenser was sufficiently dried. Then, a nitrogen atmosphere was established in the flask, and 1,12-tridecadiene-7-ol (8) (2.0 g, 1.2 mmol), PPh$_3$ (3.7 g, 1.4 mmol), phthalimide (3.2 g, 2.2 mmol), and THF (70 ml) were introduced into the flask, and the mixture thus obtained was stirred. DEAD (10 ml) was further added to the mixture, and the mixture thus obtained was stirred while cooling the flask in a water bath. When generation of amine was recognized by thin-layer chromatography, an organic layer was extracted with AcOEt, the solvent was distilled off under reduced pressure, and the organic layer was then purified by flash chromatography on silica gel (hexane:ethyl acetate=5:1). Thus, a compound (15) was obtained.

Subsequently, a 300 ml-capacity three neck flask containing a stirring bar and connected to a condenser was sufficiently dried. Then, a nitrogen atmosphere was established in the flask, and the purified compound (15), methanol (MeOH) (25 ml), and hydrazine monohydrate (H$_2$NNH$_2$—H$_2$O) (1.5 ml) were introduced into the flask, and the mixture thus obtained was stirred for 6 hours. When generation of amine was recognized by thin-layer chromatography, the mixture was suction-filtered with MeOH, the solvent was distilled off under reduced pressure, and an organic layer was extracted with AcOEt. Thus, 7-amino-1,12-tridecadiene (9) (0.9 g, $4.62 \times 10^{-4}$ mol, yield: 38.5%) was obtained.

Reference Example 7

Synthesis of N—N'-di(1,12-tridecadiene-7-yl) perylene-3,4,9,10,tetracarboxylic acid bisimide (10) (n=3)

Scheme 2-3-4

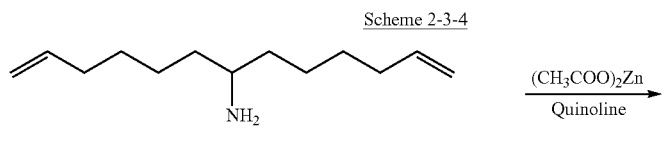

38.5% yield
(9), n = 3

(CH$_3$COO)$_2$Zn
Quinoline

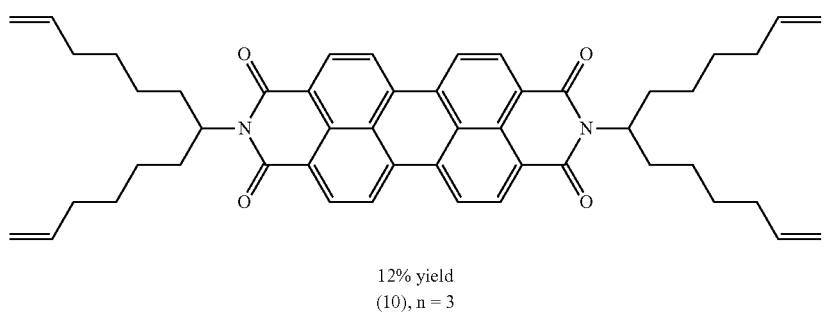

12% yield
(10), n = 3

A 200 ml-capacity three neck flask containing a stirring bar and connected to a condenser was sufficiently dried. Then, a nitrogen atmosphere was established in the flask, and the 7-amino-1,12-tridecadiene (9) (0.9 g, 0.5 mmol), zinc acetate (0.45 g, 0.5 mmol), perylene-3,4,9,10-tetracarboxylic acid (1.37 g, 0.5 mmol), and quinoline (10 ml) were introduced into the flask. This mixture thus obtained was stirred for half a day while heating the flask in an oil bath (230° C.). When a product was recognized by thin-layer chromatography, diluted hydrochloric acid was added to the mixture to stop the reaction, and the mixture thus obtained was suction-filtered with CH$_2$Cl$_2$. A filtrate was purified by flash chromatography on silica gel (CH$_2$Cl$_2$), the product thus obtained was dissolved in CH$_2$Cl$_2$ and re-precipitated with methanol. Thus, N—N'-di(1,12-tridecadiene-7-yl)perylene-3,4,9,10,tetracarboxylic acid bisimide (10) (n=3) (0.45 g, $6.63 \times 10^{-4}$ mol, yield: 12%) was obtained as an intended compound. $^1$H NMR values of the compound (10) are shown below.

$^1$H NMR values of compound (10):
$^1$H NMR (400 MHz, CDCl$_3$)
$\delta$=8.6 (d, br, 4H), 8.5 (d, 4H, J=7.6 Hz), 5.7 (ddt, 4H, $J_1$=6.8 Hz, $J_2$=16.8 Hz, $J_3$=23.6 Hz), 5.15 (m, 2H), 4.85 (m, 8H), 2.3 (m, 4H), 1.8-1.9 (m, 4H), 13 (m,), 0.8 (t, 2H, J=6.8 Hz), −0.07 (s, 2H)

Example 9

Synthesis of N—N'-bis(4-(1,9-di(1,1,1,3,3,5,5-heptamethyl trisiloxanyl)nonane-5-yloxy)phenyl) perylene-3,4,9,10-tetracarboxylic acid bisimide (compound (2-46) ((2), m=0, n=3))

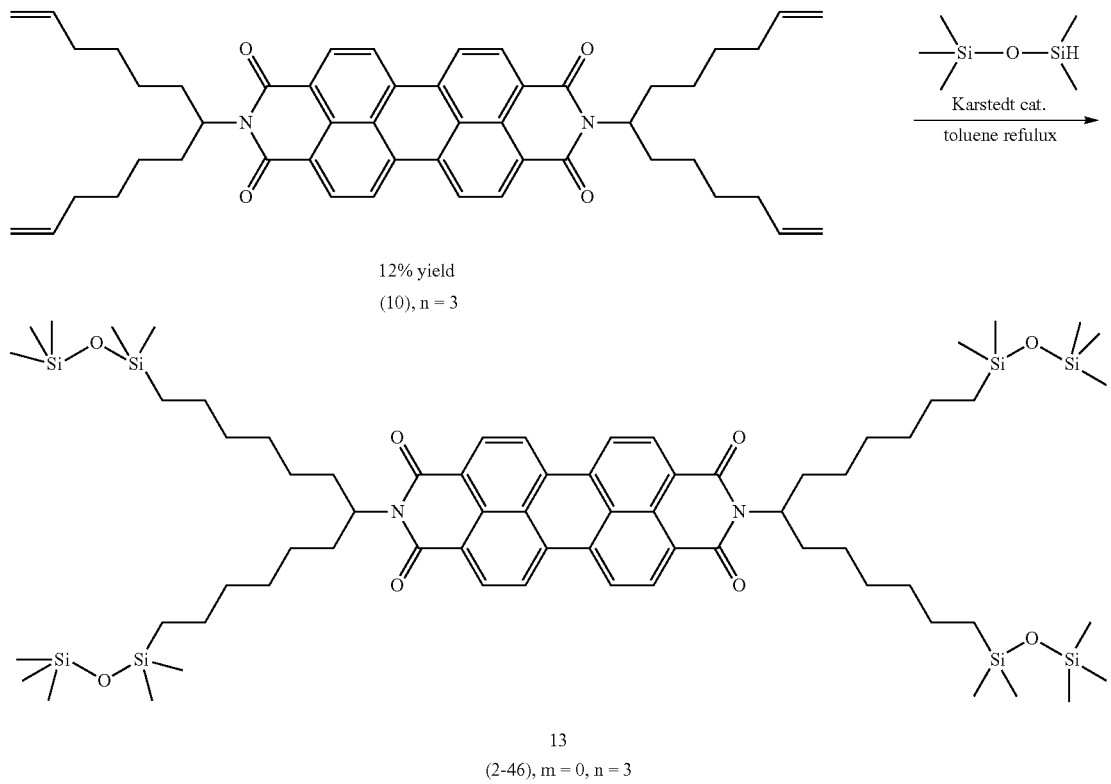

Scheme 2-3-5

12% yield
(10), n = 3

13
(2-46), m = 0, n = 3

A 200 ml-capacity three neck flask containing a stirring bar and connected to a condenser was sufficiently dried. Then, a nitrogen atmosphere was established in the flask, N—N'-di (1,12-tridecadiene-7-yl)perylene-3,4,9,10,tetracarboxylic acid bisimide (10) (n=3) (0.3 g, 4.35×10$^{-4}$ mol) and 1,1,1,3,3,pentamethyl siloxane (0.32 g, 21.75×10$^{-4}$ mol) were introduced into the flask, and toluene (50 ml) was further added to the mixture thus obtained to dissolve them. The solution thus obtained was stirred while placing the flask in an oil bath (180° C.). When the solution became a homogeneous mixture, a Karstedt catalyst (10 µl) was added to the solution, and the mixture thus obtained was further stirred for half a day. When generation of an intended compound was recognized by thin-layer chromatography, the solvent was distilled off under reduced pressure, and the compound was purified by flash chromatography on silica gel (hexane:ethyl acetate=20:1), (hexane:ethyl acetate=10:1), (hexane:ethyl acetate=5:1) and re-precipitated with CH$_2$Cl$_2$. Thus, intended N—N'-bis (4-(1,9,-di(1,1,1,3,3,5,5-heptamethyl trisiloxanyl)nonane-5-yloxy)phenyl)perylene-3,4,9,10-tetracarboxylic acid bisimide (compound (2-46) ((2), m=0, n=3)) was obtained. Values obtained by instrumental analysis values of the compound (2-46) are shown below.

Values obtained by instrumental analysis of compound (2-46):

$^1$H NMR (400 MHz, CDCl$_3$)

δ=8.64 (d, br, 4H), 8.62 (d, 4H, 7.6 Hz), 5.18 (m, 2H), 2.3-2.2 (m, 4H), 1.9-1.8 (m, 4H), 1.4-1.8 (m, 7H), 1.2-1.4 (m, 22H), 0.8 (t, 3H, 6.0 Hz), 0.4 (m, 8H), −0.01 (s, 30H), −0.02 (s, 30H), IR (ATR): ν=2922, 1649, 1337, 1249, 1044, 835 cm$^{-1}$

Exact Mass: 1338.70; Molecular Weight: 1340.38 m/z [M+]: 1337.97 (100%), 1338.98 (69%), 1339.93 (57%), 1340.94 (56%), 1341.93 (57%)

Figure 13:
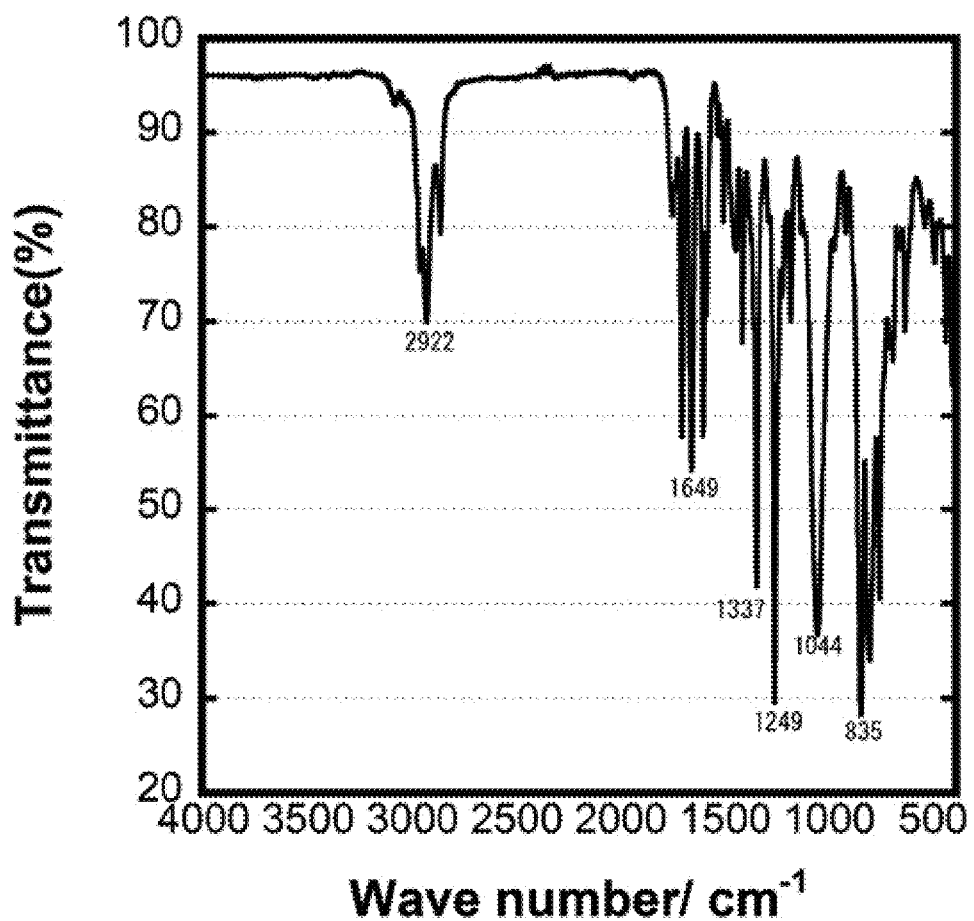
FIG. 13 is an IR spectrum of a compound (2-46) ((2), m=0, n=3) produced in Example 9.

A graph of FIG. 13 shows an IR spectrum of the compound (2-46). In FIG. 13, the horizontal axis indicates a wave number (cm$^{-1}$), and the vertical axis indicates a transmittance (%).

Example 10

Production of liquid crystal cell of N—N'-bis(4-(1,9-di(1,1,1,3,3,5,5-heptamethyl trisiloxanyl)nonane-5-yloxy)phenyl)perylene-3,4,9,10-tetracarboxylic acid bisimide (Compound (2-46) ((2), m=0, n=3))

Figure 14A:
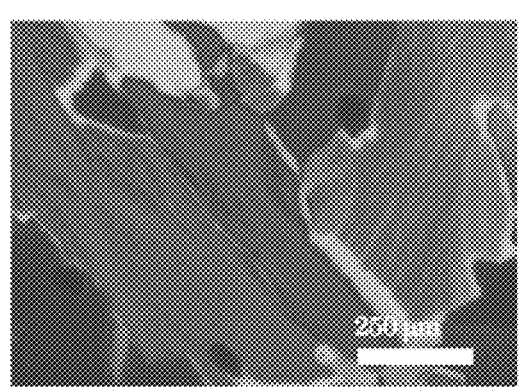
FIGS. 14A and 14B are polarization microscope photographs of a liquid crystal sample of a compound (2-46) produced in Example 10. The polarization microscope photographs of FIGS. 14A and 14B were taken at room temperature.
Figure 14B:
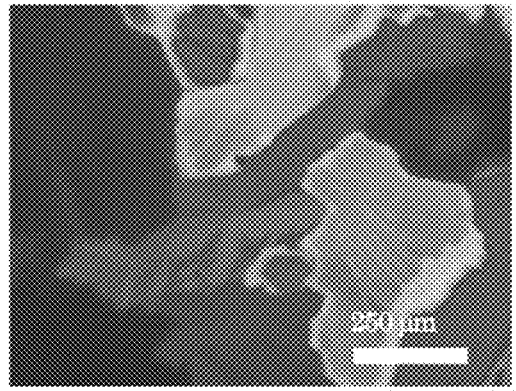

A liquid crystal cell was produced in the same manner as in Example 4 except that the compound (2-46) was used as substitute for the compound (2-1), and a liquid crystal phase thereof was identified by observing the liquid crystal cell with a polarization microscope. FIGS. 14A and 14B show results of the observation with a polarization microscope. FIGS. 14A and 14B are both polarization microscope photographs taken at room temperature. As shown in FIGS. 14A and 14B, it was observed that the compound (2-46) was in a liquid crystal phase at room temperature. When the liquid crystal cell was observed with a polarization microscope under temperature variable conditions, the liquid crystal phase was transferred into an isotropic phase at 97° C. in an elevated temperature process, and the isotropic phase was transferred into the liquid crystal phase at 75° C. in a cooling process.

X-Ray Diffraction and the Like of N—N'-bis(4-(1,9,-di(1,1,1,3,3,5,5-heptamethyltrisiloxanyl)nonane-5-yloxy)phenyl)perylene-3,4,9,10-tetracarboxylic acid bisimide (Compound (2-46) ((2), m=0, n=3))

Figure 15:
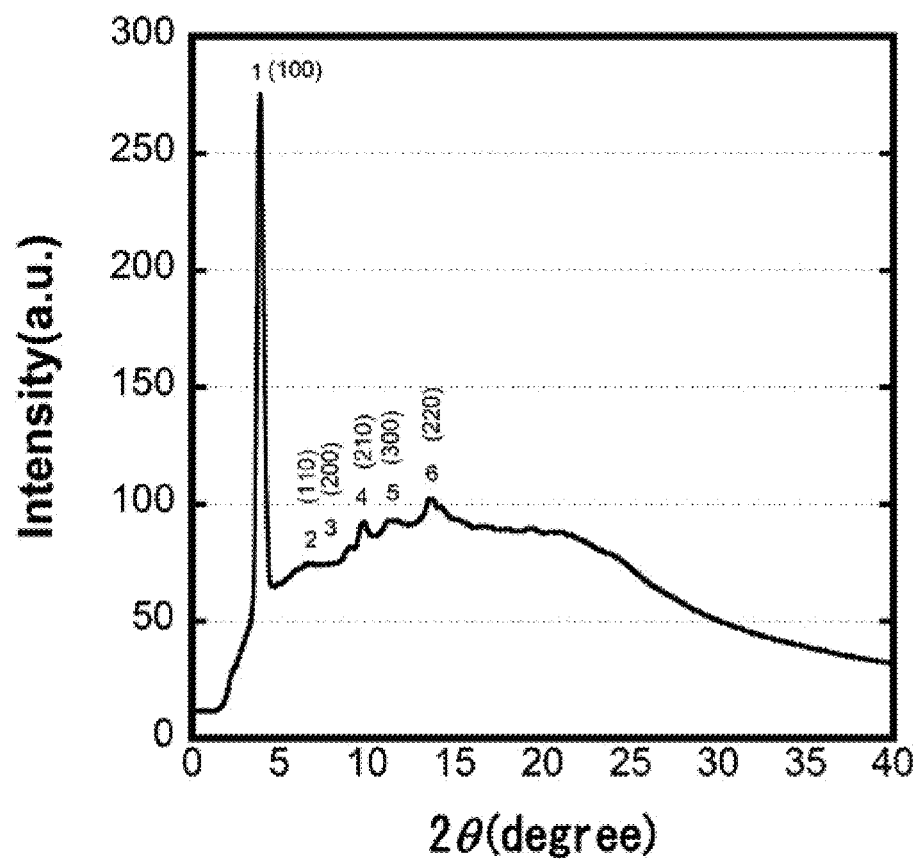
FIG. 15 is a graph showing an X-ray diffraction (XRD) pattern of a compound (2-46) at room temperature.

A graph of FIG. 15 shows an X-ray diffraction (XRD) pattern of the compound (2-46) ((2), m=0, n=3) at room temperature. In FIG. 15, the horizontal axis indicates 2θ (°), and the vertical axis indicates a peak intensity (relative value). Lattice constants calculated from the pattern of FIG. 15 are shown in Table 8 below.

TABLE 8

|   | X | θ | rad | d | lattice constant |
|---|---|---|---|---|---|
| 1 | 3.916 | 1.958 | 0.034174 | 2.25628E-09 | (100) |
| 2 | 6.072 | 3.036 | 0.052988 | 1.45553E-09 | (110) |
| 3 | 9.064 | 4.532 | 0.079098 | 9.75627E-10 | (200) |
| 4 | 9.81 | 4.905 | 0.085608 | 9.01597E-10 | (210) |
| 5 | 11.66 | 5.83 | 0.101753 | 7.5893E-10 | (300) |
| 6 | 13.64 | 6.82 | 0.119031 | 6.49176E-10 | (220) |

From the lattice constants (Table 8) of diffraction peaks observed in an XRD diffraction pattern shown in FIG. 15, it was considered that a liquid crystal phase of the compound (2-46) ((2), m=0, n=3) was a hexagonal columnar phase. Further, from the XRD pattern shown in FIG. 15, it was observed that a column gap was d=2.2 nm, which was shorter than the molecular length. This shows that an interaction among oligosiloxane chains is important for formation of a columnar phase. Furthermore, according to the XRD pattern of FIG. 15, a molecular orientational order was not present in the column.

Figure 16:
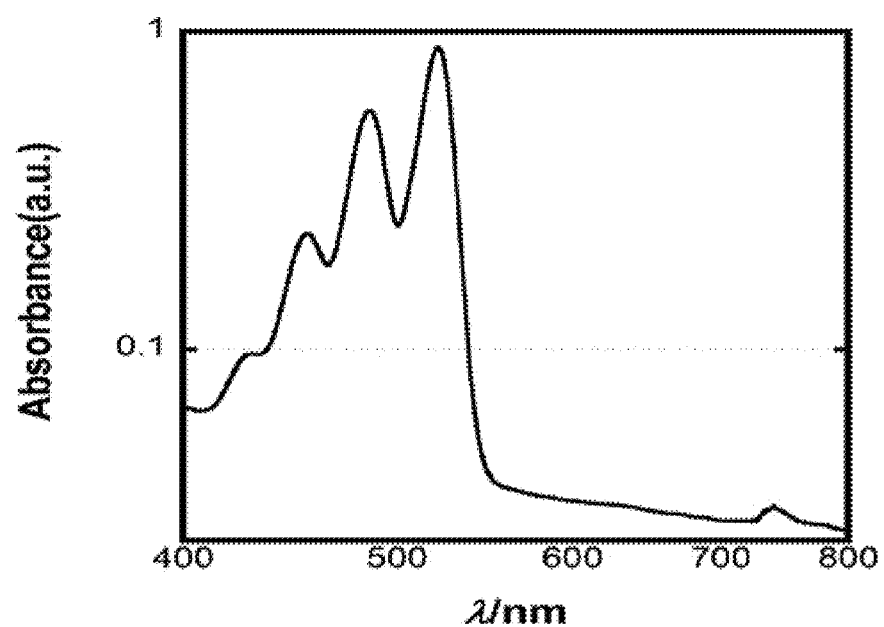
FIG. 16 is an ultraviolet-visible absorption spectrum of a compound (2-46) at room temperature.
Figure 17:
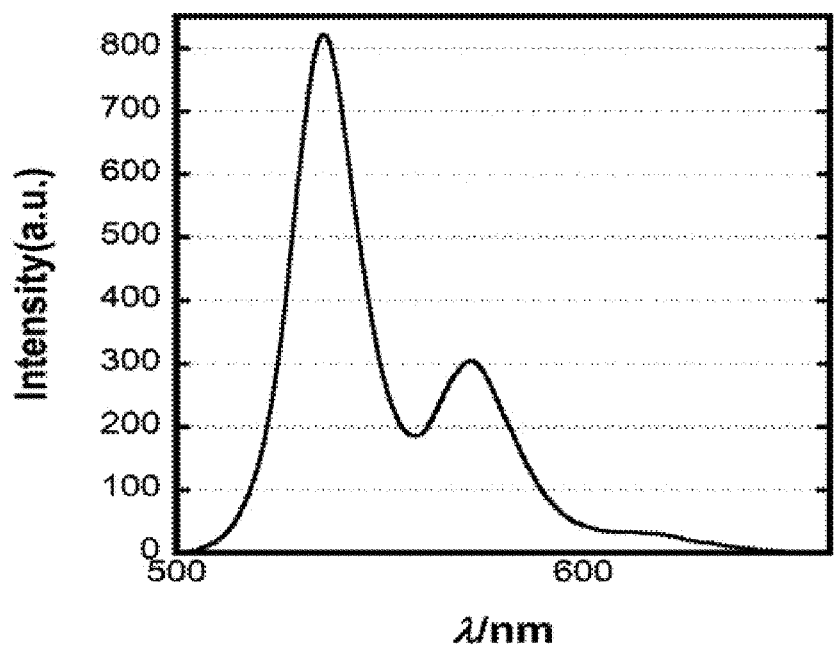
FIG. 17 is a fluorescence spectrum of a compound (2-46) at room temperature.

FIG. 16 shows an ultraviolet-visible absorption spectrum of the compound (2-46) at room temperature. In FIG. 16, the horizontal axis indicates a wavelength (nm), and the vertical axis indicates an absorbance (relative value). FIG. 17 shows a fluorescence spectrum of the compound (2-46) at room temperature. In FIG. 17, the horizontal axis indicates a wavelength (nm), and the vertical axis indicates a fluorescence intensity (relative value). As shown in FIGS. 16 and 17, a perylene skeleton-derived specific peak appeared in each of the absorption spectrum and the fluorescence spectrum, and this supports a structure of the compound (2-46) with the above-described $^1$HNMR, MS, and IR.

Charge Transport Properties of N—N'-bis(4-(1,9,-di(1,1,1,3,3,5,5-heptamethyl trisiloxanyl)nonane-5-yloxy)phenyl)perylene-3,4,9,10-tetracarboxylic acid bisimide (Compound (2-46) ((2), m=0, n=3))

Figure 18:
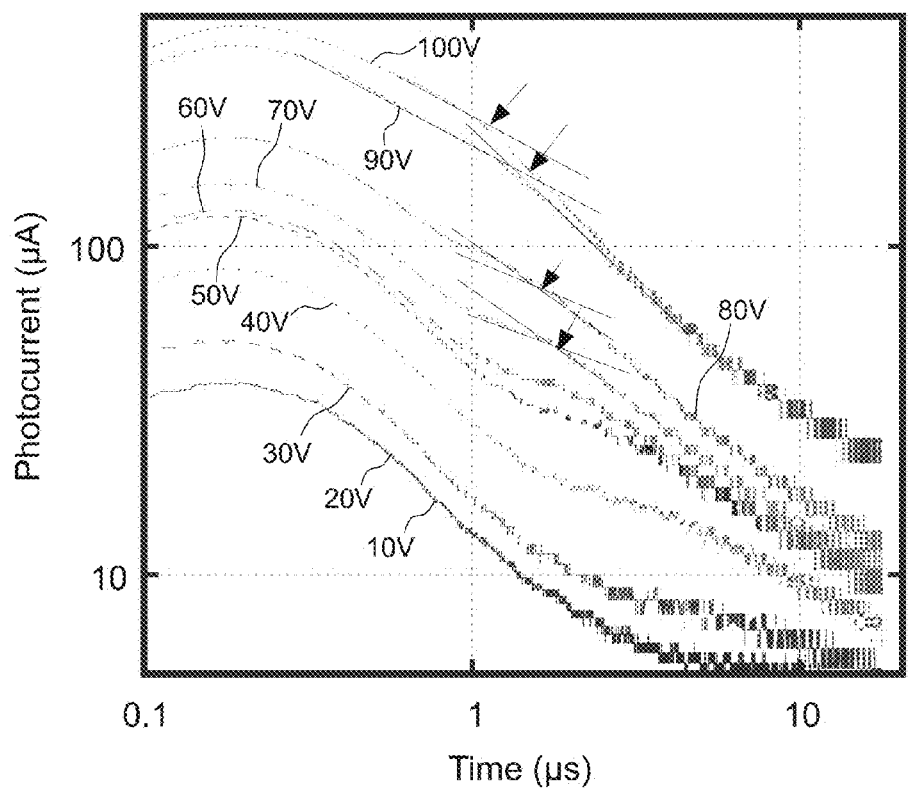
FIG. 18 is a graph showing a result of transient photocurrent measurement of a compound (2-46) by a TOF method.

Charge transport properties (carrier mobility properties) of the liquid crystal compound (2-46) ((2), m=0, n=3) were measured through transient photocurrent measurement by a Time-of-Flight method using the liquid crystal cell produced in Example 10. The transient photocurrent measurement by a Time-of-Flight method was performed in the same manner as in the measurement of charge transport properties (carrier mobility properties) of the liquid crystal compound (2-1) ((2), m=1, n=1). The thickness of a sample of the liquid crystal compound (2-46) ((2), m=0, n=3) was 9 μm. The measurement temperature was room temperature (25° C.), and the measurement was performed while changing an applied voltage from 10 V to 100 V by 10 V increments. The graph of FIG. 18 shows the result of the measurement. In FIG. 18, the horizontal axis indicates time (μs), and the vertical axis indicates a photocurrent (μA). As shown in FIG. 18, in the same time of flight, the higher the applied voltage was, the higher the photocurrent flowed. In FIG. 18, each arrow indicates a transient current. The maximum electron mobility of the liquid crystal compound (2-46) ((2), m=0, n=3), calculated by the TOF method in FIG. 18 was $1\times10^{-2}$ cm/Vs. This electron mobility of the liquid crystal compound (2-46) was about 10 times higher than that of the liquid crystal compound (2-1) and was higher than those of general amorphous and a general organic semiconductor. Even though the liquid crystal compound (2-46) in the liquid crystal cell of Example 10 did not have a molecular orientational order in the column as mentioned above, such really high electron mobility was obtained. It is expected that the electron mobility of the liquid crystal compound (2-46) would be increased further by controlling an orientation thereof or purifying it.

Example 11

Synthesis of N—N'-bis(1,9-di(1,1,1,3,5,5,5-heptamethyl trisiloxane-3-yl)nonane-5-yl)perylene-3,4,3,9,10-tetracarboxylic acid bisimide (Compound (4-1) ((4), m=0, n=1))

A compound (4-1) ((4), m=0, n=1) was synthesized according to the following scheme 3-2. The compound 10 was synthesized in the same manner as in Reference Examples 2 and 3 (synthesis of starting material in Example 2).

Scheme 3-2

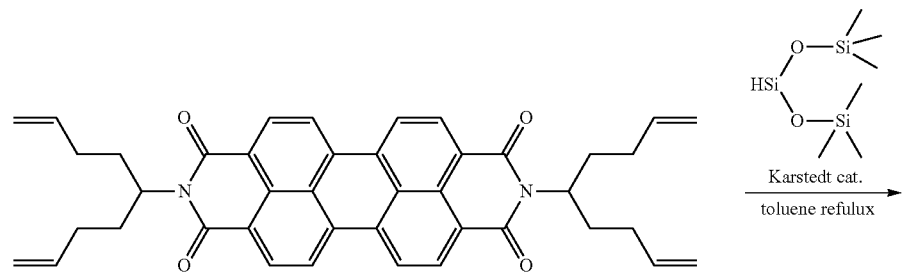

(10), n = 1

-continued

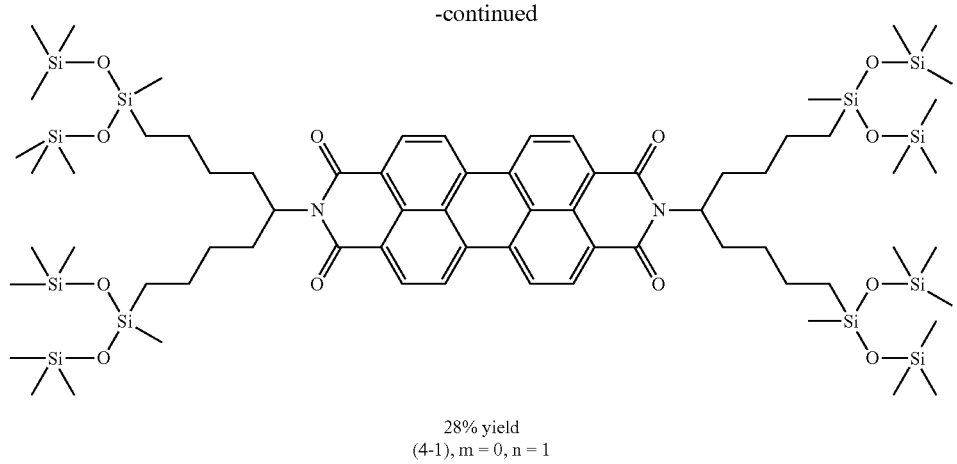

28% yield
(4-1), m = 0, n = 1

A 200 ml-capacity three neck flask containing a stirring bar and connected to a condenser was sufficiently dried. Then, a nitrogen atmosphere was established in the flask, perylene-3,4,9,10-tetracarboxylic acid bis(1,8-nonadiene-5-ylimide) (compound (10), m=1, n=1) (0.5 g, 7.89×10$^{-4}$ mol), and 1,1,1,3,5,5,5-heptamethyl siloxane (0.9 g, 39.45×10$^{-4}$ mol) were introduced into the flask, and toluene (50 ml) was further added to the mixture thus obtained to dissolve them. The mixture thus obtained was stirred while placing the flask in an oil bath (180° C.). When the mixture became a homogeneous mixture, a Karstedt catalyst (10 μl) was added to the mixture, which was then further stirred for half a day. When a reaction progress was recognized by thin-layer chromatography, the solvent was distilled off under reduced pressure, and the mixture was purified by flash chromatography on silica gel (hexane:ethyl acetate=20:1), (hexane:ethyl acetate=10:1), (hexane:ethyl acetate=5:1) and re-precipitated with CH$_2$Cl$_2$. Thus, N—N'-bis(1,9-di(1,1,1,3,5,5,5-heptamethyltrisiloxane-3-yl)nonane-5-yl)perylene-3,4,3,9,10-tetracarboxylic acid bisimide (compound (4-1) ((4), m=0, n=1)) (0.34 g, 2.23×10- mol, yield: 28%) was obtained as an intended compound. Values obtained by instrumental analysis of the compound (4-1) are shown below.

Values obtained by instrumental analysis of compound (4-1):

$^1$H NMR (400 MHz, CDCl$_3$)

δ=8.7 (d, br, 4H), 8.6 (d, 4H, J=8 Hz), 5.18 (m, 2H), 2.18-2.224 (m, 4H), 1.8-1-7 (m, 4H), 1.2-1.4 (m, 18H), 0.4 (t, 8H, 8.8 Hz), 0.1 (s, 83H), IR (ATR): ν=2972, 1708, 1656, 1338, 1256, 1050, 834 cm$^{-1}$

Exact Mass: 1522.65; Molecular Weight: 1524.78 m/z [M$^+$]: 1521.88 (100%), 1522.86 (78%), 1523.90 (65%), 1524.87 (50%), 1526.44 (25%)

Figure 19:
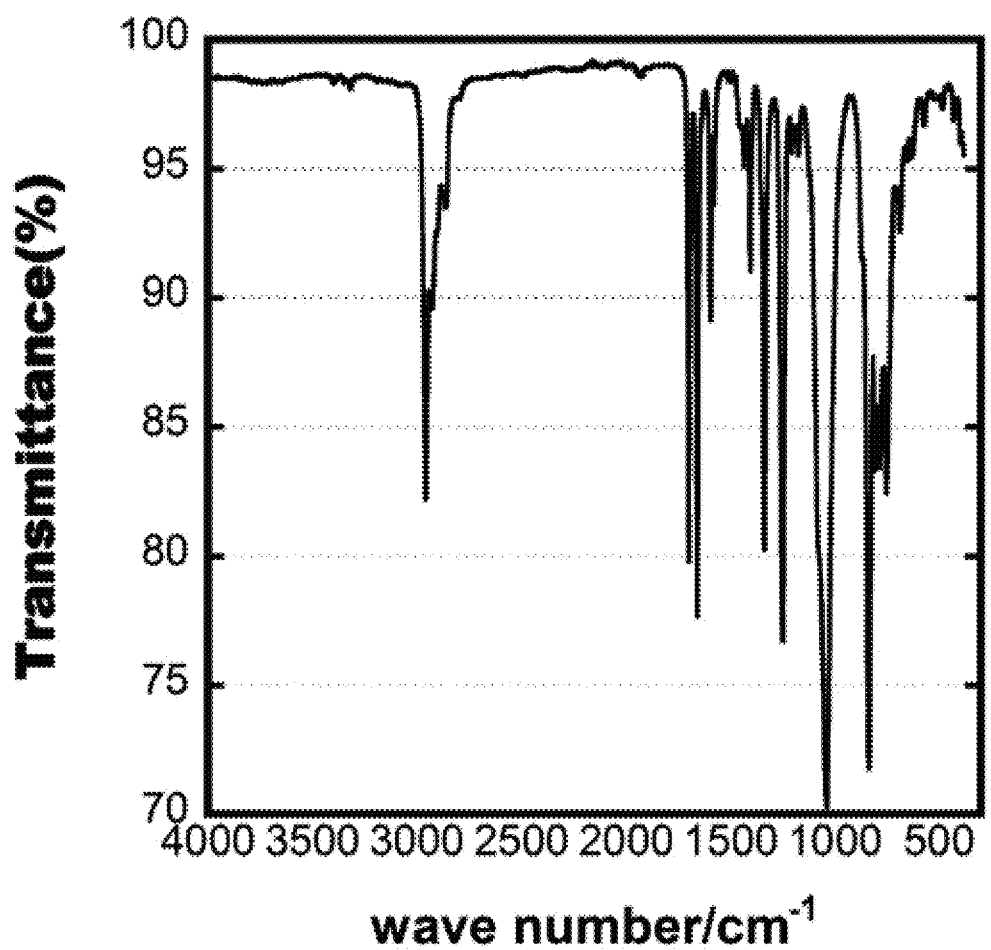
FIG. 19 is an IR spectrum of a compound (4-1) ((4), m=0, n=1) produced in Example 11.

FIG. 19 shows an IR spectrum of the compound (4-1) at room temperature. In FIG. 19, the horizontal axis indicates a wave number (cm$^{-1}$), and the vertical axis indicates a transmittance (%).

Example 12

Production of liquid crystal cell of N—N'-bis(1,9-di(1,1,1,3,5,5,5-heptamethyl trisiloxane-3y)nonane-5-yl)perylene-3,4,3,9,10-tetracarboxylic acid bisimide (Compound (4-1) ((4), m=0, n=1))

Figures 20A, 20B:
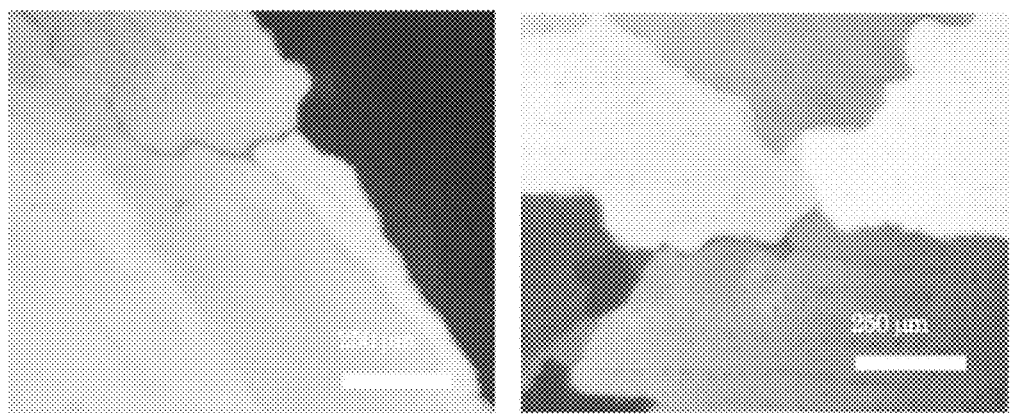
FIGS. 20A and 20B are polarization microscope photographs of a liquid crystal sample of a compound (4-1) produced in Example 12. The polarization microscope photographs of FIGS. 20A and 20B were taken at room temperature.

A liquid crystal cell was produced in the same manner as in Example 4 except that the compound (4-1) was used as substitute for the compound (2-1), and a liquid crystal phase thereof was identified by an observation with a polarization microscope. FIGS. 20A and 20B show results of the observation with a polarization microscope. Both of FIGS. 20A and 20B are polarization microscope photographs taken at room temperature. As shown in FIGS. 20A and 20B, it was recognized from domains observed by a polarization microscope that the compound (4-1) was in a liquid crystal phase at room temperature. When the liquid crystal cell was observed with a polarization microscope in the same manner as described above under temperature variable conditions, the liquid crystal phase was transferred to an isotropic phase at 132° C. in an elevated temperature process, and the isotropic phase was transferred to a liquid crystal phase at 130° C. in a cooling process. Further, the liquid crystal phase was maintained even when the liquid crystal cell was cooled to room temperature.

X-Ray Diffraction and the Like of N—N'-bis(1,9-di(1,1,1,3,5,5,5-heptamethyltrisiloxane-3-yl)nonane-5-yl)perylene-3,4,3,9,10-tetracarboxylic acid bisimide (Compound (4-1) ((4), m=0, n=1))

Figure 21:
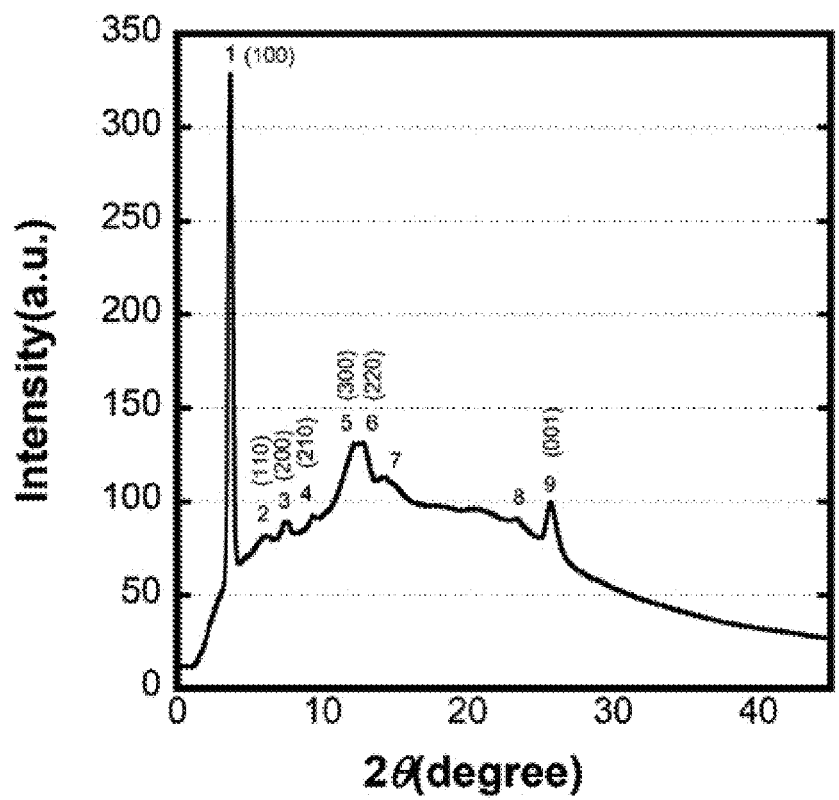
FIG. 21 is a graph showing an X-ray diffraction (XRD) of a compound (4-1) at room temperature.

A graph of FIG. 21 shows an X-ray diffraction (XRD) pattern of the compound (4-1) ((4), m=0, n=1) at room temperature. In FIG. 21, the horizontal axis indicates 2θ (°), and the vertical axis indicates a peak intensity (relative value). Lattice constants calculated from the pattern of FIG. 21 are shown in Table 9 below.

TABLE 9

| | X | θ | rad | d | lattice constant |
|---|---|---|---|---|---|
| 1 | 3.696 | 1.848 | 0.032254 | 2.39E-09 | (100) |
| 2 | 6.072 | 3.036 | 0.052988 | 1.46E-09 | (110) |
| 3 | 7.48 | 3.74 | 0.065275 | 1.18E-09 | (200) |
| 4 | 9.416 | 4.708 | 0.08217 | 9.39E-10 | (210) |
| 5 | 12.364 | 6.182 | 0.107896 | 7.16E-10 | (300) |
| 6 | 12.804 | 6.402 | 0.111736 | 6.91E-10 | (220) |
| 7 | 14.168 | 7.084 | 0.123639 | 6.25E-10 | |
| 8 | 23.32 | 11.66 | 0.203505 | 3.81E-10 | |
| 9 | 25.696 | 12.848 | 0.22424 | 3.47E-10 | (001) |

From the lattice constants (Table 9) of diffraction peaks observed in an XRD diffraction pattern shown in FIG. 21, it was considered that a liquid crystal phase of the compound (4-1) ((4), m=0, n=1)) was a hexagonal columnar phase. Further, from the XRD pattern shown in FIG. 21, it was observed that a column gap was d=3.7 nm, which was shorter than the molecular length. This shows that an interaction among oligosiloxane chains is important for formation of a columnar phase. Furthermore, as shown in FIG. 21, a diffraction peak corresponding to an orientational order in the column appeared at 25.7°. Thus, it was observed that the stacking distance in the column was 3.47 Å, and a structure that enables high-speed electron transport was formed.

Figure 22:
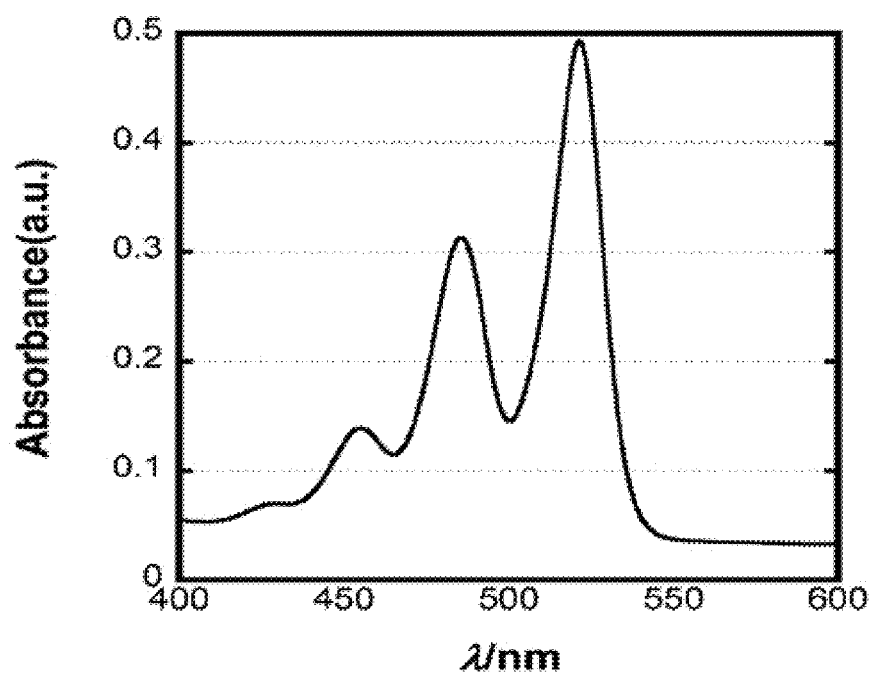
FIG. 22 is an ultraviolet-visible absorption spectrum of a compound (4-1) at room temperature.
Figure 23:
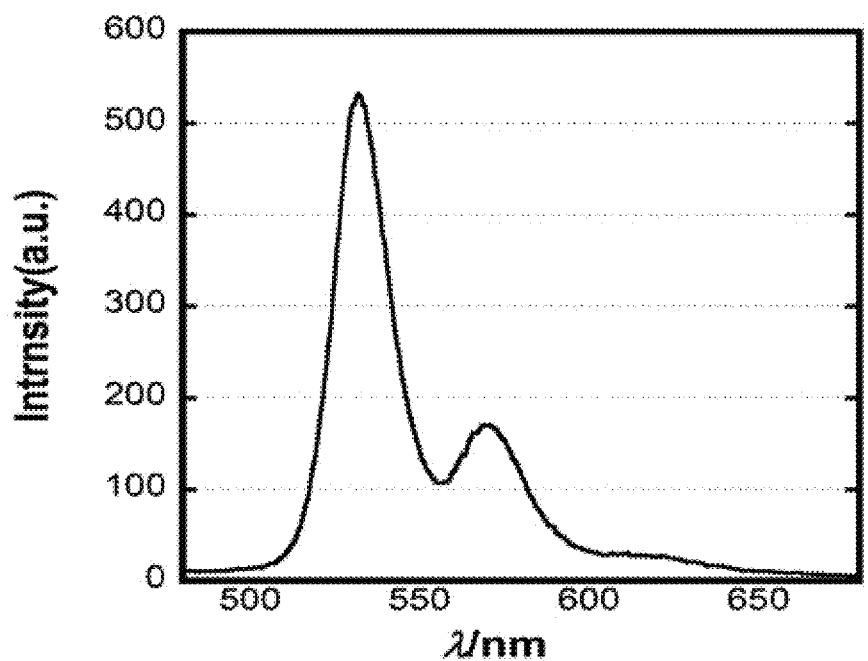
FIG. 23 is a fluorescence spectrum of a compound (4-1) at room temperature.

FIG. 22 shows an ultraviolet-visible absorption spectrum of the compound (4-1) at room temperature. In FIG. 22, the horizontal axis indicates a wavelength (nm), and the vertical axis indicates an absorbance (relative value). FIG. 23 shows a fluorescence spectrum of the compound (4-1) at room temperature. In FIG. 23, the horizontal axis indicates a wavelength (nm), and the vertical axis indicates a fluorescence intensity (relative value). As shown in FIGS. 22 and 23, a perylene skeleton-derived specific peak appeared in each of the absorption spectrum and the fluorescence spectrum, and this supports a structure of the compound (4-1) with the above-described $^1$HNMR, MS, and IR.

Charge Transport Properties of N—N'-bis(1,9-di(1,1,1,3,5,5,5-heptamethyltrisiloxane-3-yl)nonane-5-yl)perylene-3,4,3,9,10-tetracarboxylic acid bisimide (Compound (4-1) ((4), m=0, n=1))

Charge transport properties (carrier mobility properties) of the liquid crystal compound (4-1) ((4), m=0, n=1) were measured through transient photocurrent measurement by a Time-of-Flight method using the liquid crystal cell produced in Example 12. The transient photocurrent measurement by a Time-of-Flight method was performed in the same manner as in the measurement of charge transport properties (carrier mobility properties) of the liquid crystal compound (2-1) ((2), m=1, n=1). The thickness of a sample of the liquid crystal compound (4-1) ((4), m=0, n=1) was 9 μm. The measurement temperature was room temperature (25° C.), and the measurement was performed while changing an applied voltage from 10 V to 100 V by 10 V increments. It is possible to obtain a higher electron mobility of the liquid crystal compound (4-1) by controlling an orientation thereof or purifying it.

N—N'-bis(4-(1,9,-di(1,1,1,3,3,5,5-heptamethyltrisiloxanyl)nonane-5-yloxy)phenyl)perylene-3,4,9,10-tetracarboxylic acid bisimide (Compound (5-1) ((5), m=1, n=1))

A compound (5-1) ((5), m=1, n=1)) was synthesized according to the following scheme 4-2 (Example 13).

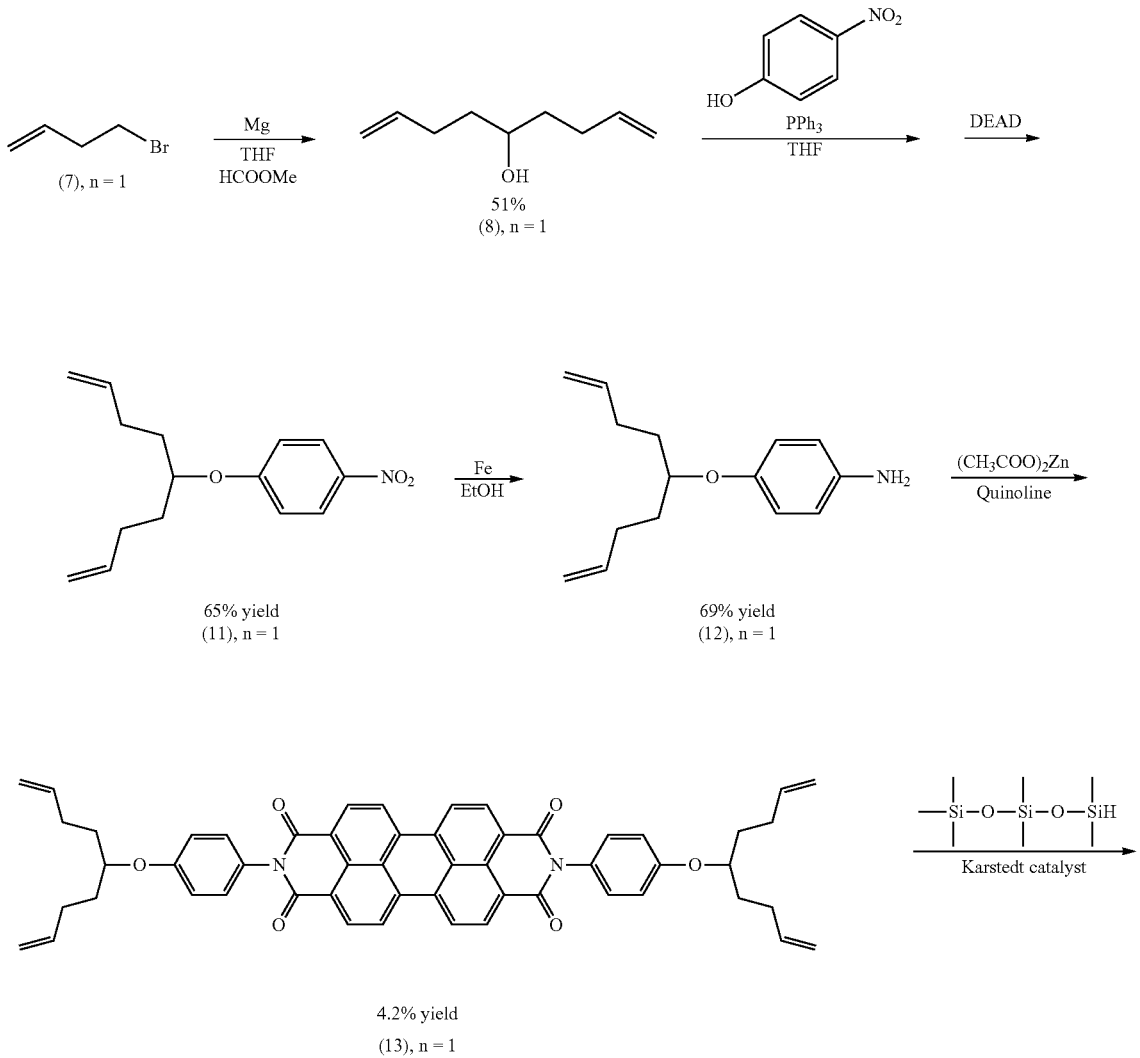

Scheme 4-2

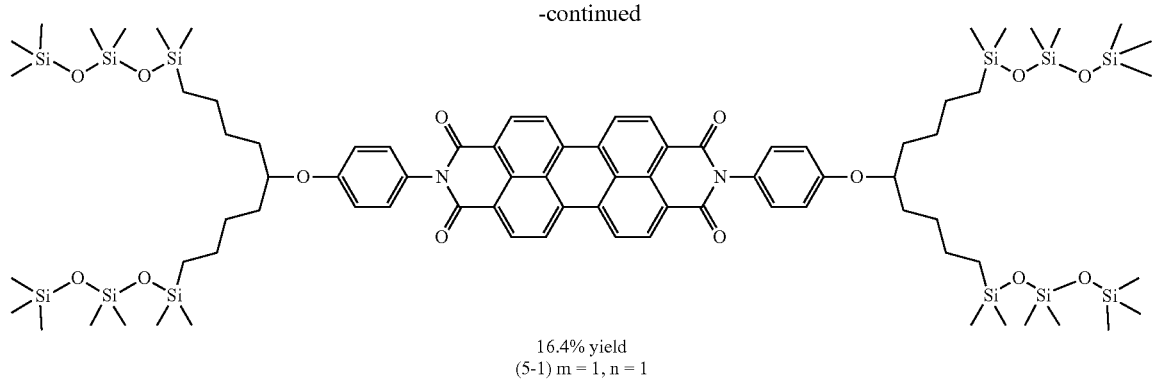

16.4% yield
(5-1) m = 1, n = 1

Reference Example 8

Synthesis of 1,8-nonadiene-5-ol (8)

Scheme 4-2-1

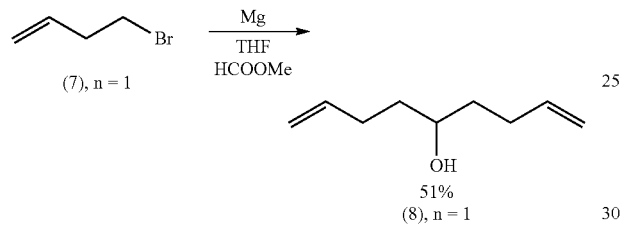

A 300 ml-capacity three neck flask containing a stirring bar and Mg (8 g, 16.3 mmol) and connected to a condenser was sufficiently dried. Then, a nitrogen atmosphere was established in the flask, and diethyl ether (24.5 ml) and $I_2$ were introduced into the flask. When a solution of 1-bromo-3-butene (7) (22 ml, 16.3 mmol) in diethyl ether (24.5 ml) was slowly added to the brown suspension thus obtained, a reaction started, and a color of $I_2$ disappeared. After generation of a Grignard reagent, HCOOMe (9.78 ml, 16.3 mmol) was slowly dropped into the flask, and the mixture thus obtained was stirred for 30 minutes. Subsequently, when generation of alcohol was recognized by thin-layer chromatography (hexane:ethyl acetate=10:1), diluted hydrochloric acid was added to the mixture to stop the reaction. After cooling the mixture, an organic layer was separated and extracted with ethyl acetate. This organic layer was dehydrated over $Na_2SO_4$ and filtered. The solvent was distilled off, and the organic layer was purified by flash chromatography on silica gel (hexane:ethyl acetate=10:1). Thus, 1,8-nonadiene-5-ol (8) (11.613 g, 8.3 mmol, yield: 51%) was obtained as an intended compound.

Reference Example 9

Synthesis of 1-nitro-4-(1,8-nonadiene-5-yloxy)benzene (11)

Scheme 4-2-2

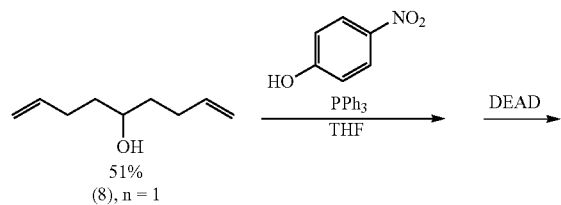

-continued

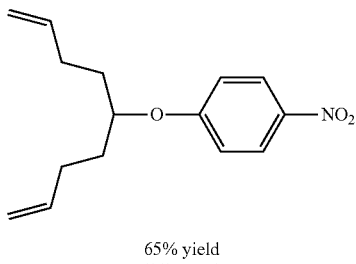

65% yield
(11), n = 1

A 300 ml-capacity three neck flask containing a stirring bar and connected to a condenser was sufficiently dried. Then, a nitrogen atmosphere was established in the flask, and 1,8-nonadiene-5-ol (8) (3.72 g, 2.66 mmol), $PPh_3$ (6.98 g, 2.66 mmol), and 4-nitrophenol (4.43 g, 3.19 mmol) were introduced into the flask. Dried THF (50 ml) was further added to the mixture, the mixture thus obtained was stirred at room temperature, DEAD (12.2 ml, 3.19 mmol) was then dropped into the flask, and the mixture thus obtained was stirred for 5 hours. When generation of ether was recognized by thin-layer chromatography (hexane:ethyl acetate=10:1), the solvent was distilled off under reduced pressure, the mixture was purified by flash chromatography on silica gel (hexane:ethyl acetate=10:1). Thus, 1-nitro-4-(1,8-nonadiene-5-yloxy)benzene (11) (4.731 g, 1.7 mmol, yield: 65%) was obtained as an intended compound. $^1$HNMR values of 1-nitro-4-(1,8-nonadiene-5-yloxy)benzene (11) are shown below.

$^1$HNMR values of 1-nitro-4-(1,8-nonadiene-5-yloxy)benzene (11):

$^1$H NMR (400 MHz, $CDCl_3$) δ=8.13 (dd, 2H, $J_1$=1.6 Hz, $J_2$=9.6 Hz), 6.89 (dd, 1H, J=1.6 Hz, $J_2$=9.2 Hz), 5.75 (m, 4H), 4.98 (m, 1H), 4.95 (m, 1H), 4.93 (m, 1H), 4.4 (m, 2H), 2.1 (m, 4H), 1.75 (m, 3H)

Reference Example 10

Synthesis of 1-amino-4(1,8-nonadiene-5-yloxy)benzene (12)

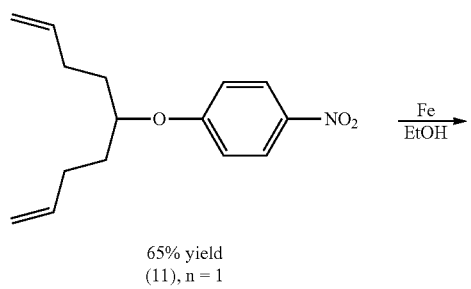

Scheme 4-2-3

65% yield
(11), n = 1

A 300 ml-capacity three neck flask containing a stirring bar and connected to a condenser was sufficiently dried. Then, a nitrogen atmosphere was established in the flask. 1-nitro-4-(1,8-nonadiene-5-yloxy)benzene (11) (4.01 g, 1.4 mmol), an iron powder (3.13 g, 5.6 mmol), and ethanol (50%, 10 ml) were introduced into the flask, and the mixture thus obtained was started to be stirred while heating the flask in an oil bath. Further, HCl (0.52 ml) and ethanol (50%, 2.5 ml) were slowly added to the mixture, which was then stirred for 2 hours. Thereafter, an aqueous sodium hydroxide solution was added to the mixture to stop the reaction, and an organic layer was extracted with ethyl acetate. This organic layer was dried over $Na_2SO_4$ and filtered, a solvent was distilled of under reduced pressure, and the organic layer was purified by flash chromatography on silica gel (hexane:ethyl acetate=10:1). Thus, 1-amino-4(1,8-nonadiene-5-yloxy)benzene (12) (2.39 g, $9.64 \times 10^{-3}$ mol, yield: 69%) was obtained as an intended compound.

Reference Example 11

Synthesis of N,N'-bis(4-(1,8-nonadiene-5-yloxy)phenyl)-perylene-3,4,9,10-tetracarboxylic acid bisimide (13) (n=1)

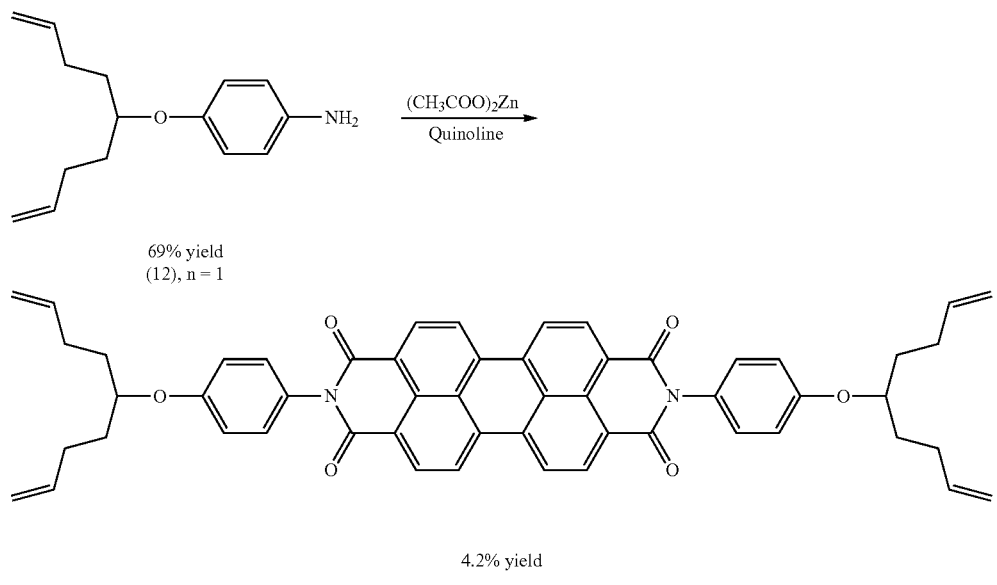

Scheme 4-2-4

69% yield
(12), n = 1

4.2% yield
(13), n = 1

-continued

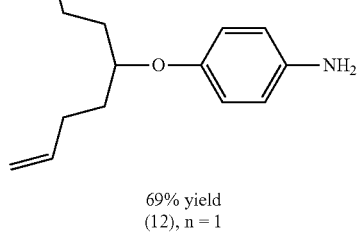

69% yield
(12), n = 1

A 200 ml-capacity three neck flask containing a stirring bar and connected to a condenser was sufficiently dried. Then, a nitrogen atmosphere was established in the flask, and 1-amino-4(1,8-nonadiene-5-yloxy)benzene (12) (2.08 g, $8.39 \times 10^{-3}$ mol), zinc acetate (0.63 g, $3.4 \times 10$ mol), perylene-3,4,9,10-tetracarboxylic acid bisimide (1.33 g, $3.4 \times 10$ mol), and quinoline (30 ml) were introduced into the flask. The mixture thus obtained was stirred for half a day while heating the flask in an oil bath (230° C.). When generation of a product was recognized by thin-layer chromatography, diluted hydrochloric acid was added to the mixture to stop the reaction. A mixture after adding diluted hydrochloric acid was suction-filtered with $CH_2Cl_2$, purified by flash chromatography on silica gel ($CH_2Cl_2$), and re-precipitated with methanol. Thus, N,N'-bis(4-(1,8-nonadiene-5-yloxy)phenyl)-perylene-3,4,9,10-tetracarboxylic acid bisimide (13)

(n=1) (0.288 g, $3.52 \times 10^{-4}$ mol, yield: 4.2%) was obtained as an intended compound. $^1$H NMR values of the compound (13) are shown below.

$^1$H NMR values of compound (13):
$^1$H NMR (400 MHz, CDCl$_3$)
δ=8.6 (dd, 4H, $J_1$=11.6 Hz, $J_2$=57.6 Hz), 7.1 (dd, 4H, $J_1$=7.2 Hz, $J_2$=86.8 Hz), 5.82 (m, 4H), 5.0 (ddt, 8H, J=4.4 Hz, $J_{2=12.4}$ Hz, $J_3$=19.2 Hz), 4.3 (m, 4H), 2.2 (m, 10H), 1.8 (m, 12H)

Example 13

Synthesis of N—N'-bis(4-(1,9,-di(1,1,1,3,3,5,5-heptamethyltrisiloxanyl)nonane-5-yloxy)phenyl)perylene-3,4,9,10-tetracarboxylic acid bisimide (5-1) ((5), m=1, n=1))

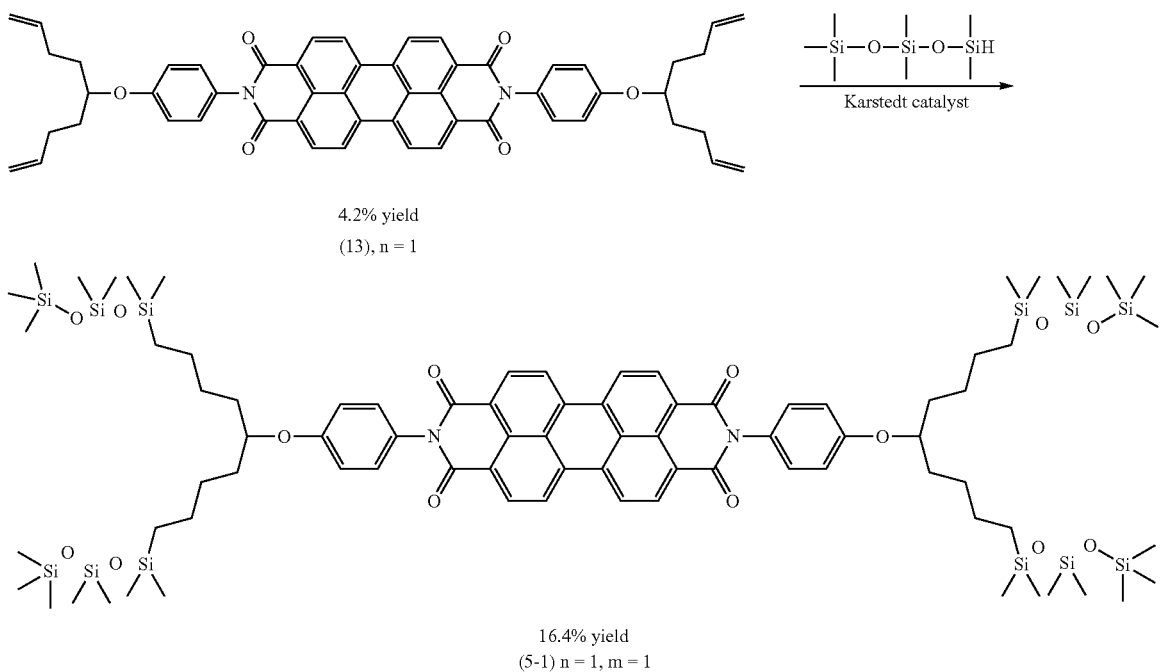

A 200 ml-capacity three neck flask containing a stirring bar and connected to a condenser was sufficiently dried. Then, a nitrogen atmosphere was established in the flask, and the compound (13) (0.3 g, $3.52 \times 10^{-4}$ mol) and 1,1,1,3,3,5,5-heptamethyl trisiloxane (0.39 g, $17.6 \times 10^{-4}$ mol) were introduced into the flask. Toluene (50 ml) was further added to the mixture thus obtained to dissolve them, which was then stirred while heating the flask in an oil bath (180° C.). When the mixture became a homogeneous mixture, a Karstedt catalyst (35 μl) was added to the mixture, which was then further stirred for half a day. When an intended product was recognized by thin-layer chromatography, the solvent was distilled off under reduced pressure, the product was purified by flash chromatography on silica gel (hexane:ethyl acetate=10:1), (hexane:ethyl acetate=5:1), dissolved in CH$_2$Cl$_2$, and re-precipitated with methanol. Thus, N—N'-bis(4-(1,9,-di(1,1,1,3,3,5,5-heptamethyltrisiloxanyl)nonane-5-yloxy)phenyl)perylene-3,4,9,10-tetracarboxylic acid bisimide (5-1) ((5), m=1, n=1)) (9.8 g, $5.76 \times 10^{-4}$ mol, yield: 16.4%) was obtained as an intended compound. Values obtained by instrumental analysis of the compound (5-1) are shown below.

Values obtained by instrumental analysis of compound (5-1):
$^1$H NMR (400 MHz, CDCl$_3$)
δ=8.52 (dd, 4H, $J_1$=7.6 Hz, $J_2$=49.6 Hz), 7.2 (dd, 4H, $J_1$=2.8 Hz, $J_2$=84.8 Hz), 1.5 (m, 15H), 0.5 (m, 44H), 0.1 (m, 67H), IR (ATR): ν=2964, 1707, 1667, 1506, 1255, 1034, 792 cm$^{-1}$ Exact Mass: 1706.71; Molecular Weight: 1708.97 m/z [M$^+$]: 1706.97 (66%), 1707.93 (50%), 1708.99 (100%), 1709.97 (76%), 1710.91 (65%)

Figure 24:
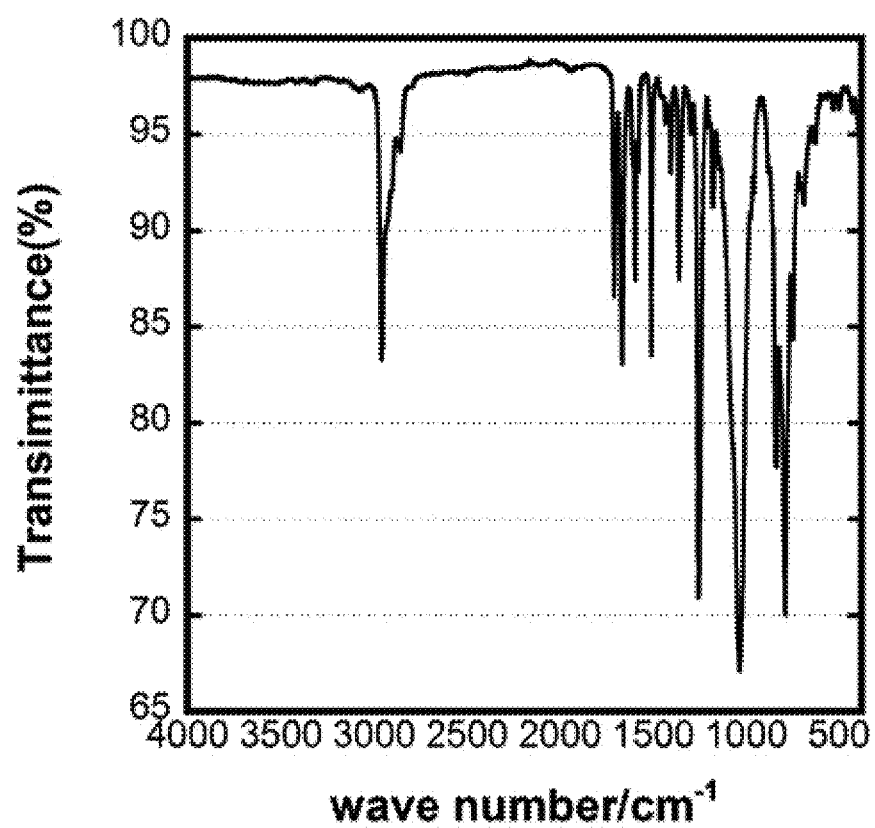
FIG. 24 is an IR spectrum of a compound (5-1) ((5), m=1, n=1) produced in Example 13.

A graph of FIG. 24 shows an IR spectrum of the compound (5-1). In FIG. 24, the horizontal axis indicates a wave number (cm$^{-1}$), and the vertical axis indicates a transmittance (%).

Example 14

Production of Liquid Crystal Cell of N—N'-bis(4-(1,9,-di(1,1,1,3,3,5,5-heptamethyltrisiloxanyl)nonane-5-yloxy)phenyl)perylene-3,4,9,10-tetracarboxylic acid bisimide (Compound (5-1) ((5), m=1, n=1))

A liquid crystal cell was produced in the same manner as in Example 4 except that the compound (5-1) was used as substitute for the compound (2-1), and a liquid crystal phase thereof was identified by an observation with a polarization microscope.

Figure 25:
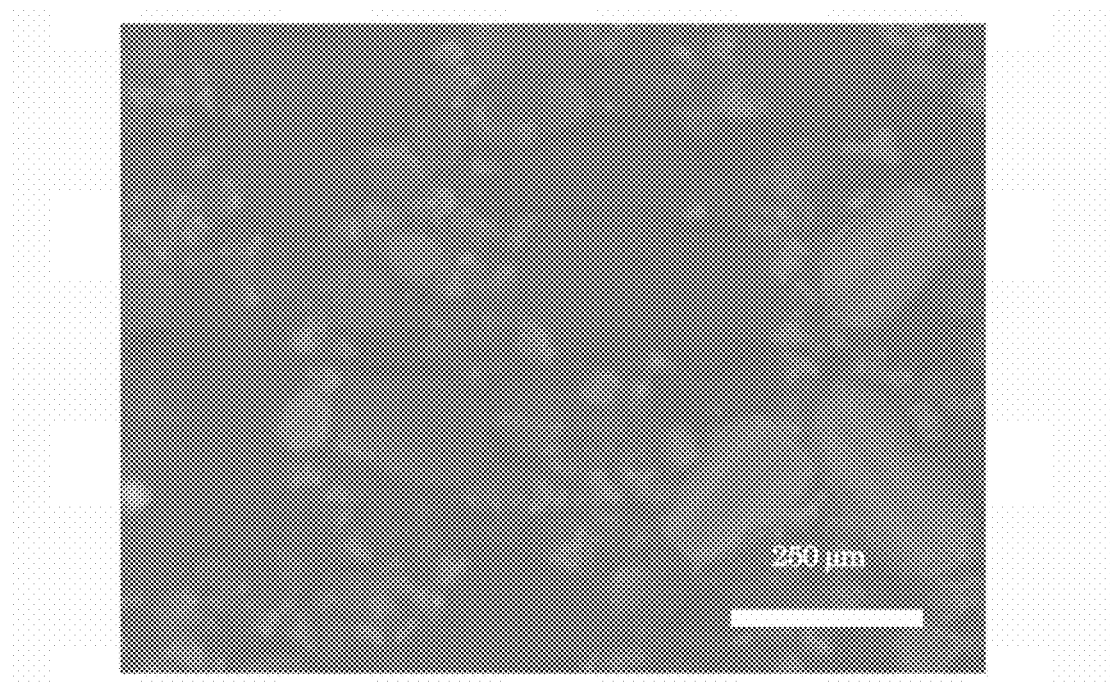
FIG. 25 is a polarization microscope photograph of a liquid crystal sample of a compound (5-1) produced in Example 14.

FIG. 25 shows a result of the observation with a polarization microscope. FIG. 25 is a polarization microscope photograph taken at room temperature. As shown in FIG. 25, it was observed that the compound (5-1) was in a liquid crystal phase at room temperature. When the liquid crystal cell was observed with a polarization microscope in the same manner as described above under temperature variable conditions, it was recognized that the liquid crystal phase was transferred to an isotropic phase at 241° C. in an elevated temperature process, and the isotropic phase was transferred to a liquid crystal phase at 246° C. in a cooling process. In the photograph of FIG. 25, domains having linear defects were observed. Thus, it was considered that the compound (5-1) was in a columnar phase at room temperature.

X-ray diffraction and the like of N—N'-bis(4-(1,9,-di (1,1,1,3,3,5,5-heptamethyltrisiloxanyl)nonane-5-yloxy)phenyl)perylene-3,4,9,10-tetracarboxylic acid bisimide (Compound (5-1) ((5), m=1, n=1))

Figure 26:
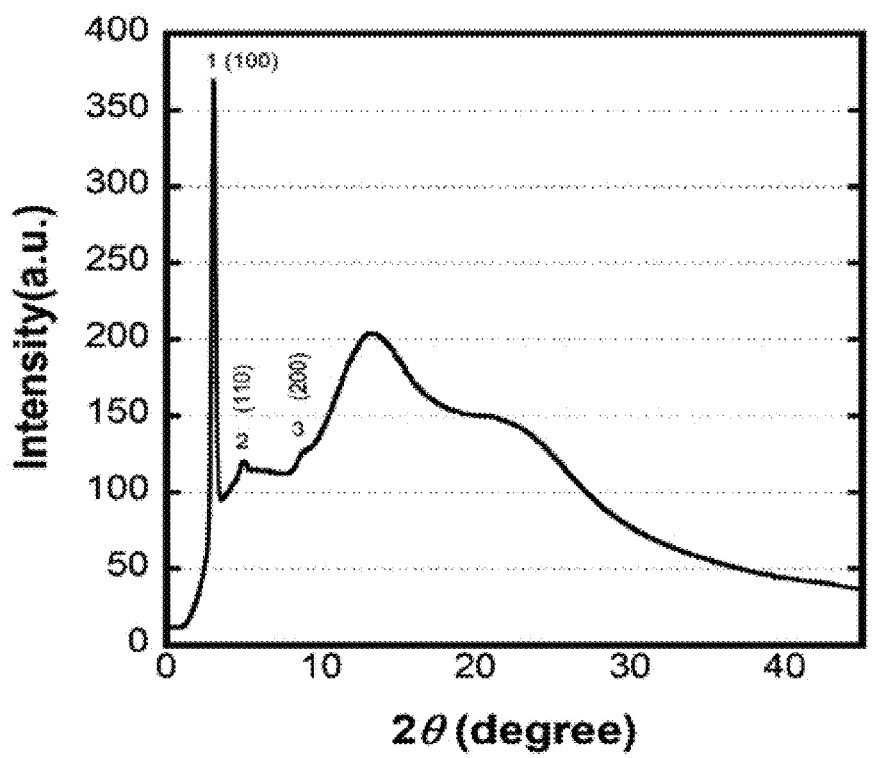
FIG. 26 is a graph showing an X-ray diffraction (XRD) pattern of a compound (5-1) at room temperature.

A graph of FIG. 26 shows an X-ray diffraction (XRD) pattern of the compound (5-1) ((5), m=1, n=1) at room temperature. In FIG. 26, the horizontal axis indicates 2θ (°), and the vertical axis indicates a peak intensity (relative value). Lattice constants calculated from the pattern of FIG. 26 are shown in Table 10 below.

TABLE 10

|   | 2θ | θ | rad | d | lattice constant |
|---|-----|------|-------------|------------|------------------|
| 1 | 3.036 | 1.518 | 0.026494098 | 2.91005E−09 | (100) |
| 2 | 4.708 | 2.354 | 0.041085051 | 1.87688E−09 | (110) |
| 3 | 9.02 | 4.51 | 0.078714349 | 9.80376E−10 | (200) |

In an XRD diffraction pattern shown in FIG. 26, a diffraction peak belonging to (100) and a diffraction peak belonging to (110) were observed, and a ratio of the lattice constants of (100) and (110) was 1: √3 (the square root of 3). Thus, it was considered that the liquid crystal phase of the compound (5-1) was a hexagonal disordered columnar phase. A molecular orientational order was not present in the column. Further, from the XRD diffraction pattern shown in FIG. 26, it was observed that a column gap was 3.1 nm, which was shorter than the molecular length. It is considered that this shows that conformations of oligosiloxane chains are disordered, and the oligosiloxane chains are engaged with one another.

Figure 27:
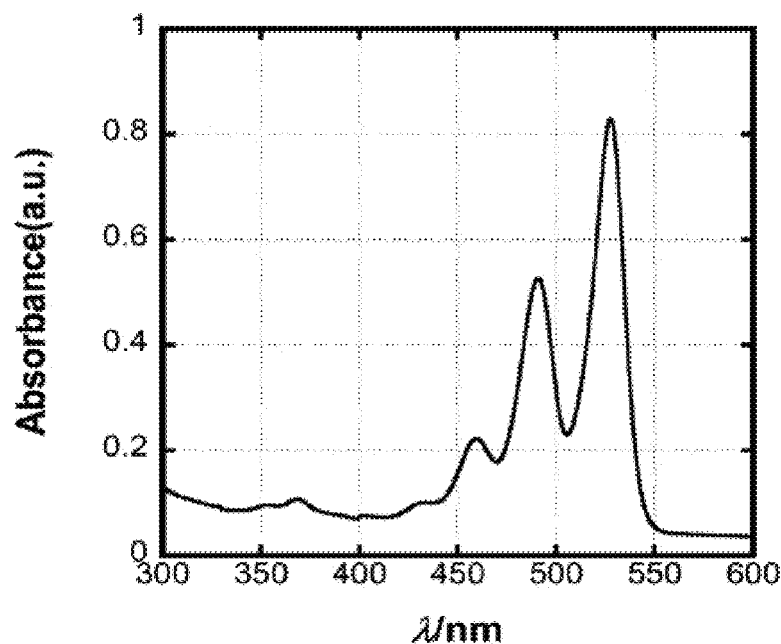
FIG. 27 is an ultraviolet-visible absorption spectrum of a compound (5-1) at room temperature.
Figure 28:
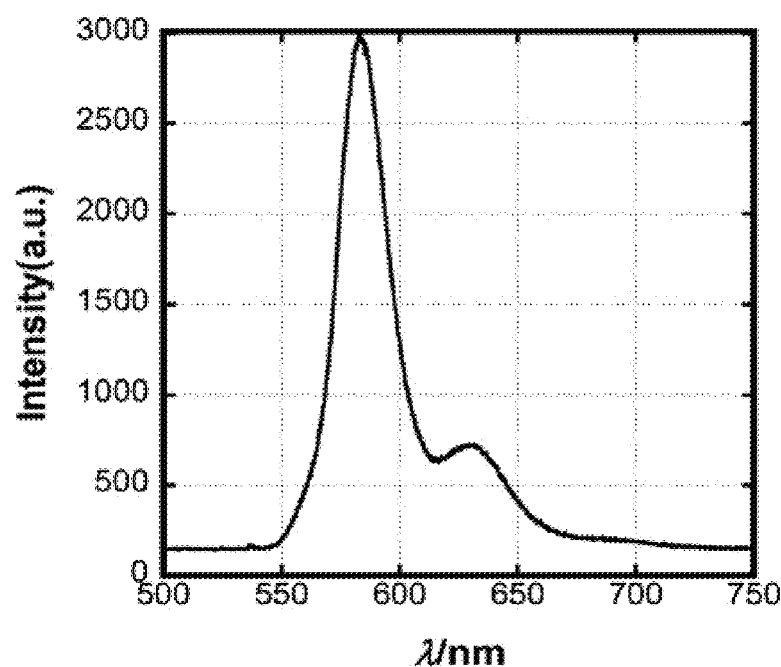
FIG. 28 is a fluorescence spectrum of a compound (5-1) at room temperature.

FIG. 27 shows an ultraviolet-visible absorption spectrum of the compound (5-1) at room temperature. In FIG. 27, the horizontal axis indicates a wavelength (nm), and the vertical axis indicates an absorbance (relative value). FIG. 28 shows a fluorescence spectrum of the compound (5-1) at room temperature. In FIG. 28, the horizontal axis indicates a wavelength (nm), and the vertical axis indicates a fluorescence intensity (relative value). As shown in FIGS. 27 and 28, a perylene skeleton-derived specific peak appeared in each of the absorption spectrum and the fluorescence spectrum, and this supports a structure of the compound (5-1) with the above-described $^1$HNMR, MS, and IR.

Figure 29:
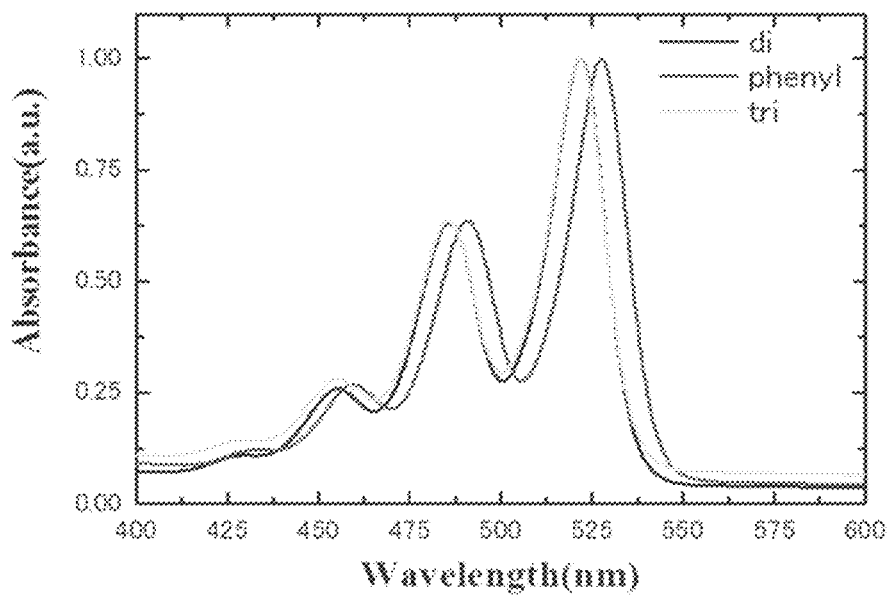
FIG. 29 is a comparison of the ultraviolet-visible absorption spectrum of a compound (5-1) at room temperature with the ultraviolet-visible absorption spectra of compounds (2-46) ((2), m=0, n=3) and (4-1) ((4) ((4), m=0, n=1).
Figure 30:
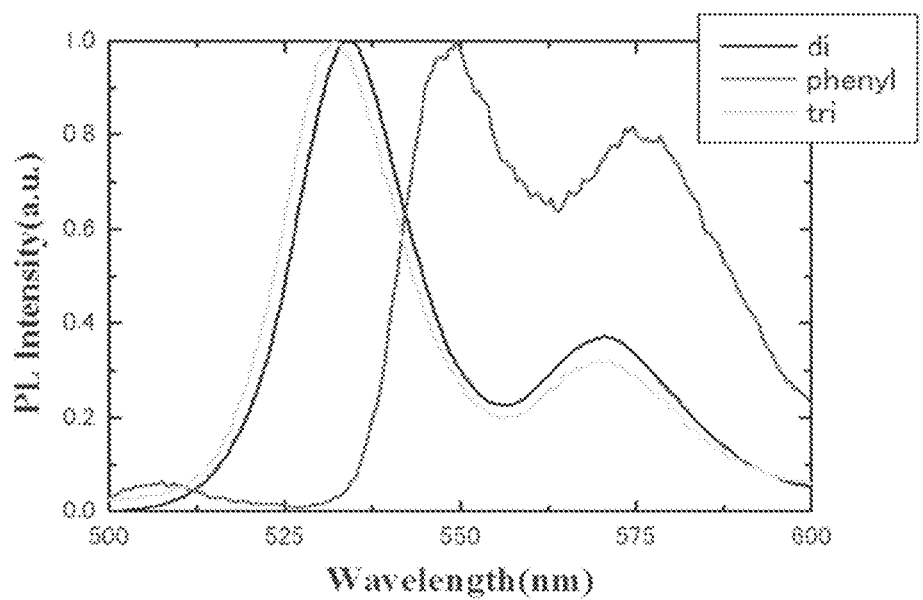
FIG. 30 is a comparison of the ultraviolet-visible absorption spectrum of a compound (5-1) at room temperature with the fluorescence spectra of the compounds (2-46) ((2), m=0, n=3) and (4-1) ((4) ((4), m=0, n=1).
Figure 31:
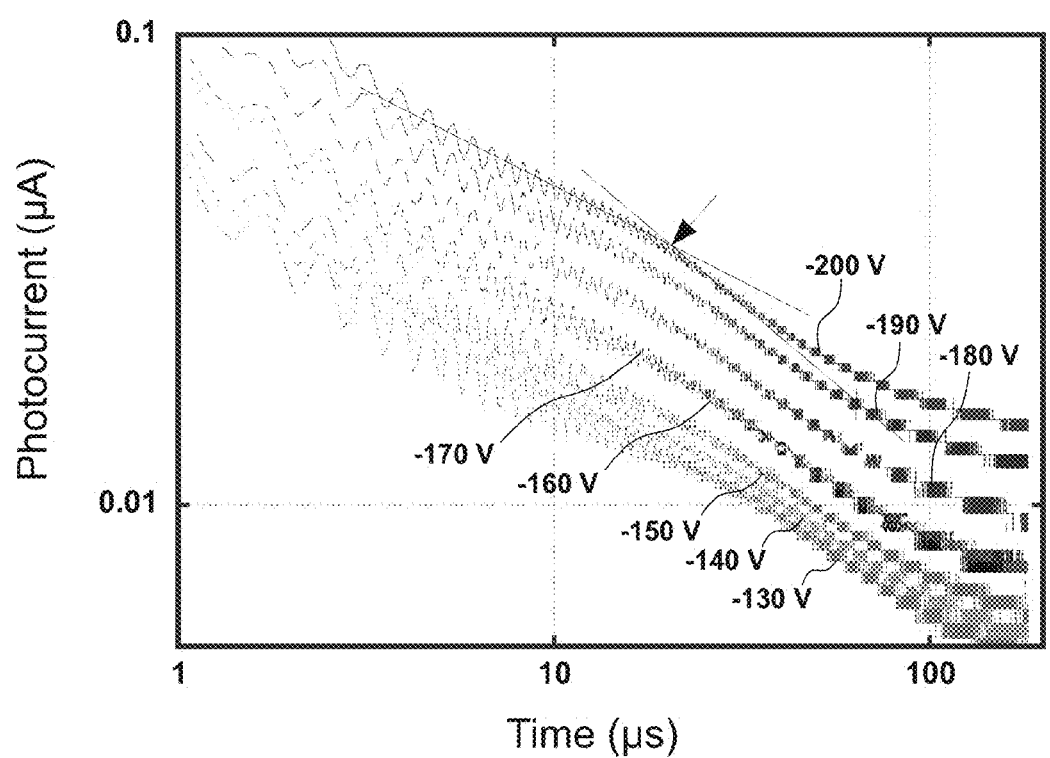
FIG. 31 is a graph showing a result of transient photocurrent measurement of a compound (5-1) by a TOF method.

FIG. 29 shows a comparison of the ultraviolet-visible absorption spectrum of the compound (5-1) at room temperature with the ultraviolet-visible absorption spectra of the compounds (2-46) ((2), m=0, n=3) and (4-1) ((4) ((4), m=0, n=1). In FIG. 29, the horizontal axis indicates a wavelength (nm) and the vertical axis indicates an absorbance (relative value). In FIG. 29, "di" (a black curve) indicates an absorption spectrum of the compound (2-46), "phenyl" (a dark-gray curve) indicates an absorption spectrum of the compound (5-1), and "tri" indicates (a light-gray curve) indicates an absorption spectrum of the compound (4-1). FIG. 30 shows a comparison of the fluorescence spectrum of the compound (5-1) at room temperature with the fluorescence spectra of the compounds (2-46) ((2), m=0, n=3) and (4-1) ((4) ((4), m=0, n=1). In FIG. 30, the horizontal axis indicates a wavelength (nm), and the vertical axis indicates a fluorescence intensity (relative value). In FIG. 30, "di" (a black curve) indicates a fluorescence spectrum of the compound (2-46), "phenyl" (a dark-gray curve) indicates a fluorescence spectrum of the compound (5-1), and "tri" (a light-gray curve) indicates a fluorescence spectrum of the compound (4-1). As shown in FIGS. 29 and 31, there was not much difference in absorption spectrum and fluorescence spectrum between the compound (2-46) and the compound (4-1). In contrast, the absorption spectrum of the compound (5-1) was red-shifted about 10 nm from the absorption spectra of the compound (2-46) and the compound (4-1), and the fluorescence spectrum of the compound (5-1) was red-shifted about 15 nm from the fluorescence spectra of the compound (2-46) and the compound (4-1). This was considered to be because the conjugation length of the compound (5-1) was longer than those of the compound (2-46) and the compound (4-1) because the compound (5-1) had a phenyl group as a linking group.

Charge Transport Properties of N—N'-bis(4-(1,9-di (1,1,1,3,3,5,5-heptamethyltrisiloxanyl)nonane-5-yloxy)phenyl)perylene-3,4,9,10-tetracarboxylic acid bisimide (Compound (5-1) ((5), m=1, n=1))

Charge transport properties (carrier mobility properties) of the liquid crystal compound (5-1) ((5), m=1, n=1) were measured through transient photocurrent measurement by a Time-of-Flight method using the liquid crystal cell produced in Example 13. The transient photocurrent measurement by a Time-of-Flight method was performed in the same manner as in the measurement of charge transport properties (carrier mobility properties) of the liquid crystal compound (5-1) ((5), m=1, n=1). The thickness of a sample of the liquid crystal compound (5-1) ((5), m=1, n=1) was 9 μm. The measurement temperature was room temperature (25° C.), and the measurement was performed while changing an applied voltage from 10 V to 100 V by 10V. The graph of FIG. 31 shows the result of the measurement. In FIG. 31, the horizontal axis indicates time (μs), and the vertical axis indicates a photocurrent (μA). As shown in FIG. 31, in the same time of flight, the higher the applied voltage was, the higher the photocurrent flowed. In FIG. 31, an arrow indicates a transient current. The maximum electron mobility of the liquid crystal compound (5-1) ((5), m=1, n=1) calculated by the TOF method in FIG. 31 was $1 \times 10^{-4}$ cm/Vs. This electron mobility of the liquid crystal compound (5-1) was lower than those of the liquid crystal compounds (2-44) and (2-46). Although the reason for this was unknown, it was considered that this was caused by impurities in the liquid crystal compound (5-1). It is expected that the electron mobility of the liquid crystal compound (5-1) would be further increased by controlling an orientation thereof or purifying it.

As described above, according to the examples of the present invention, novel n-type liquid crystalline semiconductors having an intense photoabsorption band in a visible region, an high electron affinity, and superior electron transport properties could be produced. The compounds (perylene tetracarboxylic acid imide derivatives) of the examples of the present invention and the n-type semiconductors using these compounds have superior properties (A) to (E) shown below.

(A) High Electron Affinity

According to the measurements in solutions by cyclic voltammetry, the compounds of the examples of the present invention had high reduction potentials from −0.83 to −0.86 V. Such high reduction potentials indicate that the compounds have high electron affinities which are advantageous in electron transport. The compounds of the examples of the present invention have the above-described property and thus can function as superior n-type organic semiconductors. For example, when the compounds have high electron affinities (reduction potentials), it is easy to inject electrons from an electrode. Further, in the case where the compounds are laminated on p-type semiconductors or form bulk hetero junctions with p-type semiconductors, electron charge transfer from the p-type semiconductors to the liquid crystal molecules can be easily progressed. This property is advantageous in improving photocarrier generation efficiency in an organic thin-film solar battery, for example.

(B) Exhibition of Liquid Crystal Phase at Room Temperature or Around Room Temperature The compounds of the examples of the present invention can exhibit a liquid crystal phase at room temperature or around room temperature (e.g., about 0° C. to about 50° C.). The exhibition of liquid crystal phase brings about greater overlap of π electron-conjugated molecules, and formation of a structural defect which inhibits electric conduction can be suppressed. The exhibition of such property at room temperature or around room temperature brings about high electron mobility at room temperature or around room temperature as shown below. This property is advantageous in the use as an n-type semiconductor.

(C) High Electron Mobility

An electron mobility of the compound (2-1) of the example of the present invention alone was measured through transient photocurrent measurement by a Time-of-Flight method (without mixing with other substances). The result showed that the electron mobility reached maximum at $10^{-3}$ cm$^2$/Vs in a liquid crystal phase at around room temperature. This electron mobility is higher by an order of magnitude than the electron mobility (about $10^{-4}$ cm$^2$/Vs at a maximum) of a conjugate polymer-fullerene derivative (n-type organic semiconductor) composite currently used in a bulk hetero junction-type organic thin-film solar battery. Such high electron mobility is advantageous in the use as an n-type organic semiconductor. Specifically, for example, it is advantageous in achieving a bulk hetero-type organic thin-film solar battery having high efficiency.

(D) High Solubility

Each of the compounds (1-1) and (2-1) of the examples of the present invention has high solubility in various organic solvents and thus can be formed into a liquid crystalline thin film by a coating method such as a spin coating method.

(E) High Absorption Coefficient in Visible Light Region

In each ultraviolet-visible absorption spectrum of the compounds (1-1) and (2-1) of the examples of the present invention, an absorption band is in a green region, specifically, absorption maximum is at around 525 nm. Thus, the compounds can produce intense yellow to red fluorescence in a solution or in a form of a thin film. Since each of the compounds has an absorption band in a visible light region (visible range) as described above, the compounds are useful as a pigment such as a laser pigment, for example. Moreover, for example, by using the compounds with an oligothiophene derivative and a phthalocyanine derivative each of which are p-type semiconductor, a solar battery having spectral sensitivity in an entire visible range can be produced.

In the compound according to the present invention, besides the compounds (1-1) and (2-1) of the examples of the present invention, other compounds can also have the same properties (A) to (E) or superior properties based thereon. These, however, are merely examples, and the compound according to the present invention is not at all limited thereto. For example, the compound according to the present invention is not limited to the compound having all of the properties (A) to (E) or the effects thereof. Moreover, for example, numerical values such as a reduction potential, a temperature at which a liquid crystal phase is exhibited, electron mobility, and an absorption maximum wavelength of the compound according to the present invention can be changed as appropriate by molecular design of the compound according to the present invention (e.g., the kinds of substituents, the length of side chains, and the like in the chemical formulae (I) and (II)).

While the invention has been described with reference to exemplary embodiments thereof, the invention is not limited to these embodiment. It will be understood by those of ordinary skill in the art that various changes in form and details may be made therein without departing from the spirit and scope of the present invention as defined by the claims.

This application is based upon and claims the benefit of priority from Japanese patent application No. 2011-083220, filed on Apr. 4, 2011, the disclosure of which is incorporated herein in its entirety by reference.

Industrial Applicability

As described above, according to the present invention, a perylene tetracarboxylic acid bisimide derivative which enables an n-type semiconductor having high carrier mobility to be formed and is superior in solubility can be provided. According to the present invention, an n-type semiconductor using the perylene tetracarboxylic acid bisimide derivative, a method for producing the n-type semiconductor, and an electronic device can further be provided. The compound according to the present invention (perylene tetracarboxylic acid bisimide derivative) has high solubility in organic solvents, and thus, the compound can be easily formed into a high-quality thin film by a coating method such as a spin coating method, for example. Further, the compound according to the present invention exhibits a liquid crystal phase at room temperature and has high electron mobility, and thus, the compound can be favorably used as an n-type semiconductor, for example. Furthermore, the compound according to the present invention has a high reduction potential, and thus, it is easy to inject electrons from a metal electrode, and it is easy to transfer electric charges between the molecule of the compound according to the present invention and the molecule of the p-type organic semiconductor by photoexcitation. Thus, by laminating the compound according to the present invention on a thin film of a p-type organic semiconductor or producing a composite of the compound according to the present invention and a thin film of a p-type organic semiconductor, the compound according to the present invention can be applied to an organic thin-film solar battery. The n-type semiconductor according to the present invention also can be applied to an electroluminescence element by laminating it on a p-type semiconductor layer, for example. Moreover, the compound according to the present invention in a solution or in a form of a thin film produces intense yellow to red fluorescence in a visible range, and thus, the compound can be utilized also as a laser pigment or the like, for example. These descriptions of properties and the uses, however, are merely examples, and the present invention is not limited thereby. The n-type semiconductor according to the present invention can be used in any use, and the use of the compound according to the present invention is not limited to the n-type semiconductor and the compound can be used in any use.

The invention claimed is:

1. A perylene tetracarboxylic acid bisimide derivative being a compound represented by the following chemical formula (I) other than a compound represented by the following chemical formula (A); a tautomer or stereoisomer of the perylene tetracarboxylic acid bisimide derivative; or a salt of the perylene tetracarboxylic acid bisimide derivative or the tautomer or stereoisomer,

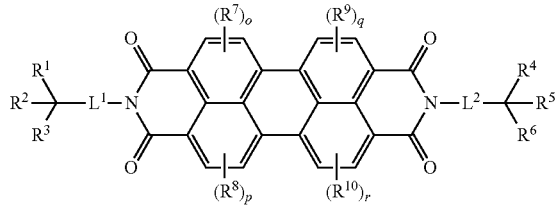

(I)

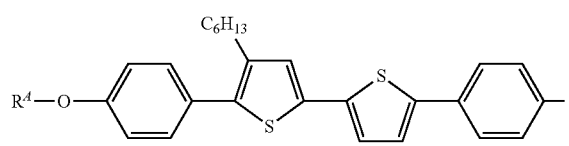

(A)

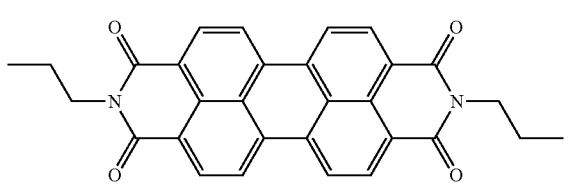

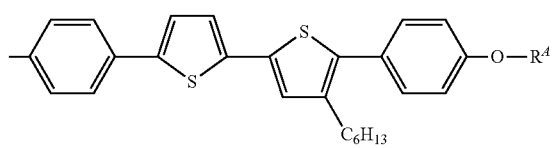

where in the chemical formula (I),

R$^1$ to R$^6$ each represents a hydrogen atom, a monovalent substituent derived from organooligosiloxane, or any substituent and may be identical to or different from one another, where at least one of R$^1$ to R$^6$ represents a monovalent substituent derived from organooligosiloxane, the organooligosiloxane may or may not further have a substituent, and the monovalent substituent derived from organooligosiloxane does not have a circular structure and an amino group, R$^7$ to R$^{10}$ each represents a lower alkyl group, a lower alkoxy group, or a halogen and may be identical to or different from one another, L$^1$ and L$^2$ each represents a single bond or a linking group and may be identical to or different from each other, and o, p, q, and r each represents the number of substituents, which is an integer from 0 to 2 and may be identical to or different from one another, where when o is 2, two R$^7$'s may be identical to or different from each other, when p is 2, two R$^8$s may be identical to or different from each other, and when q is 2, two R$^9$s may be identical to or different from each other, and when r is 2, two R$^{10}$s may be identical to or different from each other, where in the chemical formula (A), R$^A$ is a group represented by the following chemical formula (A1)

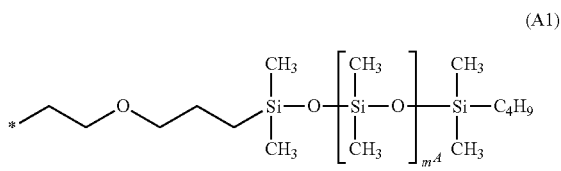

(A1)

where in the chemical formula (A1), m$^A$ is an integer from 0 to 10.

2. The perylene tetracarboxylic acid bisimide derivative according to claim 1, where in the chemical formula (I), in R$^1$ to R$^6$, the monovalent substituent derived from organooligosiloxane is a substituent represented by the following chemical formula (II) or (II-2),

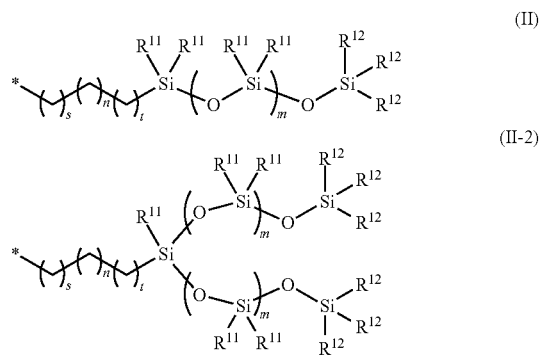

(II)

(II-2)

where in the chemical formulae (II) and (II-2),

R$^{11}$s and R$^{12}$s each represents a hydrogen atom, a lower alkyl group, or a fluorine atom and may be identical to or different from one another, R$^{11}$s may be identical to or different from one another, and R$^{12}$s may be identical to or different from one another, m represents 0 or a positive integer, and when a plurality of ms is present in the chemical formula (I), ms may be identical to or different from one another, n represents 0 or a positive integer, and when a plurality of ns is present in the chemical formula (I), ns may be identical to or different from one another, s represents 0 or 1, t represents 1 or 2, and

* represents an atomic bonding to a carbon atom in the chemical formula (I);

a tautomer or stereoisomer of the perylene tetracarboxylic acid bisimide derivative; or a salt of the perylene tetracarboxylic acid bisimide derivative or the tautomer or stereoisomer.

3. The perylene tetracarboxylic acid bisimide derivative according to claim 2, where in the chemical formula (II), m represents an integer from 0 to 20, and n represents an integer from 0 to 30;

a tautomer or stereoisomer of the perylene tetracarboxylic acid bisimide derivative; or a salt of the perylene tetracarboxylic acid bisimide derivative or the tautomer or stereoisomer.

4. The perylene tetracarboxylic acid bisimide derivative according to claim 1, where in the chemical formula (I),
in $L^1$ and $L^2$,
the linking group is an alkylene group, a saturated hydrocarbon group having a circular structure, an unsaturated hydrocarbon group, an oxy group (—O—), a thio group (—S—), a seleno group (—Se—), an amide bond (—NH—CO— or —CO—NH—), an ester bond (—CO—O— or —O—CO—), an imino group (—NH—), or a thioester bond (—CO—S— or —S—CO—), where
the alkylene group, the saturated hydrocarbon group having a circular structure, and the unsaturated hydrocarbon group each may or may not further have a substituent, and
when the alkylene group, the saturated hydrocarbon group having a circular structure, and the unsaturated hydrocarbon group each have a methylene group, the methylene group may be replaced with an oxy group (—O—), a thio group (—S—), a seleno group (—Se—), an amide bond (—NH—CO— or —CO—NH—), an ester bond (—CO—O— or —O—CO—), an imino group (—NH—), or a thioester bond (—CO—S— or —S—CO—) or is a group represented by the following formula (III),

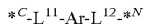 (III)

where in the formula (III),
Ar represents an arylene group, and when a plurality of Ars is present in the chemical formula (I), Ars may be identical to or different from one another, and
$L^{11}$ and $L^{12}$ are each a single bond, an alkylene group, a saturated hydrocarbon group having a circular structure, an unsaturated hydrocarbon group, an oxy group (—O—), a thio group (—S—), a seleno group (—Se—), an amide bond (—NH—CO— or —CO—NH—), an ester bond (—CO—O— or —O—CO—), an imino group (—NH—), or a thioester bond (—CO—S— or —S—CO—),
the alkylene group, the saturated hydrocarbon group having a circular structure, or the unsaturated hydrocarbon group each may or may not further have a substituent,
when the alkylene group, the saturated hydrocarbon group having a circular structure, and the unsaturated hydrocarbon group each have a methylene group, the methylene group may be replaced with an oxy group (—O—), a thio group (—S—), a seleno group (—Se—), an amide bond (—NH—CO— or —CO—NH—), an ester bond (—CO—O— or —O—CO—), an imino group (—NH—), or a thioester bond (—CO—S— or —S—CO—),
$L^{11}$ and $L^{12}$ may be identical to or different from each other,
when a plurality of $L^{11}$s is present in the chemical formula (I), $L^{11}$s may be identical to or different from one another,
when a plurality of $L^{12}$s is present in the chemical formula (I), $L^{12}$s may be identical to or different from one another,
*C represents an atomic bonding to a carbon atom in the chemical formula (I), and
*N represents an atomic bonding to a nitrogen atom in the chemical formula (I);
a tautomer or stereoisomer of the perylene tetracarboxylic acid bisimide derivative; or
a salt of the perylene tetracarboxylic acid bisimide derivative or the tautomer or stereoisomer.

5. The perylene tetracarboxylic acid bisimide derivative according to claim 4, where in the chemical formula (III),
Ar is an o-phenylene group, a m-phenylene group, a p-phenylene group, a 2,2'-biphenylene group, a 2,3'-biphenylene group, a 2,4'-biphenylene group, a 3,3'-biphenylene group, a 3,4'-biphenylene group, a 4,4'-biphenylene group, or a 2,5-thienylene group;
a tautomer or stereoisomer of the perylene tetracarboxylic acid bisimide derivative; or
a salt of the perylene tetracarboxylic acid bisimide derivative or the tautomer or stereoisomer.

6. The perylene tetracarboxylic acid bisimide derivative according to claim 4, where in the chemical formula (III),
in $L^1$ and $L^2$, the linking group is a single bond, an alkylene group, an oxy group (—O—), a thio group (—S—), or a seleno group (—Se—);
a tautomer or stereoisomer of the perylene tetracarboxylic acid bisimide derivative; or
a salt of the perylene tetracarboxylic acid bisimide derivative or the tautomer or stereoisomer.

7. The perylene tetracarboxylic acid bisimide derivative according to claim 2, represented by the following chemical formula (1) or (2),

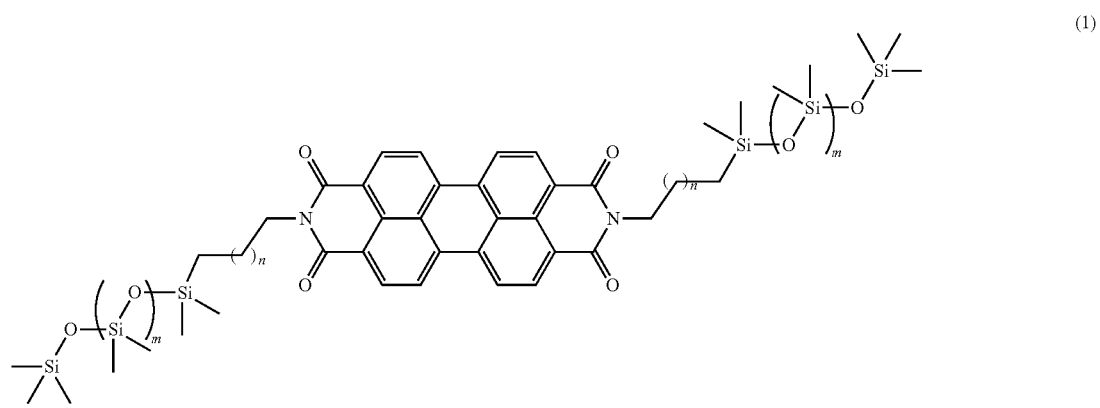

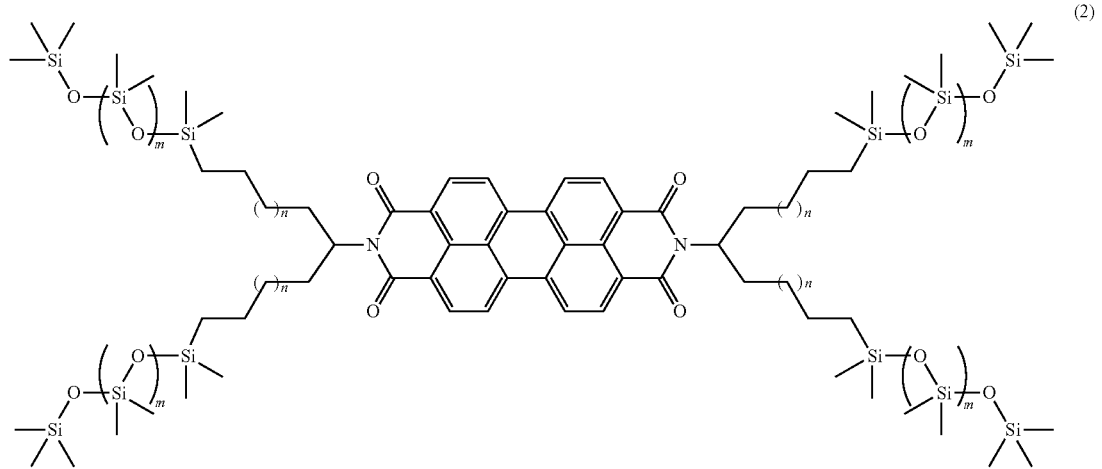

where in the chemical formulae (1) and (2),
m and n are the same as those in the chemical formula (II);
a tautomer or stereoisomer of the perylene tetracarboxylic acid bisimide derivative; or
a salt of the perylene tetracarboxylic acid bisimide derivative or the tautomer or stereoisomer.

8. The perylene tetracarboxylic acid bisimide derivative according to claim 7, represented by the following chemical formula (1-1), (2-1), (2-44), or (2-46),

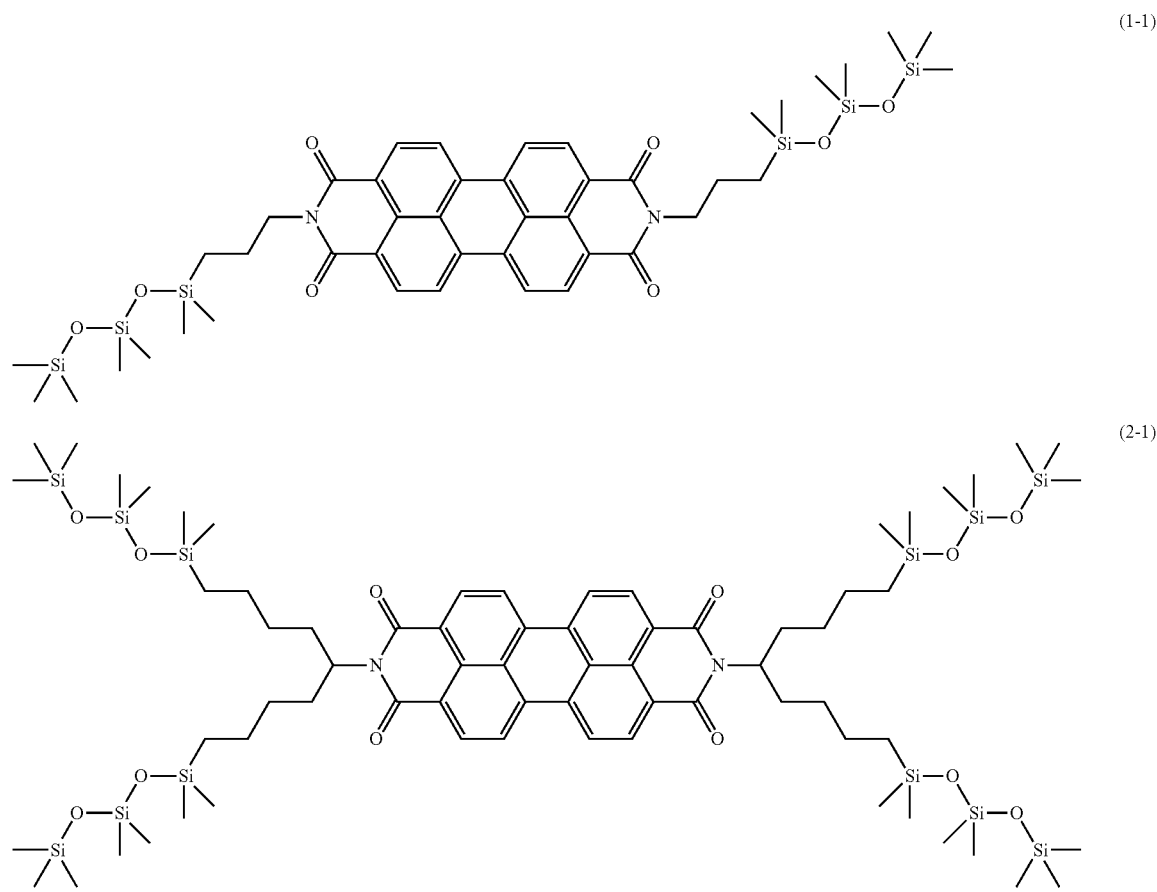

(2-44)

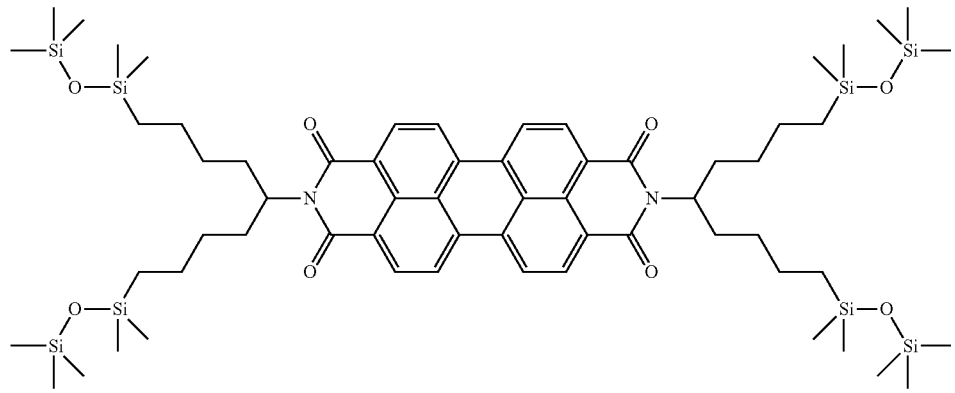

(2-46)

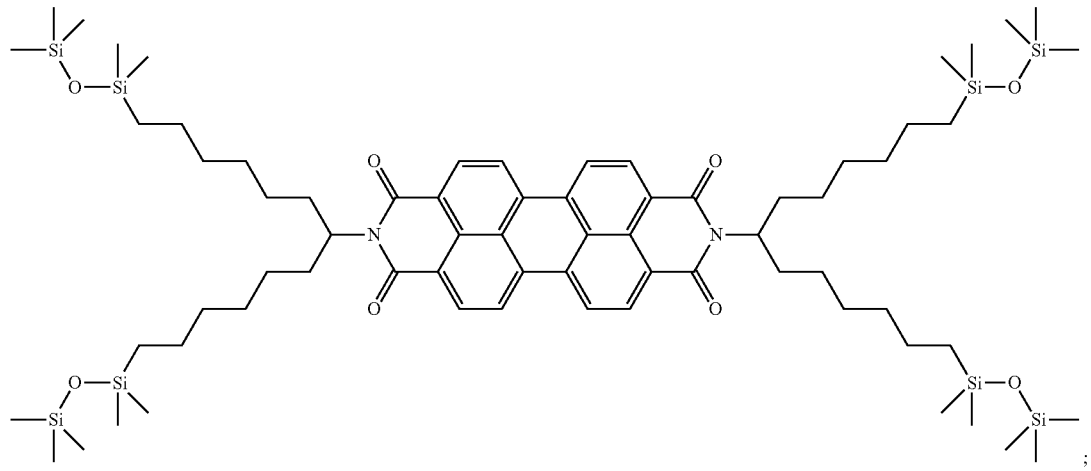
;

a tautomer or stereoisomer of the perylene tetracarboxylic acid bisimide derivative; or a salt of the perylene tetracarboxylic acid bisimide derivative or the tautomer or stereoisomer.

9. The perylene tetracarboxylic acid bisimide derivative according to claim 2, represented by the following chemical formula (3), where in the chemical formula (3), m and n are the same as those in the chemical formula (II);

a tautomer or stereoisomer of the perylene tetracarboxylic acid bisimide derivative; or a salt of the perylene tetracarboxylic acid bisimide derivative or the tautomer or stereoisomer.

(3)

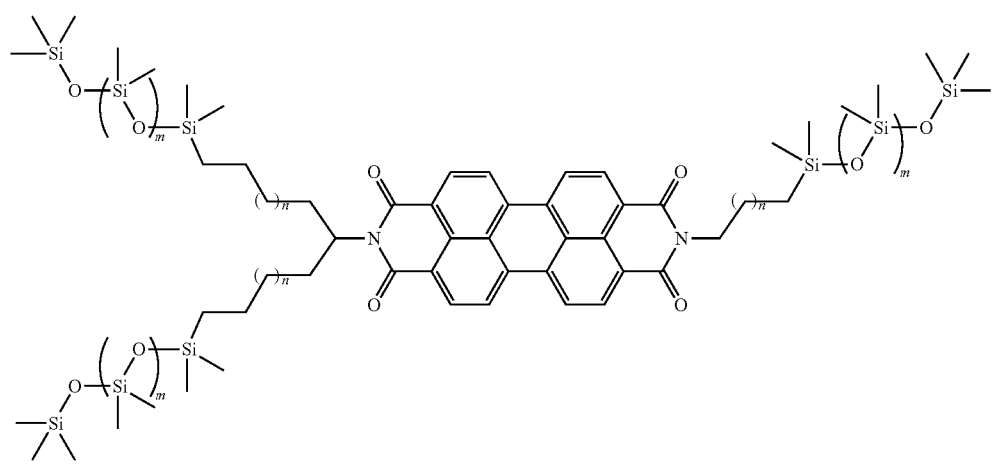

10. The perylene tetracarboxylic acid bisimide derivative according to claim 2, represented by the following chemical formula (4),

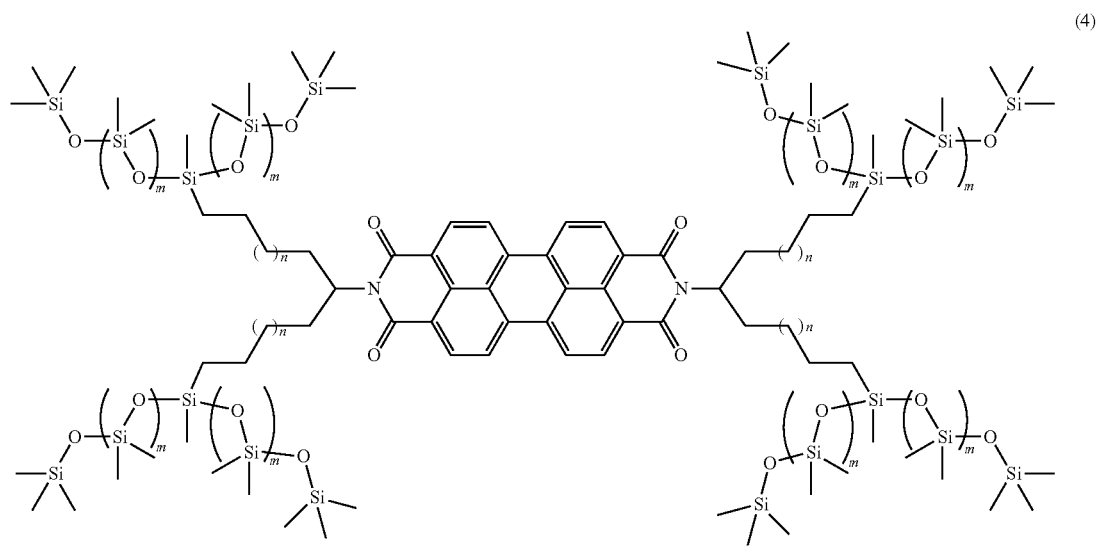

wherein the chemical formula (4),
m and n are the same as those in the chemical formula (II);
a tautomer or stereoisomer of the perylene tetracarboxylic acid bisimide derivative; or
a salt of the perylene tetracarboxylic acid bisimide derivative or the tautomer or stereoisomer.

11. The perylene tetracarboxylic acid bisimide derivative according to claim 10, represented by the following chemical formula (4-1),

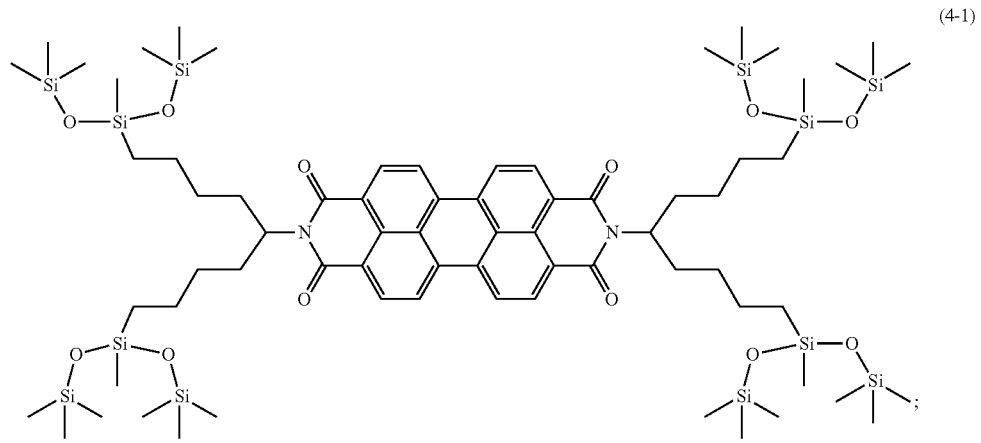

a tautomer or stereoisomer of the perylene tetracarboxylic acid bisimide derivative; or
a salt of the perylene tetracarboxylic acid bisimide derivative or the tautomer or stereoisomer.

12. The perylene tetracarboxylic acid bisimide derivative according to claim 2, represented by the following chemical formula (5),

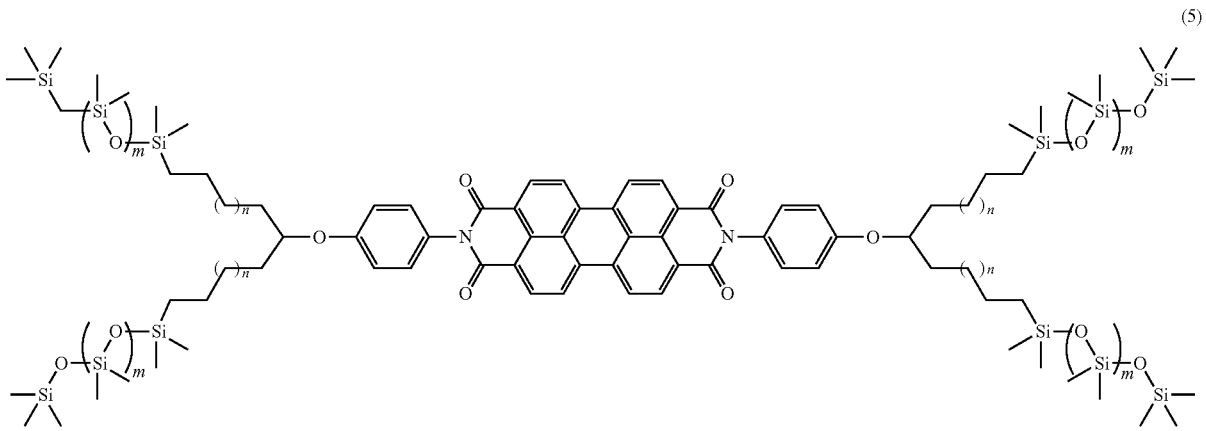

(5)

where in the chemical formula (5),
m and n are the same as those in the chemical formula (II);
a tautomer or stereoisomer of the perylene tetracarboxylic acid bisimide derivative; or
a salt of the perylene tetracarboxylic acid bisimide derivative or the tautomer or stereoisomer.

13. The perylene tetracarboxylic acid bisimide derivative according to claim 12, represented by the following chemical formula (5-1),

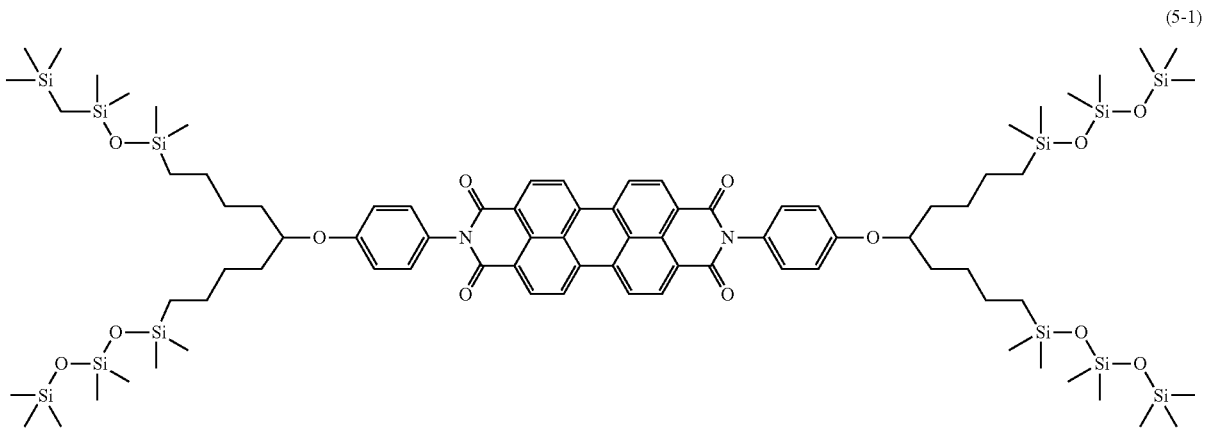

(5-1)

a tautomer or stereoisomer of the perylene tetracarboxylic acid bisimide derivative; or
a salt of the perylene tetracarboxylic acid bisimide derivative or the tautomer or stereoisomer.

14. The perylene tetracarboxylic acid bisimide derivative according to claim 1, which is in a form of a liquid crystalline compound;
a tautomer or stereoisomer of the perylene tetracarboxylic acid bisimide derivative; or
a salt of the perylene tetracarboxylic acid bisimide derivative or the tautomer or stereoisomer.

15. An n-type semiconductor comprising the perylene tetracarboxylic acid bisimide derivative according to claim 1, a tautomer or stereoisomer of the perylene tetracarboxylic acid bisimide derivative, or a salt of the perylene tetracarboxylic acid bisimide derivative or the tautomer or stereoisomer.

16. The n-type semiconductor according to claim 15, which is a laser pigment or a photoconductor.

17. A method for producing an n-type semiconductor comprising the perylene tetracarboxylic acid bisimide derivative according to claim 1, a tautomer or stereoisomer of the perylene tetracarboxylic acid bisimide derivative, or a salt of the perylene tetracarboxylic acid bisimide derivative or the tautomer or stereoisomer, comprising:

a solution preparation step of dissolving the perylene tetracarboxylic acid bisimide derivative according to claim 1, a tautomer or stereoisomer of the perylene tetracarboxylic acid bisimide derivative, or a salt of the perylene tetracarboxylic acid bisimide derivative or the tautomer or stereoisomer in a solvent to prepare a solution;

a coating step of coating a base with the solution to form a coating film; and a drying step of drying the coating film.

18. An electronic device comprising the n-type semiconductor according to claim 15.

19. The electronic device according to claim 18, which is a battery, a solar battery, a laser, an organic EL device, an electroluminescence element, a transistor, or a memory element.

* * * * *